(12) United States Patent
Trischler et al.

(10) Patent No.: US 11,744,706 B2
(45) Date of Patent: *Sep. 5, 2023

(54) SPINAL SPACING IMPLANT, SPINAL SPACER ASSEMBLY, EXPANDER AND INSERTION INSTRUMENT, KIT AND METHODS OF ASSEMBLY AND USE

(71) Applicant: MEDIVEST, LLC, Columbia City, IN (US)

(72) Inventors: Cory Trischler, Fort Wayne, IN (US); Kreigh Williams, Fort Wayne, IN (US); Brian G. Emerick, Columbia City, IN (US); Greg Stalcup, Fort Wayne, IN (US); James Tumavich, Kalamazoo, MI (US)

(73) Assignee: MEDIVEST, LLC, Columbia City, IN (US)

( * ) Notice: Subject to any disclaimer, the term of this patent is extended or adjusted under 35 U.S.C. 154(b) by 474 days.

This patent is subject to a terminal disclaimer.

(21) Appl. No.: 16/890,180

(22) Filed: Jun. 2, 2020

(65) Prior Publication Data
US 2020/0289270 A1 Sep. 17, 2020

Related U.S. Application Data

(63) Continuation of application No. 15/592,732, filed on May 11, 2017, now Pat. No. 10,667,915, which is a
(Continued)

(51) Int. Cl.
*A61F 2/28* (2006.01)
*A61F 2/46* (2006.01)
(Continued)

(52) U.S. Cl.
CPC .............. *A61F 2/28* (2013.01); *A61B 17/885* (2013.01); *A61F 2/30771* (2013.01); *A61F 2/44* (2013.01);
(Continued)

(58) Field of Classification Search
CPC .. A61F 2/28; A61F 2/46; A61F 2/4657; A61F 2/4611; A61F 2/44; A61B 17/88; A61B 17/885
See application file for complete search history.

(56) References Cited

U.S. PATENT DOCUMENTS

| 6,193,755 B1 | 2/2001 | Metz-Stavenhagen |
| 6,193,756 B1 | 2/2001 | Studer |

(Continued)

FOREIGN PATENT DOCUMENTS

| WO | 2005006944 | 1/2005 |
| WO | 2011060071 | 5/2011 |

OTHER PUBLICATIONS

International Search Report for PCT/US2013/025134 dated May 29, 2013, 4 pages.

(Continued)

*Primary Examiner* — Christopher J Beccia
(74) *Attorney, Agent, or Firm* — HESLIN ROTHENBERG FARLEY & MESITI PC; Jacquelyn A. Graff, Esq.

(57) ABSTRACT

Spinal spacing implants, spinal spacer assembly, expander and insertion instruments, kits and methods of assembly and use are disclosed. The spinal implant replacement instrument kit including a distraction instrument, a spacer inserter, and a spinal implant. A distraction instrument includes a first inserter member, a second inserter member, a first arm coupled to the first inserter member, a second arm coupled to the second inserter member, a distraction system coupled to the first arm and second arm, a first handle coupled to the first arm and the distraction system, and a second handle coupled to the second arm and the distraction system. Spinal (Continued)

spacing implants, spinal spacer assemblies, and methods of assembling and using the implants assemblies, and instruments are also disclosed.

24 Claims, 76 Drawing Sheets

Related U.S. Application Data continuation of application No. PCT/US2015/060420, filed on Nov. 12, 2015.

(60) Provisional application No. 62/078,837, filed on Nov. 12, 2014, provisional application No. 62/180,981, filed on Jun. 17, 2015.

(51) Int. Cl.
| | | |
|---|---|---|
| *A61B 17/88* | (2006.01) | |
| *A61F 2/44* | (2006.01) | |
| *A61F 2/30* | (2006.01) | |
| *A61B 17/00* | (2006.01) | |
| *A61B 90/00* | (2016.01) | |
| *A61B 17/02* | (2006.01) | |

(52) U.S. Cl.
CPC .......... *A61F 2/4611* (2013.01); *A61F 2/4657* (2013.01); *A61B 2017/0046* (2013.01); *A61B 2017/00473* (2013.01); *A61B 2017/0256* (2013.01); *A61B 2090/061* (2016.02); *A61F 2/4425* (2013.01); *A61F 2002/2835* (2013.01); *A61F 2002/305* (2013.01); *A61F 2002/30224* (2013.01); *A61F 2002/30235* (2013.01); *A61F 2002/30387* (2013.01); *A61F 2002/30604* (2013.01); *A61F 2002/30774* (2013.01); *A61F 2002/30818* (2013.01); *A61F 2002/30828* (2013.01); *A61F 2002/30836* (2013.01); *A61F 2002/30878* (2013.01); *A61F 2002/443* (2013.01); *A61F 2002/4615* (2013.01); *A61F 2002/4658* (2013.01)

(56) References Cited

U.S. PATENT DOCUMENTS

| | | |
|---|---|---|
| 6,447,518 B1 | 9/2002 | Krause et al. |
| 6,616,695 B1 | 9/2003 | Crozet et al. |
| 7,214,243 B2 | 5/2007 | Taylor |
| 7,803,191 B2 | 9/2010 | Biedermann et al. |
| 8,480,715 B2 | 7/2013 | Gray |
| 8,540,721 B2 | 9/2013 | Lee et al. |
| 8,828,019 B1 | 9/2014 | Raymond et al. |
| 8,864,770 B2 | 10/2014 | Blain et al. |
| 10,667,915 B2* | 6/2020 | Trischler ............... A61F 2/4611 |
| 2002/0082696 A1 | 6/2002 | Harms |
| 2002/0099444 A1 | 7/2002 | Boyd et al. |
| 2005/0209697 A1 | 9/2005 | Paponneau |
| 2006/0058877 A1 | 3/2006 | Gutlin |
| 2006/0200244 A1 | 9/2006 | Assaker |
| 2006/0241641 A1* | 10/2006 | Albans ............... A61B 17/0218 606/90 |
| 2007/0225726 A1 | 9/2007 | Dye et al. |
| 2008/0021559 A1 | 1/2008 | Thramann |
| 2008/0114357 A1 | 5/2008 | Allard |
| 2008/0161817 A1 | 7/2008 | Parsons et al. |
| 2008/0161926 A1 | 7/2008 | Melkent |
| 2008/0167720 A1 | 7/2008 | Melkent |
| 2008/0177387 A1 | 7/2008 | Parimore |
| 2008/0243254 A1 | 10/2008 | Butler |
| 2009/0105825 A1 | 4/2009 | Foreman |
| 2009/0222100 A1 | 9/2009 | Cipoletti et al. |
| 2009/0254181 A1 | 10/2009 | Boyd et al. |
| 2010/0094424 A1 | 1/2010 | Woodburn |
| 2010/0145394 A1 | 6/2010 | Harvey et al. |
| 2010/0179655 A1 | 7/2010 | Hansell |
| 2010/0179658 A1 | 7/2010 | Freeman et al. |
| 2010/0249792 A1* | 9/2010 | Bonvallet ............ A61B 17/025 606/90 |
| 2011/0218631 A1 | 9/2011 | Woodburn et al. |
| 2011/0245927 A1* | 10/2011 | Farris .................... A61F 2/4637 623/17.11 |
| 2011/0307065 A1 | 12/2011 | Hsu et al. |
| 2012/0101576 A1 | 4/2012 | Dewey |
| 2012/0130493 A1 | 5/2012 | McLaughlin |
| 2012/0209384 A1 | 8/2012 | Arnold |
| 2012/0232660 A1 | 9/2012 | Davenport |
| 2013/0006359 A1 | 1/2013 | Fedorov |
| 2013/0226244 A1 | 8/2013 | Davenport et al. |
| 2013/0310938 A1 | 11/2013 | Sournac |
| 2014/0107787 A1 | 4/2014 | Stinchfield |
| 2014/0207236 A1 | 7/2014 | Prevost |
| 2014/0277471 A1 | 9/2014 | Gray et al. |
| 2015/0066146 A1 | 3/2015 | Laubert |

OTHER PUBLICATIONS

International Preliminary Report on Patentability for PCT/2013/025134 dated Aug. 12, 2014, 9 pages.
International Search Report for PCT/US2013/044563 dated Sep. 6, 2013, 4 pages.
Written Opinion of the International Searching Authority for PCT/US2013/044563 dated Sep. 6, 2013, 6 pages.
International Preliminary Report on Patentability for PCT/US2013/044563 dated Dec. 9, 2014, 7 pages.
International Search Report and Written Opinion of the International Searching Authority issued for PCT Application Mo PCT/US2015/060420 dated Jan. 28, 2016.

* cited by examiner

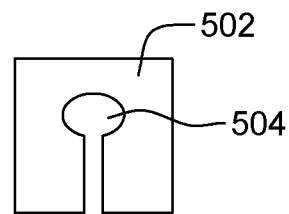
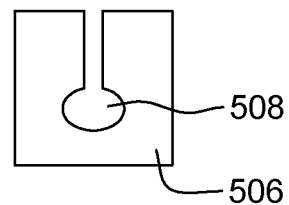
FIG. 12
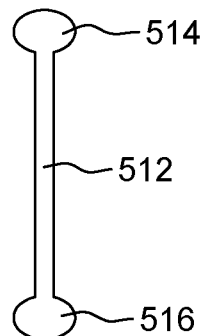
FIG. 13

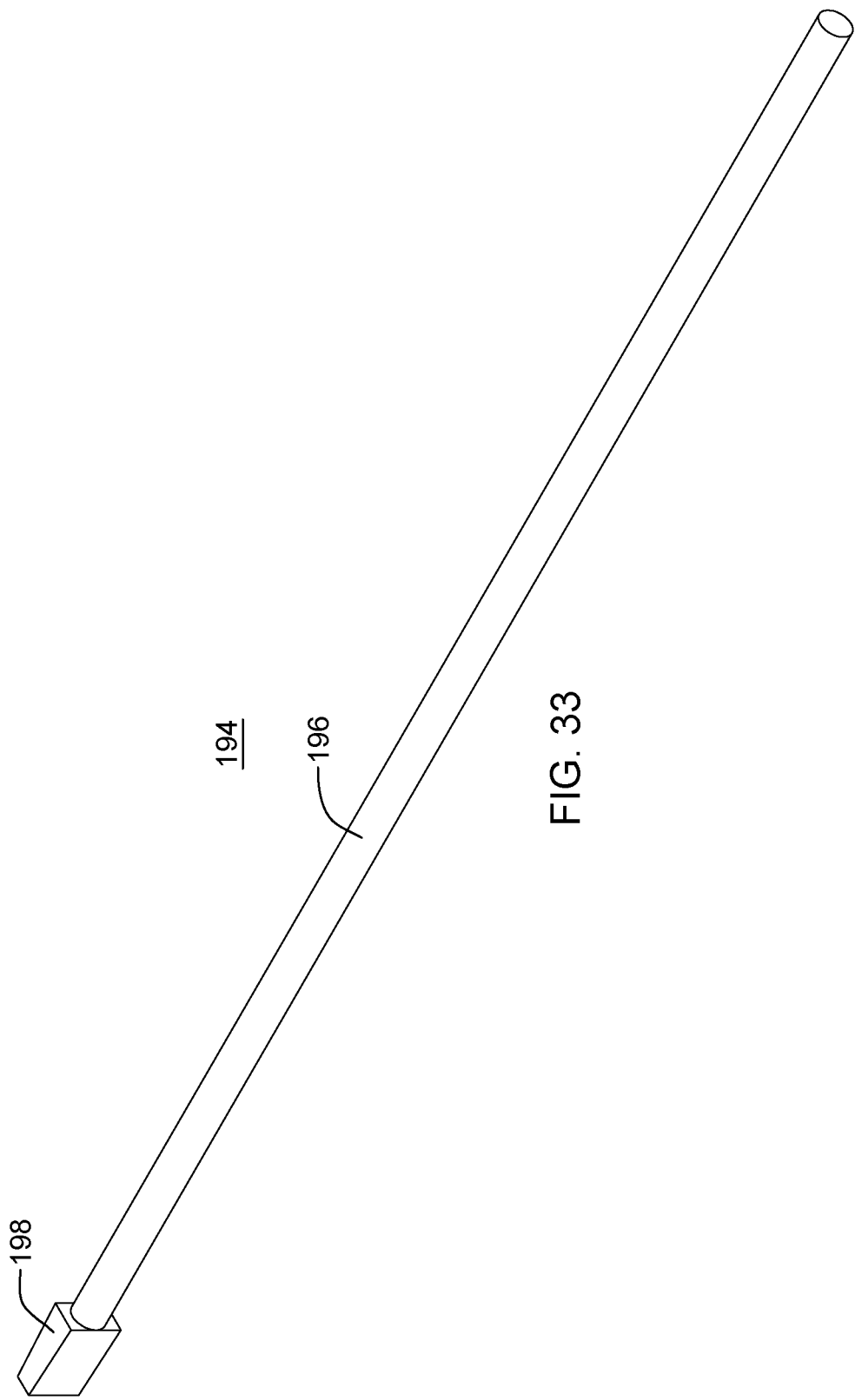

SPINAL SPACING IMPLANT, SPINAL SPACER ASSEMBLY, EXPANDER AND INSERTION INSTRUMENT, KIT AND METHODS OF ASSEMBLY AND USE

CROSS REFERENCE TO RELATED APPLICATIONS

This application is a continuation of U.S. application Ser. No. 15/592,732 filed May 11, 2017 which will issue as U.S. Pat. No. 10,667,915 on Jun. 2, 2020; which claimed priority benefit to PCT Application No. PCT/US2015/060420 filed on Nov. 12, 2015, which claimed priority to U.S. provisional application Nos. 62/078,837 filed Nov. 12, 2014 and 62/180,981 filed Jun. 17, 2015, which all of these applications are incorporated herein by reference in their entireties.

TECHNICAL FIELD

The present invention relates generally to general surgery, orthopaedic and neurosurgical implants used for insertion within a space between hard and soft tissue structures, and more specifically, but not exclusively, concerns spinal spacing implants and surgical instruments for implanting devices within a bone to replace a resected, fractured or diseased portion and to maintain or reestablish proper spacing between the bone fragments.

SUMMARY

The present invention is directed toward implants, assemblies, instruments, kits and methods of assembling and using the implants, assemblies, instruments, kits.

In one aspect, provided herein is a spinal implant replacement instrument kit, including a distraction instrument and a spinal implant.

In another aspect, provided herein is a distraction instrument including a first inserter member, a second inserter member, a first arm coupled to the first inserter member, a second arm coupled to the second inserter member, a distraction system coupled to the first arm and second arm, a first handle coupled to the first arm and the distraction system, and a second handle coupled to the second arm and the distraction system.

In yet another aspect, provided herein is a method for inserting a vertebral body replacement device, including obtaining the vertebral body replacement device and a distraction instrument. The method may also include attaching a first member and a second member of the vertebral body replacement to the distraction instrument and moving the distraction instrument to separate the first member and the second member. The method may further include coupling a spacer to a spacer inserter and moving the coupled spacer and spacer inserter through the distraction instrument into position between the first member and the second member. Finally, the method may include disengaging the spacer inserter from the spacer and removing the spacer inserter from the distraction instrument and disengaging the distraction instrument from the first member and second member of the vertebral body replacement device.

These, and other objects, features and advantages of this invention will become apparent from the following detailed description of the various aspects of the invention taken in conjunction with the accompanying drawings.

BRIEF DESCRIPTION OF THE DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which:

FIG. 12 is a locking mechanism for coupling to the distraction instrument of FIG. 1, in accordance with an aspect of the present invention;

FIG. 13 is a key for the locking mechanism of FIG. 12, in accordance with an aspect of the present invention;

FIG. 33 is a perspective view of one embodiment of an expansion mechanism, in accordance with an aspect of the present invention;

DETAILED DESCRIPTION OF THE INVENTION

Generally stated, disclosed herein are spinal spacing implants, spinal spacing instruments, and a spinal spacer assembly. Further, disclosed herein are an expander and insertion replacement instrument kit and methods for using the spinal spacing replacement instruments.

In this detailed description and the following claims, the words proximal, distal, anterior, posterior, medial, lateral, superior and inferior are defined by their standard usage for indicating a particular part of a bone, prosthesis or surgical instrument according to the relative disposition of the surgical instrument or directional terms of reference. For example, "proximal" means the portion of an instrument positioned nearest the torso, while "distal" indicates the part of the instrument farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Also, the terms "implant" and "device" may be used interchangeably and have the same meaning herein.

Figure 23:
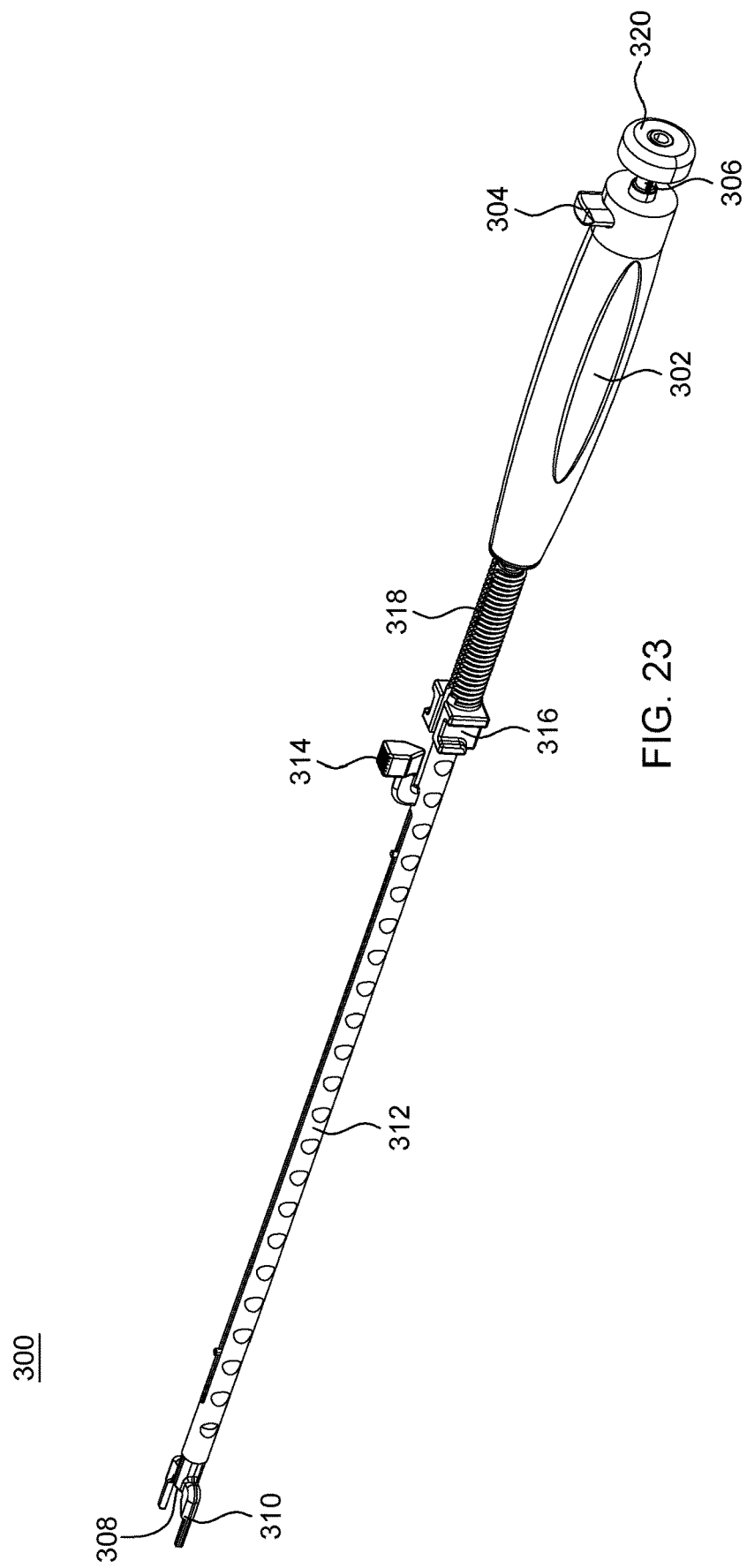
FIG. 23 is a side perspective view of a spacer inserter, in accordance with an aspect of the present invention.
Figure 24:
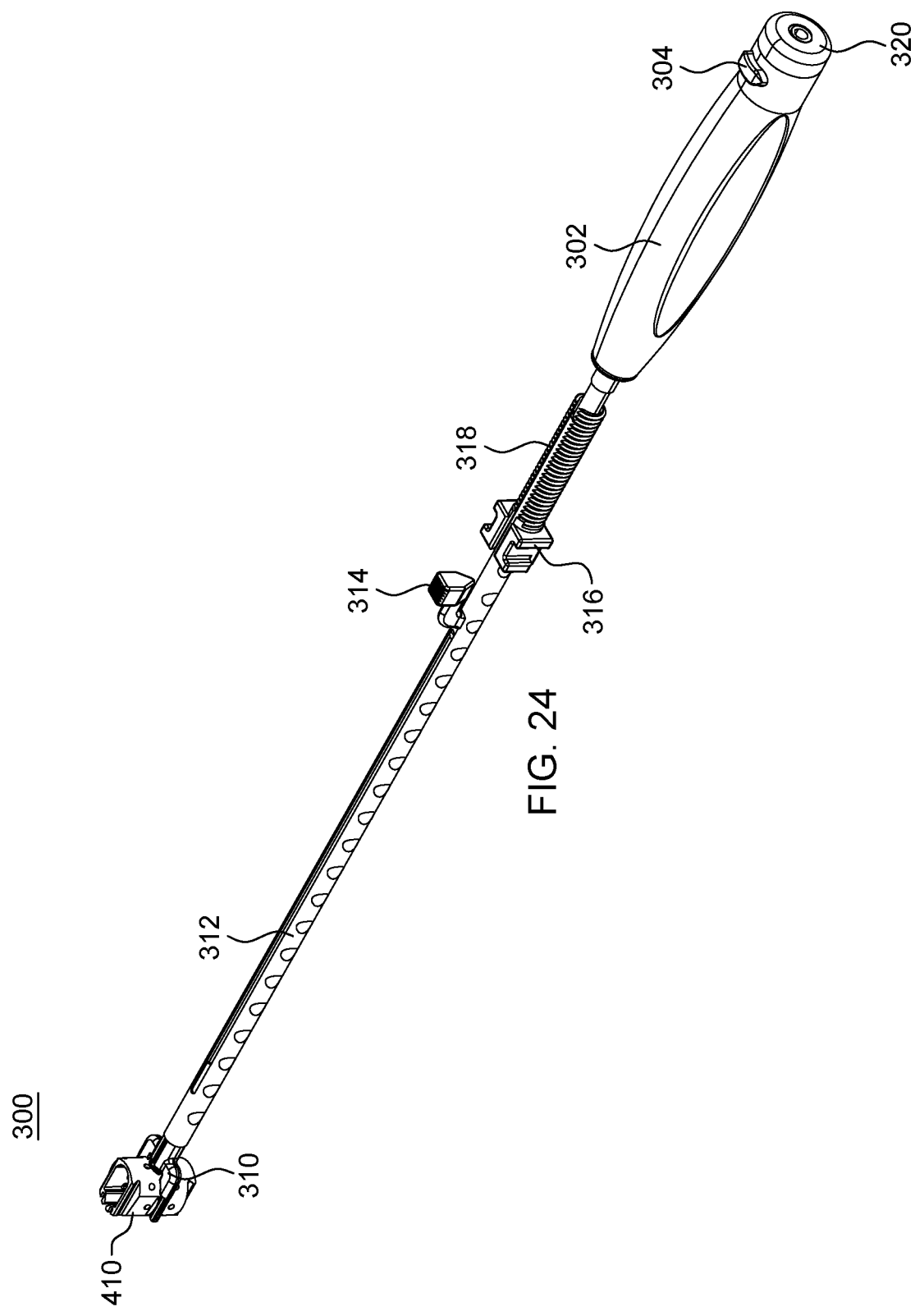
FIG. 24 is a top perspective view of the spacer inserter of FIG. 23 with a spacer coupled to the proximal end, in accordance with an aspect of the present invention.
Figure 25:
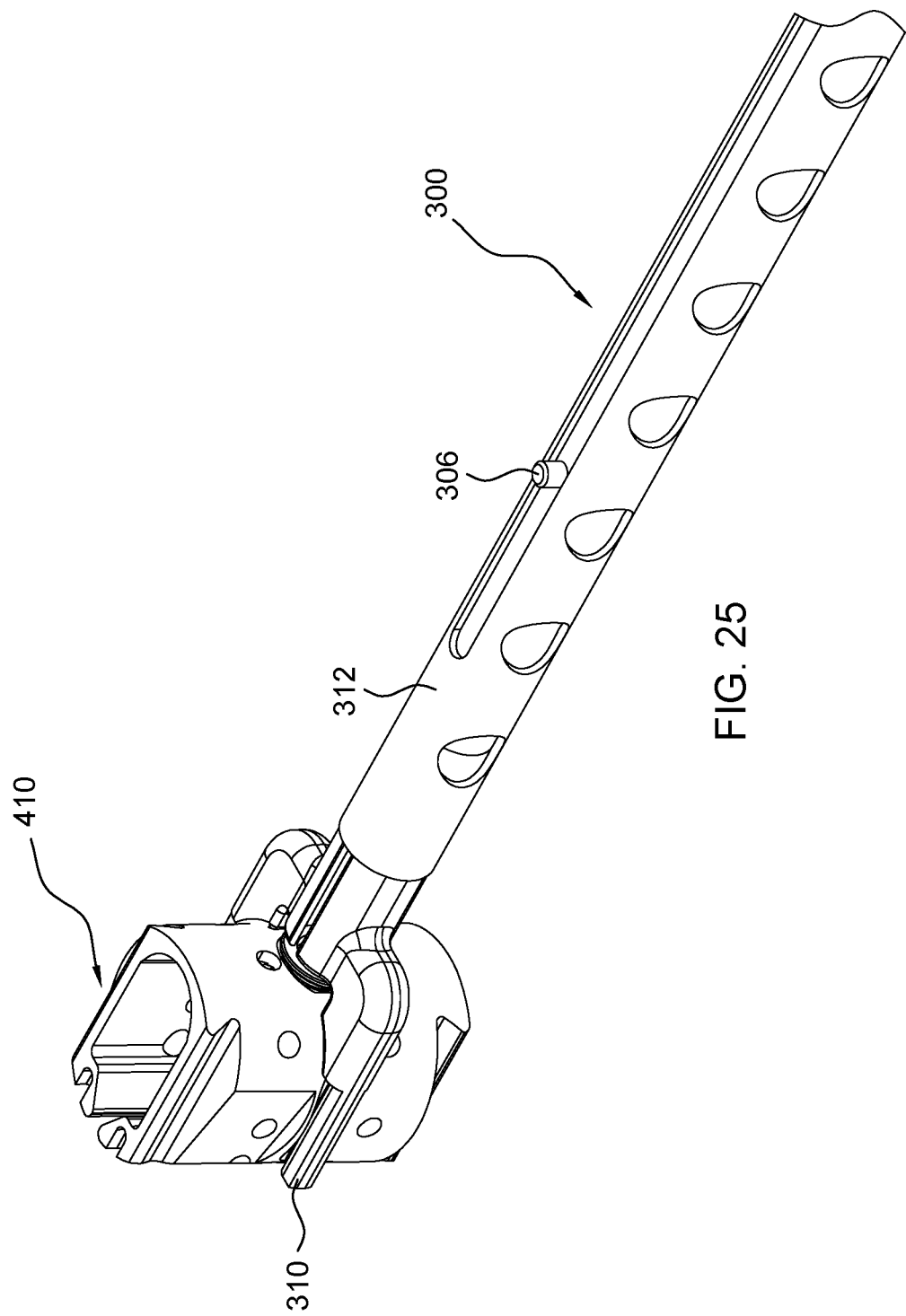
FIG. 25 is a detailed view of the proximal end of the spacer inserter of FIG. 24 with the coupled spacer, in accordance with an aspect of the present invention.
Figure 28:
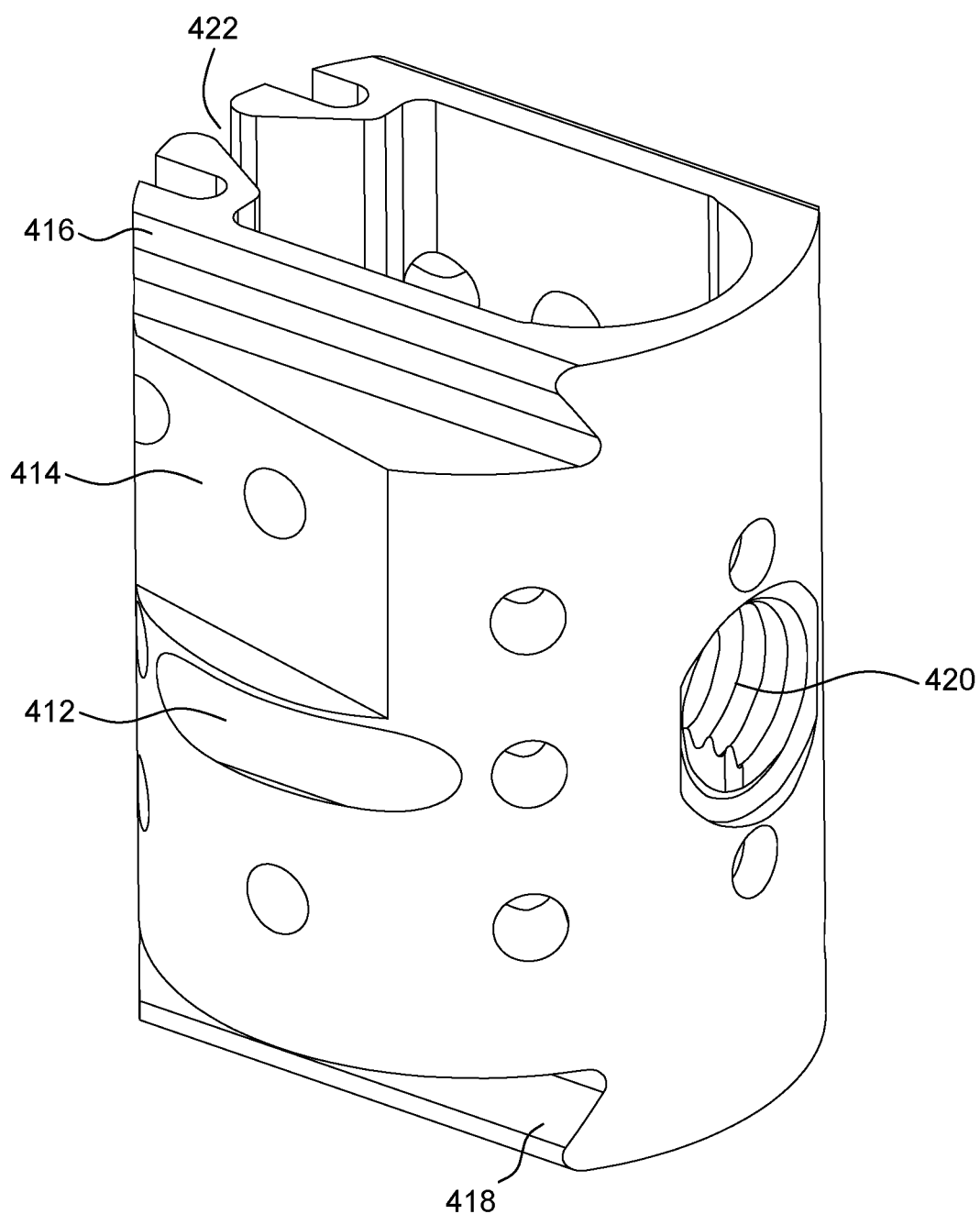
FIG. 28 is another side perspective view of the spacer of FIG. 26, in accordance with an aspect of the present invention.
Figure 37:
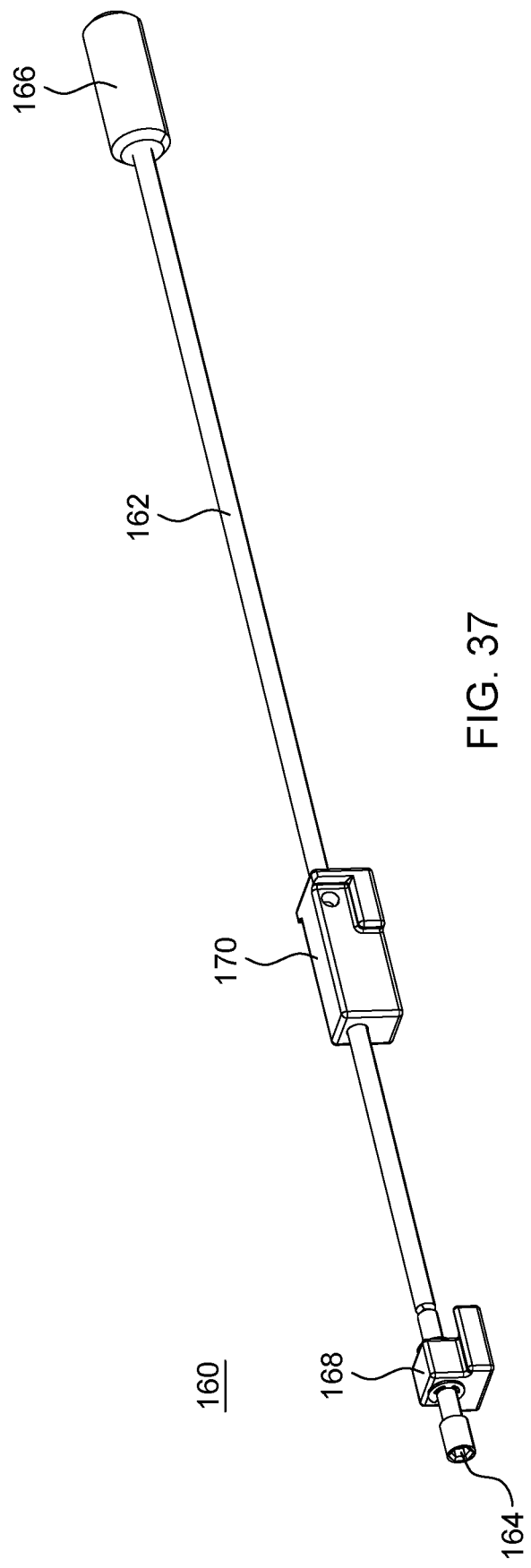
FIG. 37 is a perspective view of a first adjustment mechanism from a first end, in accordance with an aspect of the present invention.
Figure 39:
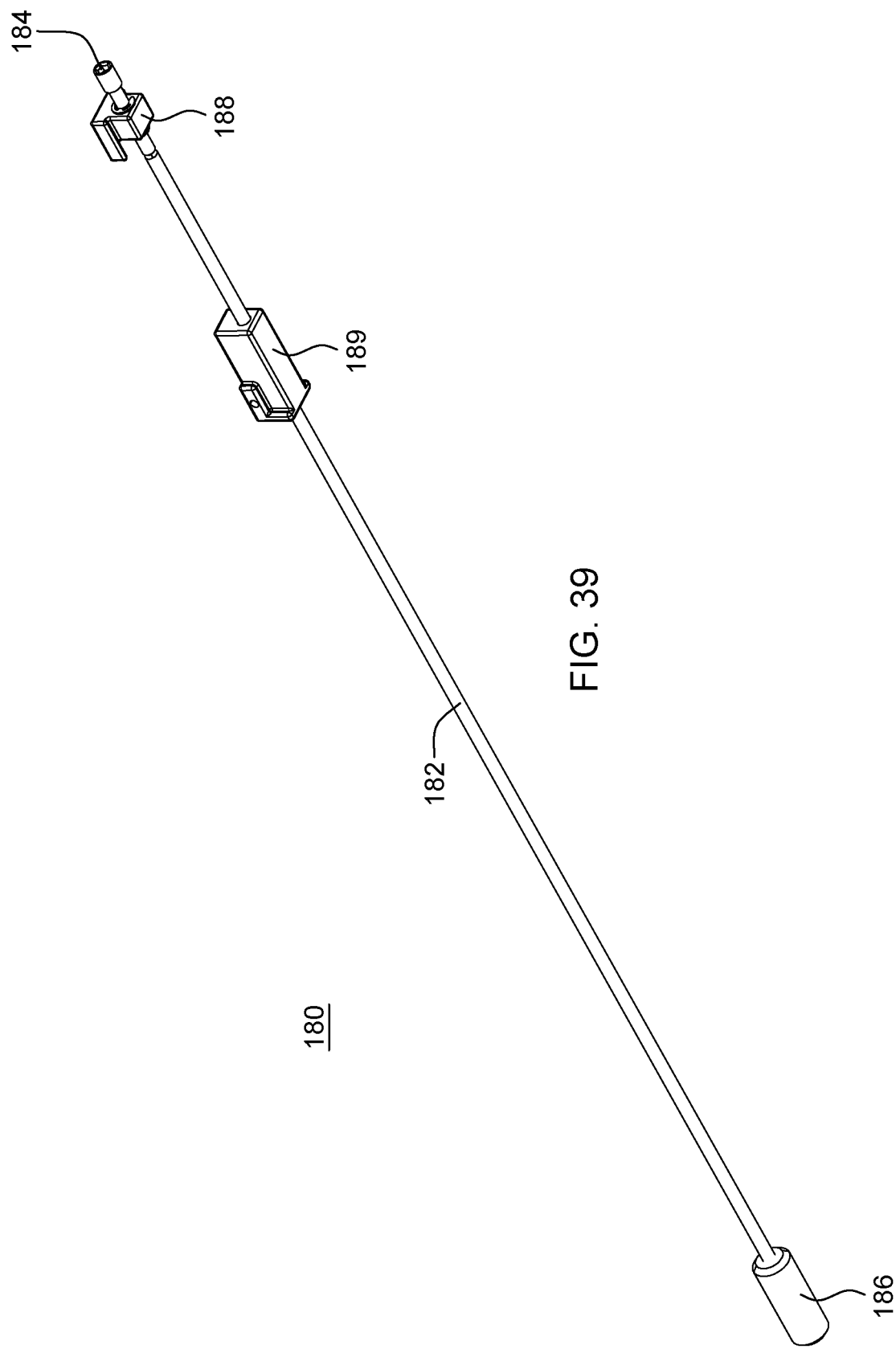
FIG. 39 is a perspective view of a second adjustment mechanism from a first end, in accordance with an aspect of the present invention.
Figure 40:
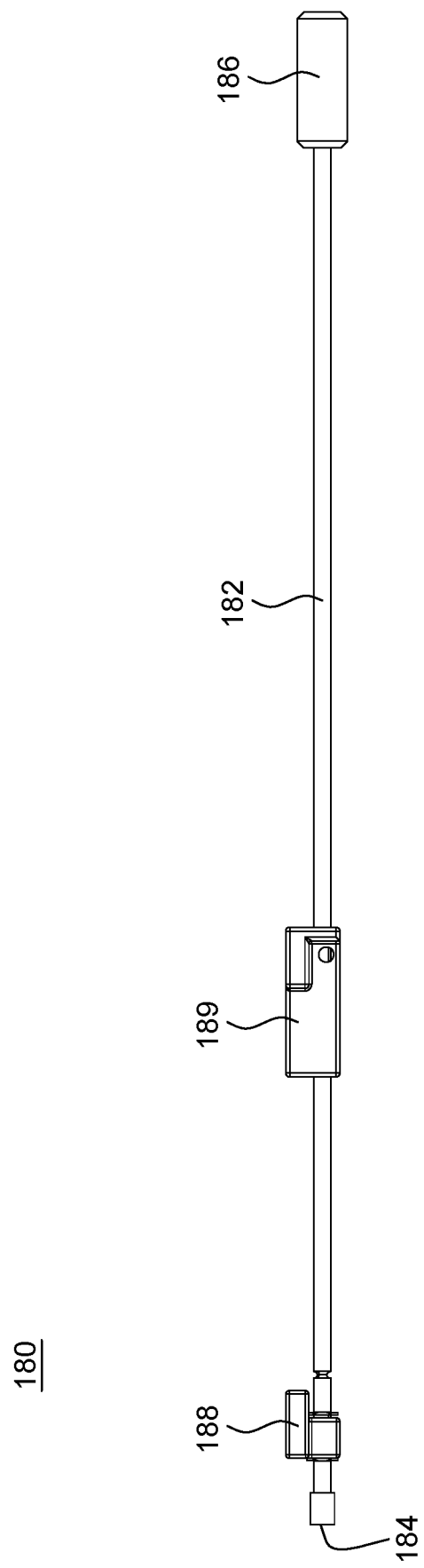
FIG. 40 is a perspective view of the second adjustment mechanism of FIG. 39 from a second end, in accordance with an aspect of the present invention.
Figure 41:
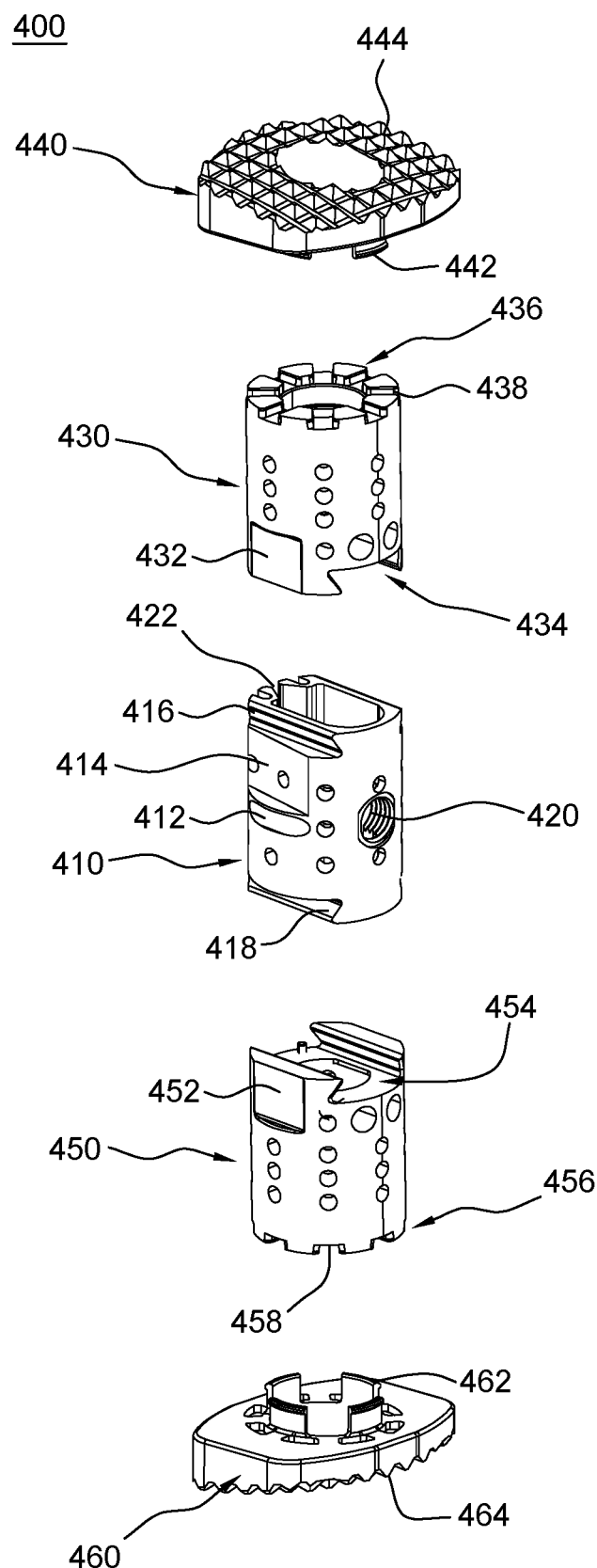
FIG. 41 is an exploded, front perspective view of a vertebral body implant, in accordance with an aspect of the present invention.
Figure 42:
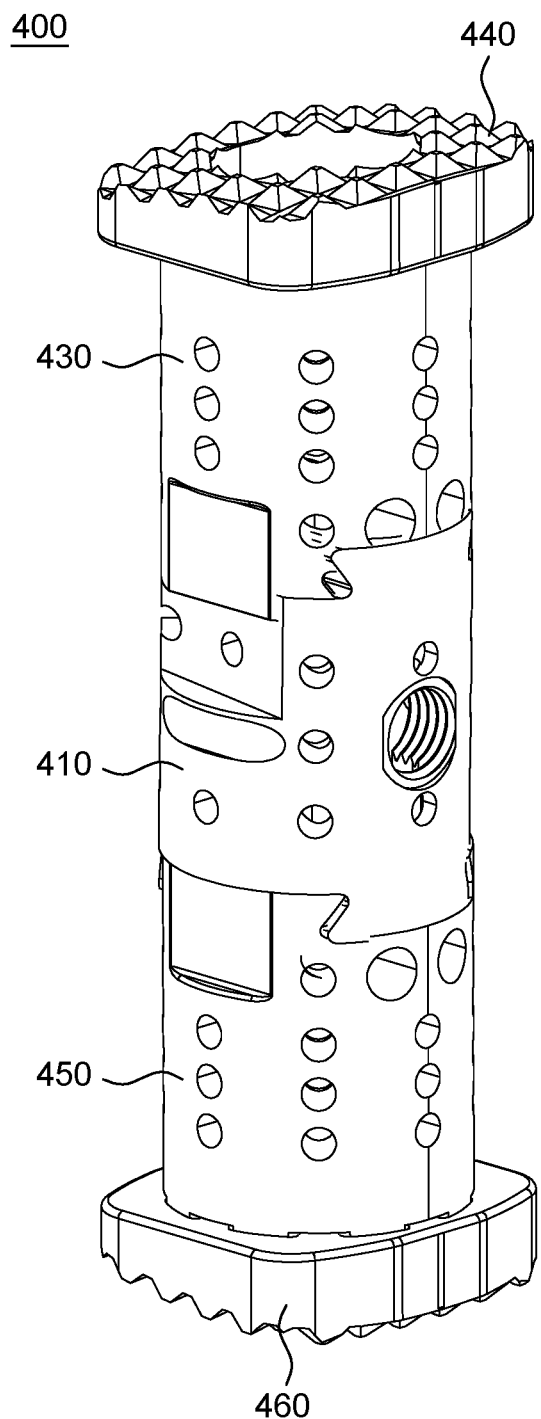
FIG. 42 is a front perspective view of the vertebral body implant of FIG. 41, in accordance with an aspect of the present invention.
Figure 43:
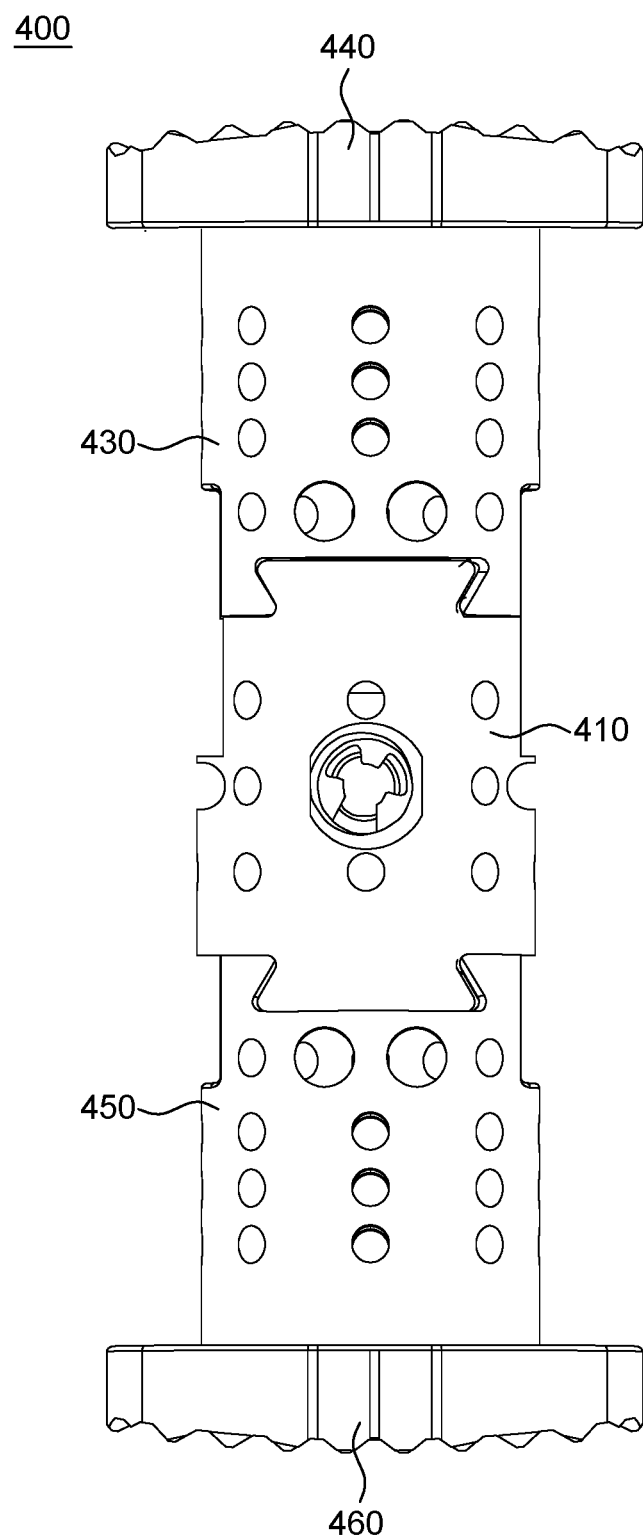
FIG. 43 is a front view of the vertebral body implant of FIG. 41, in accordance with an aspect of the present invention.
Figure 44:
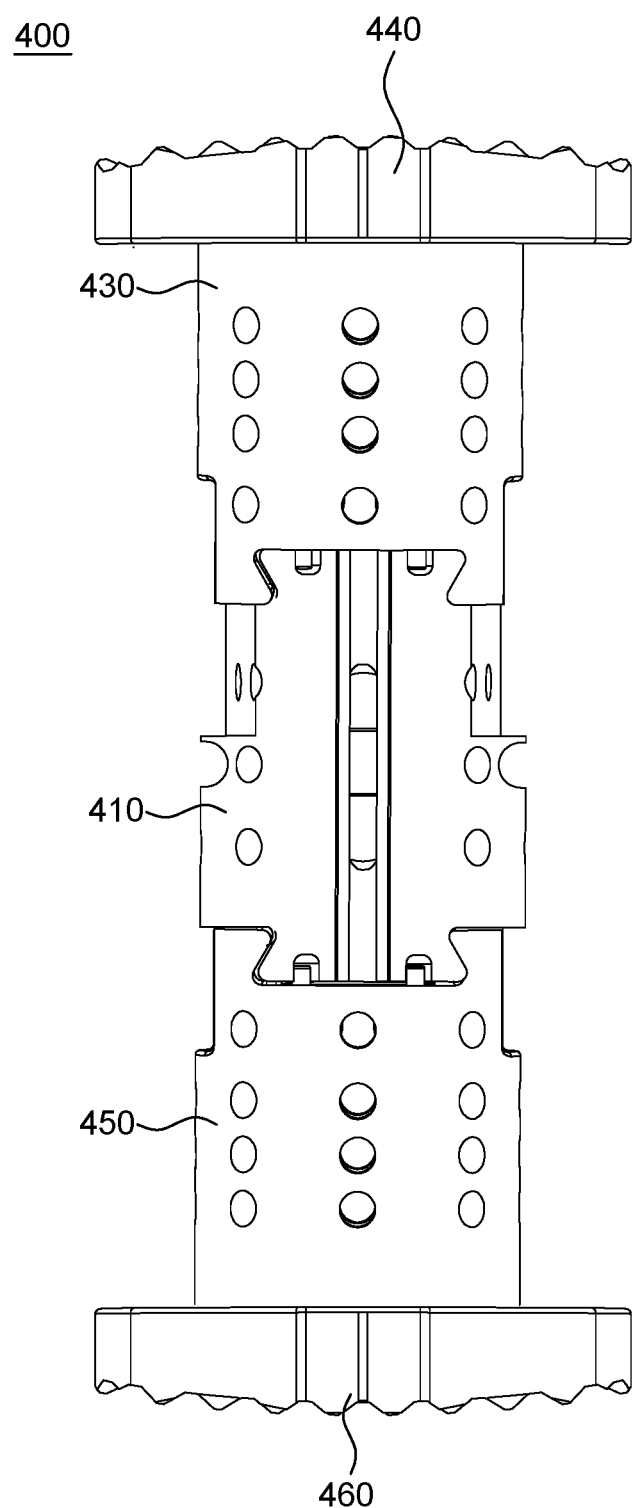
FIG. 44 is a back view of the vertebral body implant of FIG. 41, in accordance with an aspect of the present invention.
Figure 45:
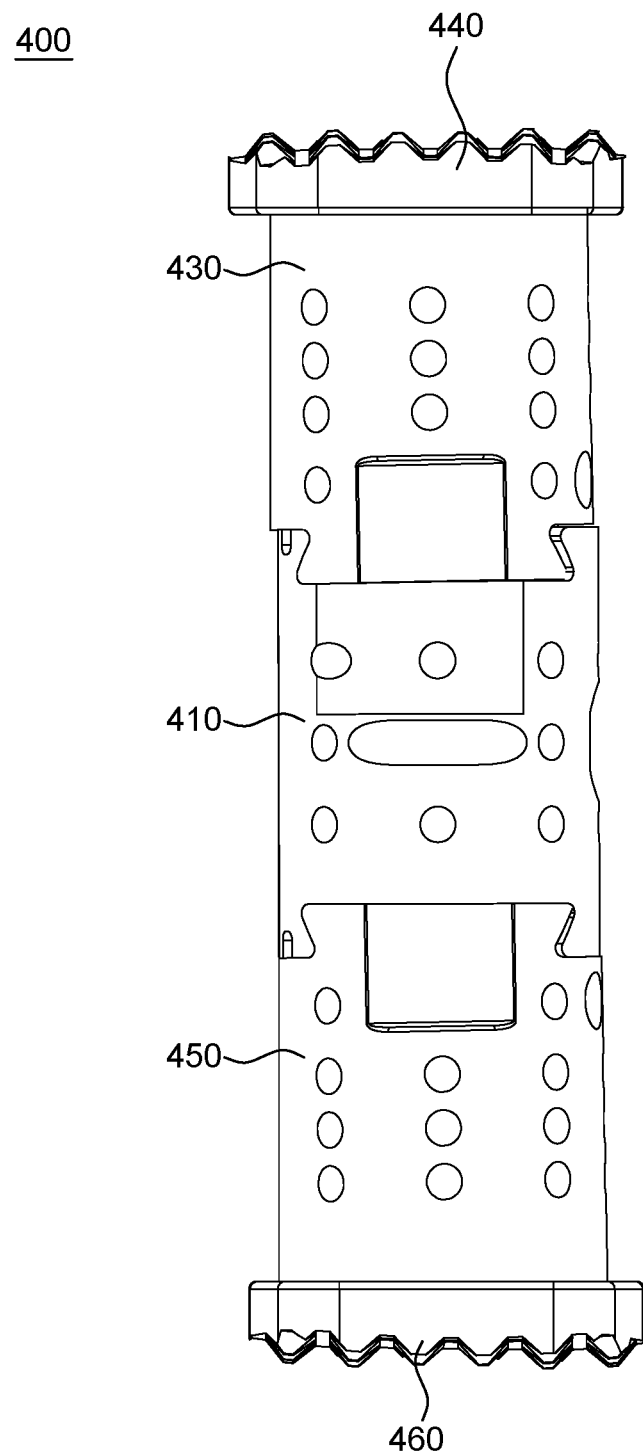
FIG. 45 is a side view of the vertebral body implant of FIG. 41, in accordance with an aspect of the present invention.
Figure 46:
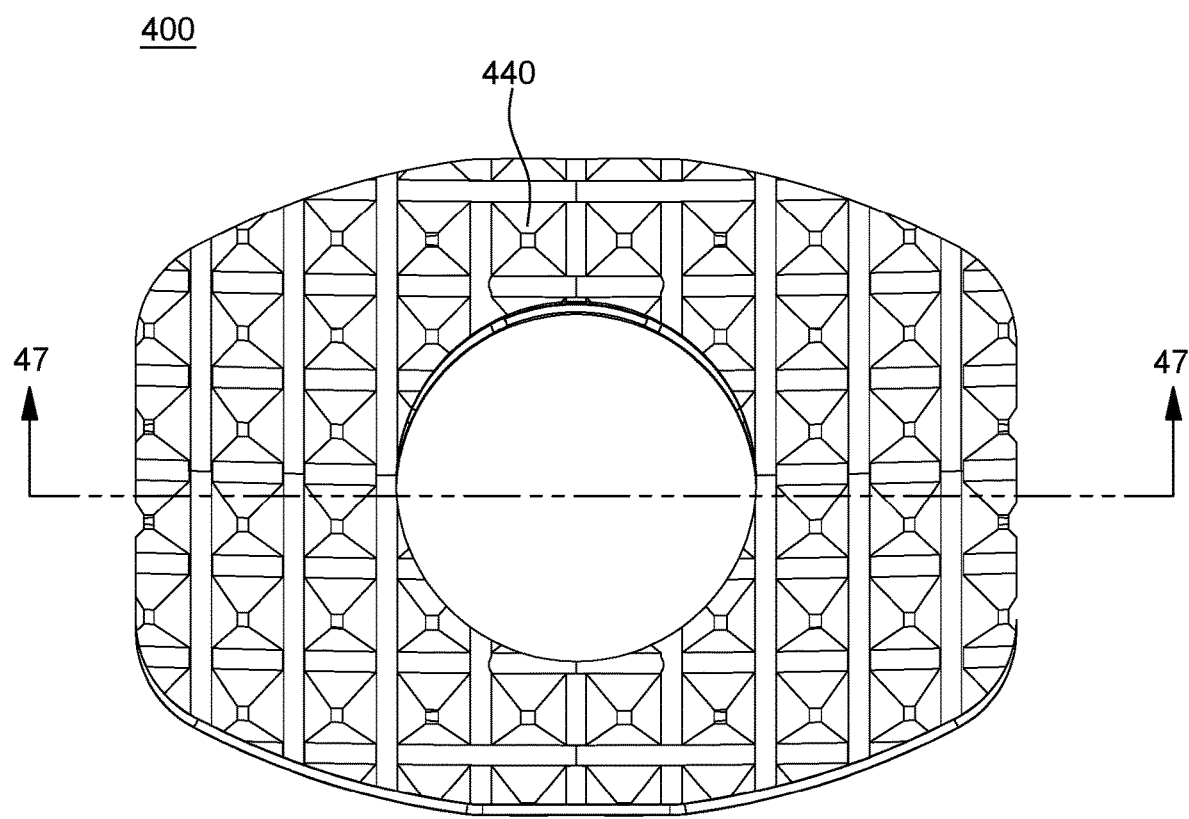
FIG. 46 is a top view of the vertebral body implant of FIG. 41, in accordance with an aspect of the present invention.
Figure 47:
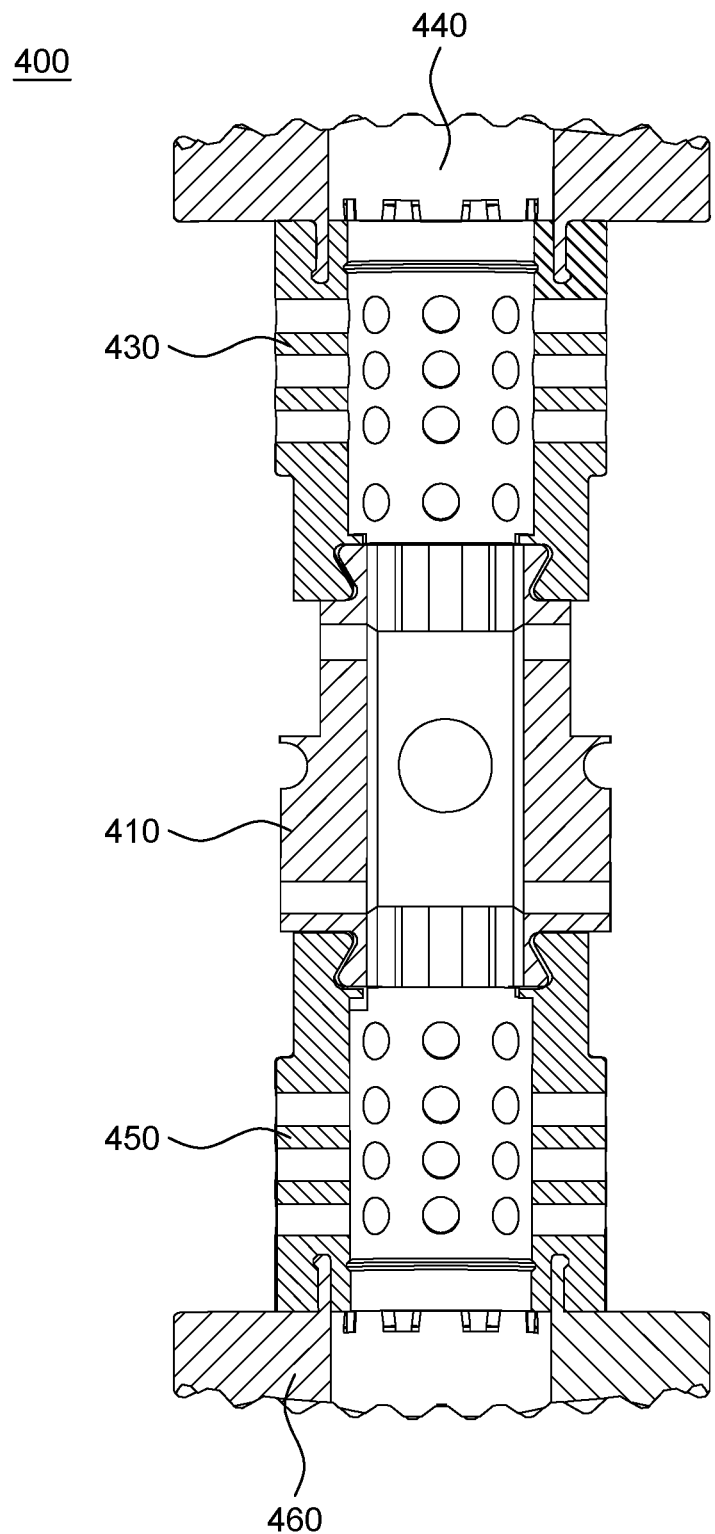
FIG. 47 is a cross sectional view of the vertebral body implant of FIG. 41 taken along line 47-47 in FIG. 46, in accordance with an aspect of the present invention.
Figure 48:
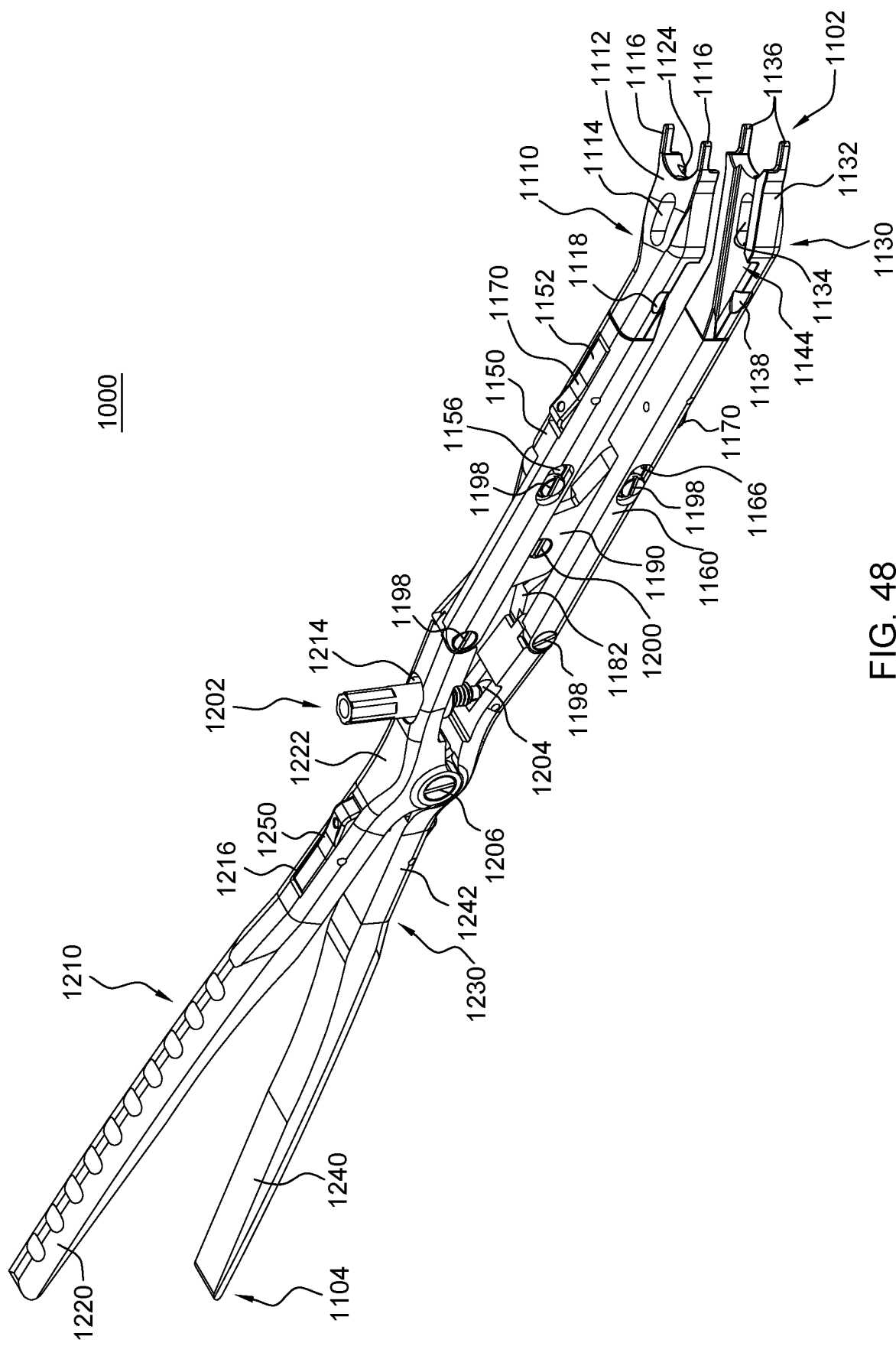
FIG. 48 is a first front perspective view of a distraction instrument of a vertebral body replacement system in an open position, in accordance with an aspect of the present invention.
Figure 49:
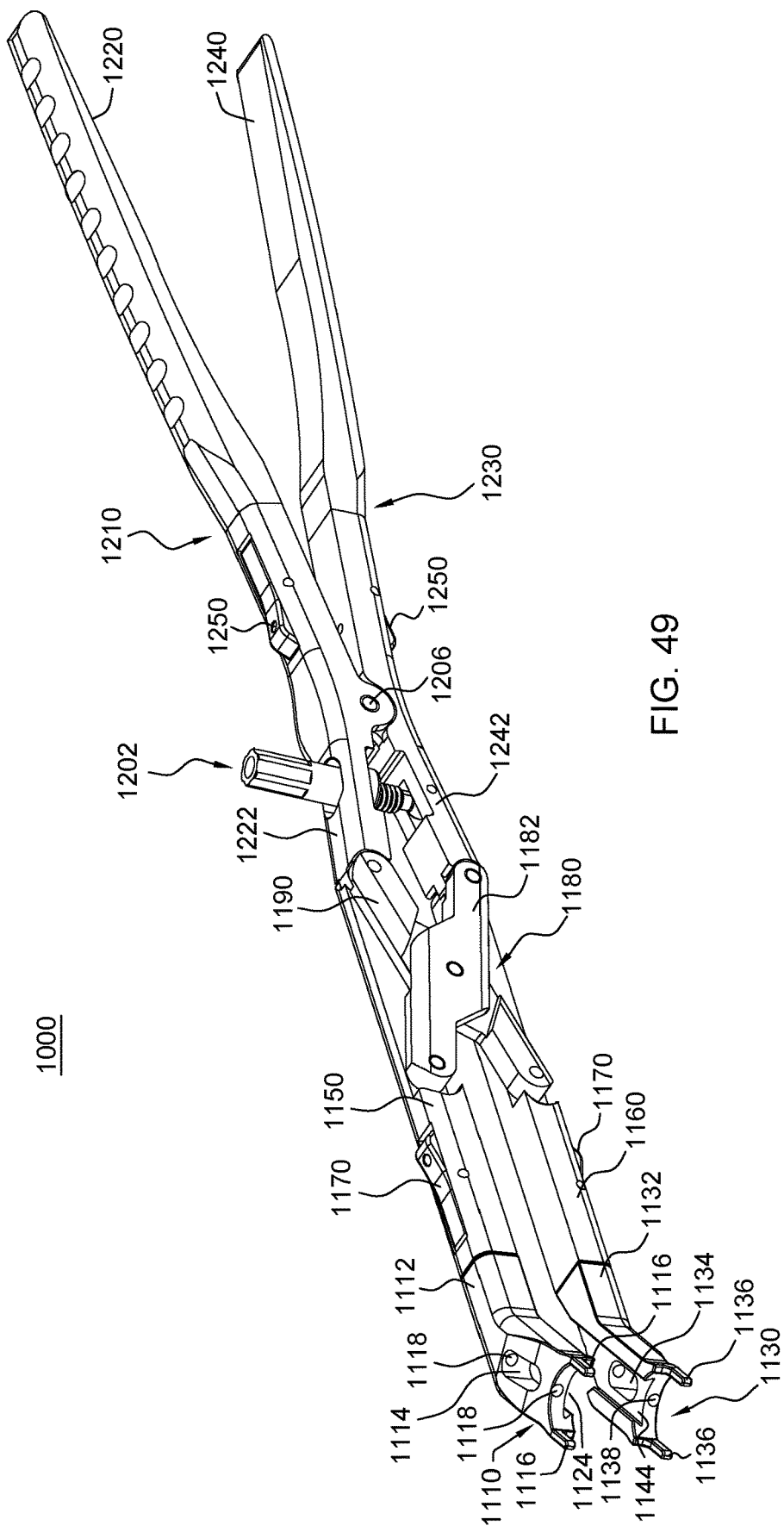
FIG. 49 is a second front perspective view of the distraction instrument of FIG. 48, in accordance with an aspect of the present invention.
Figure 50:
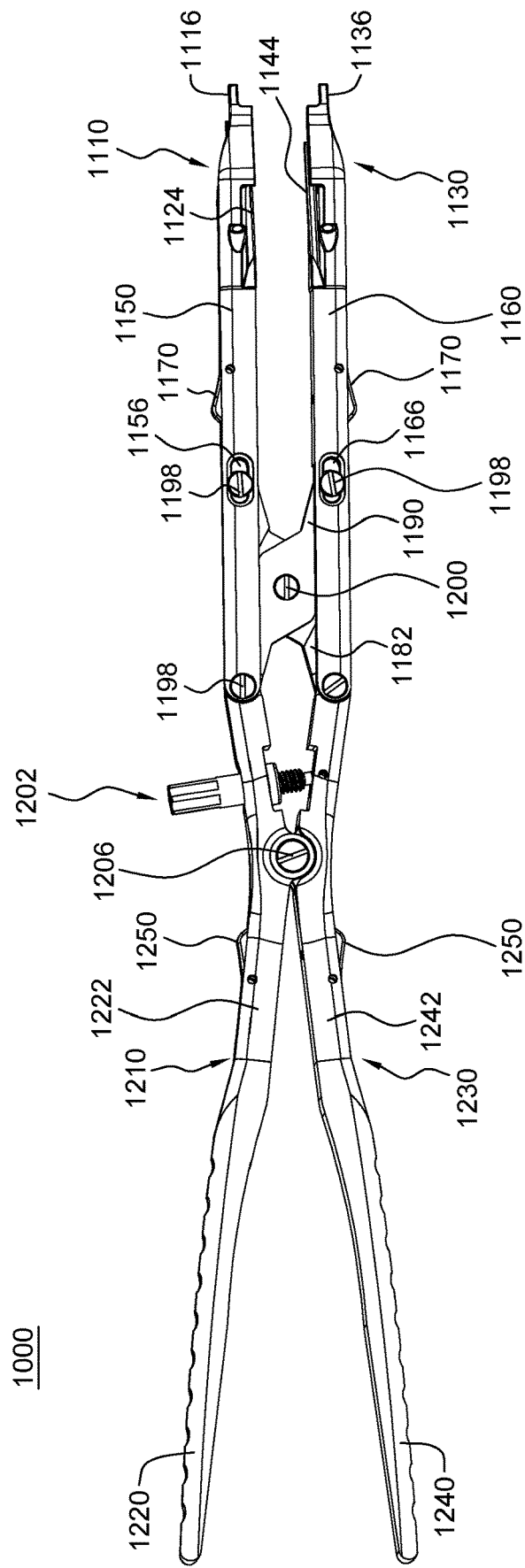
FIG. 50 is a first side view of the distraction instrument of FIG. 48, in accordance with an aspect of the present invention.
Figure 51:
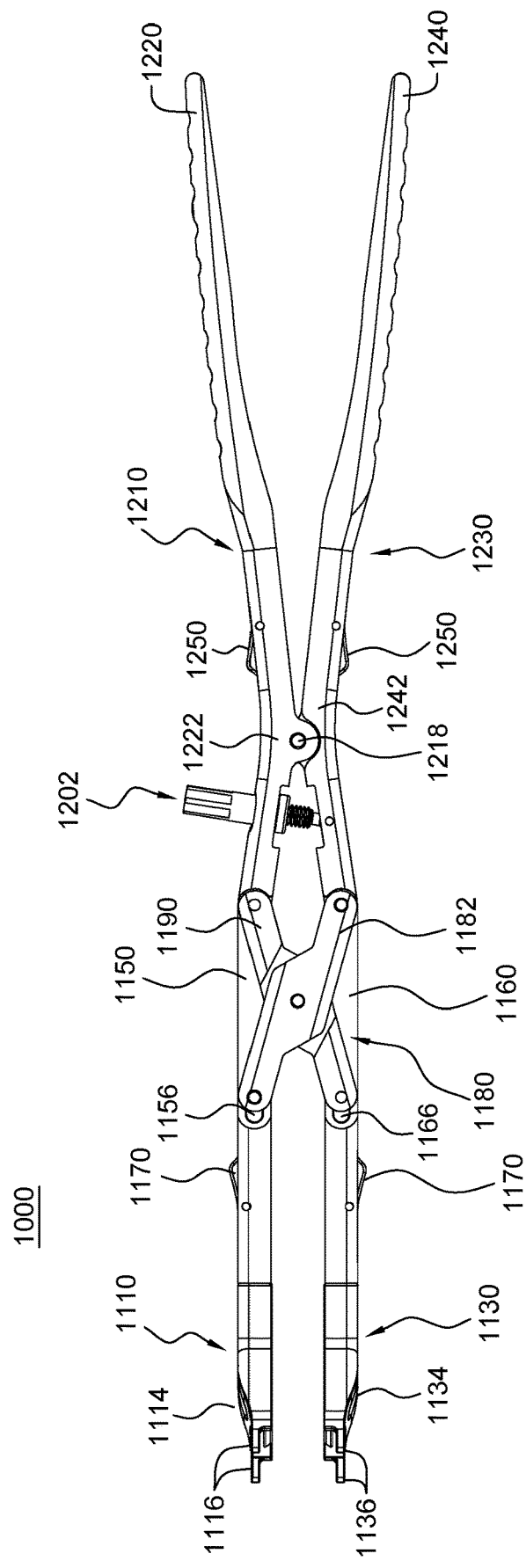
FIG. 51 is a second side view of the distraction instrument of FIG. 48, in accordance with an aspect of the present invention.
Figure 52:
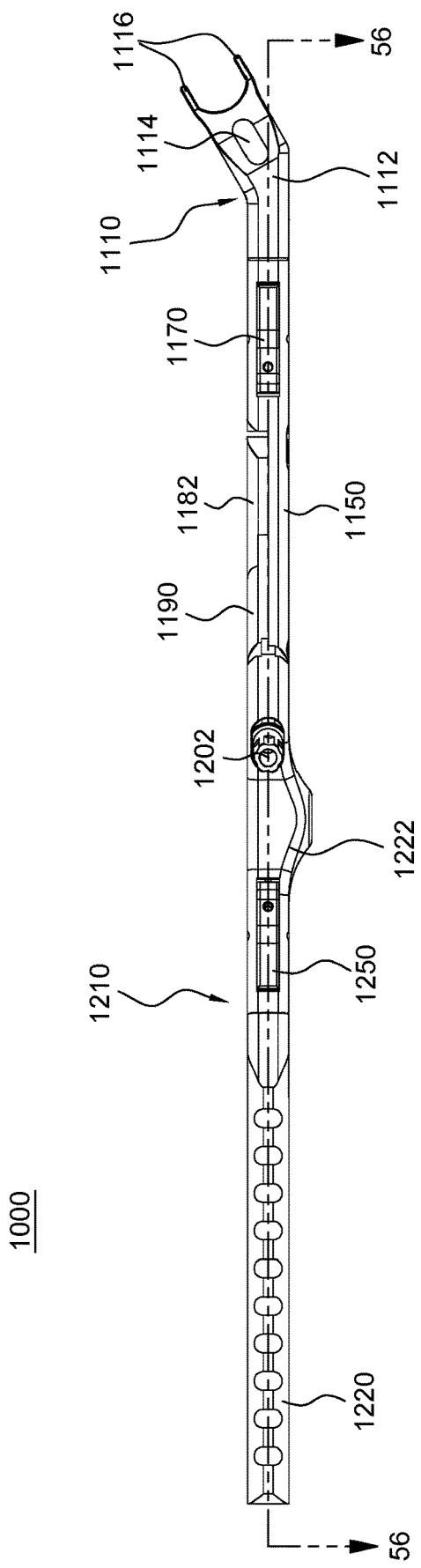
FIG. 52 is a top view of the distraction instrument of FIG. 48, in accordance with an aspect of the present invention.
Figure 53:
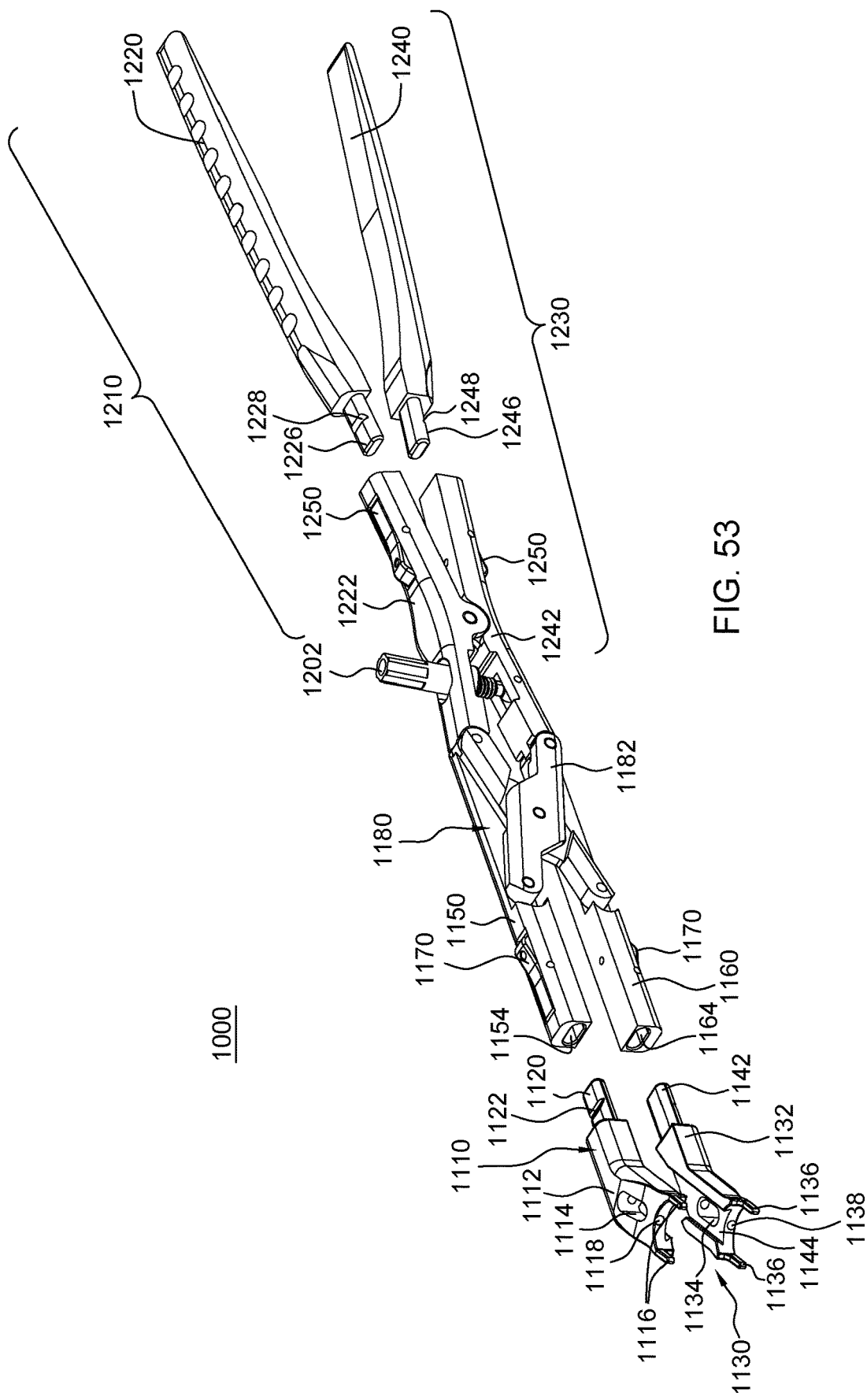
FIG. 53 is a partially exploded front perspective view of the distraction instrument of FIG. 48, in accordance with an aspect of the present invention.

Referring to the drawings, wherein like reference numerals are used to indicate like or analogous components throughout the several views, there is illustrated a spinal spacer assembly or vertebral body replacement instrument assembly. The assembly includes a distraction instrument 100, as shown in FIGS. 1-11 and 14-16, an expander mechanism 200, as shown in FIGS. 17-21, a spacer inserter 300, as shown in FIGS. 23-25, a first adjustment mechanism 160, as shown in FIGS. 37-28, and a second adjustment mechanism 180, as shown in FIGS. 39-40.

The distraction instrument 100, as shown in FIGS. 1-11, 14-16, 22, 30-31, and 34-36, may include a body 102, a first elongate member 110, a second elongate member 120, a distraction system 130, a movement system 140, a handle 104, and a trigger 106. The first elongate member 110 may be coupled to a first end of the body 102 at a second end and include an engagement portion 112 at the first end. The distraction system 130 may movably couple the second elongate member 120 to the first elongate member 110. The first and second elongate members 110, 120 may be positioned, for example, generally parallel to each other. The second elongate member 120 may be coupled to the distraction system 130 at a second end and include an engagement portion 122 at the first end.

The distraction system 130 may include two first links 132 and two second links 134. One first link 132 and one second link 134 may be pivotally coupled together and pivotally attached to the first and second elongate members 110, 120 on a first side. The other first link 132 and the other second link 134 may be pivotally coupled together and pivotally attached to the first and second elongate members 110, 120 on a second side. The first links 132 may be attached to the first elongate member 110 at a first end and slidingly coupled to the channel 124 in the second elongate member 120 at a second end. The second links 134 may be attached to the second elongate member 120 at a first end and slidingly coupled to the channel 114 in the first elongate member 110 at a second end. The first and second links 132, 134 may be coupled to each other and the elongate members 110, 120 by at least one fastener 136. The fasteners 136 may be, for example, screws, rivets, pins, or the like that allow for the links 132, 134 to be pivotally coupled to each other and the elongate members 110, 120.

Figure 1:
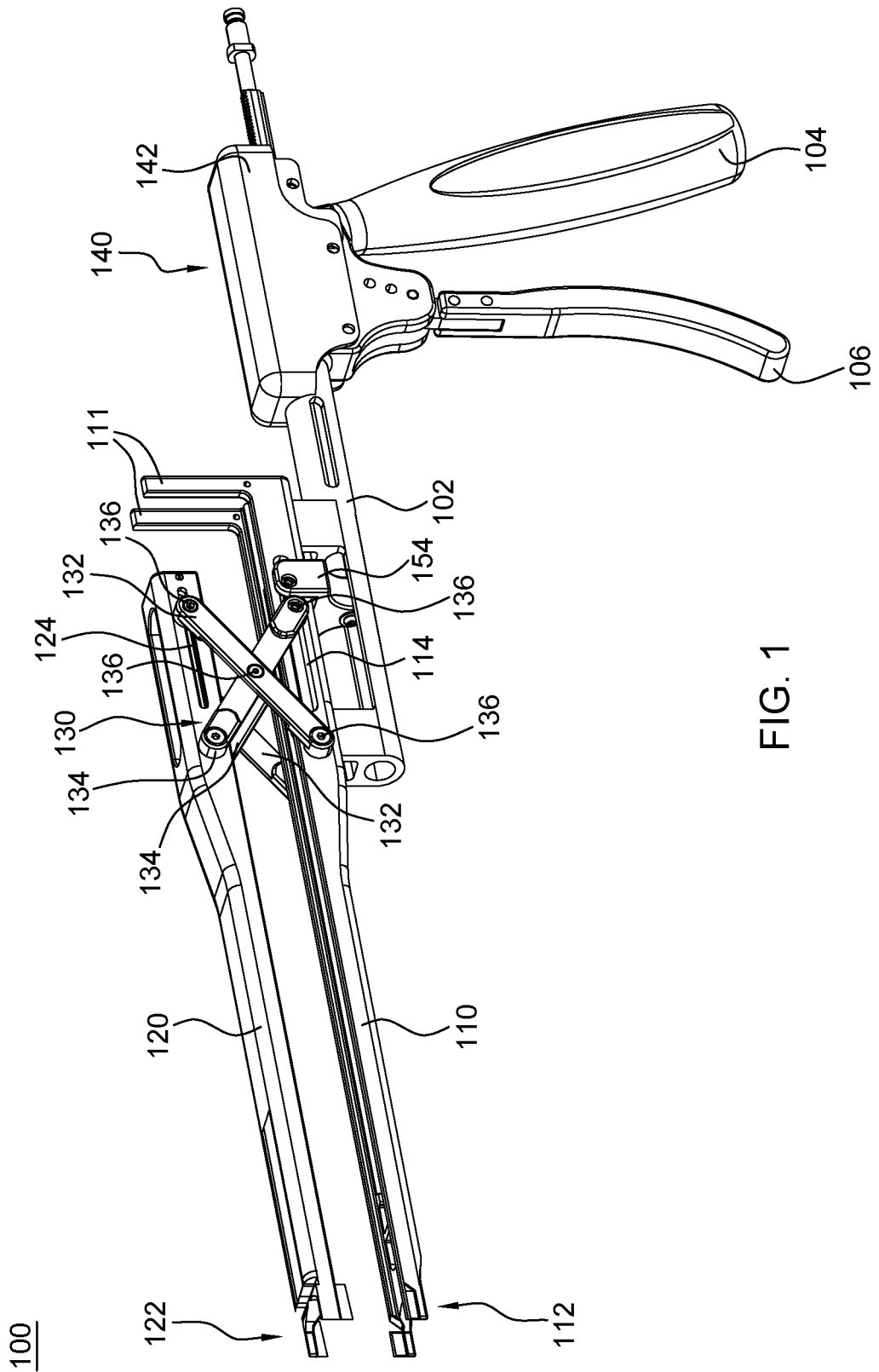
FIG. 1 is a perspective view of a distraction instrument of a vertebral body replacement instrument in an open position, in accordance with an aspect of the present invention.
Figure 2:
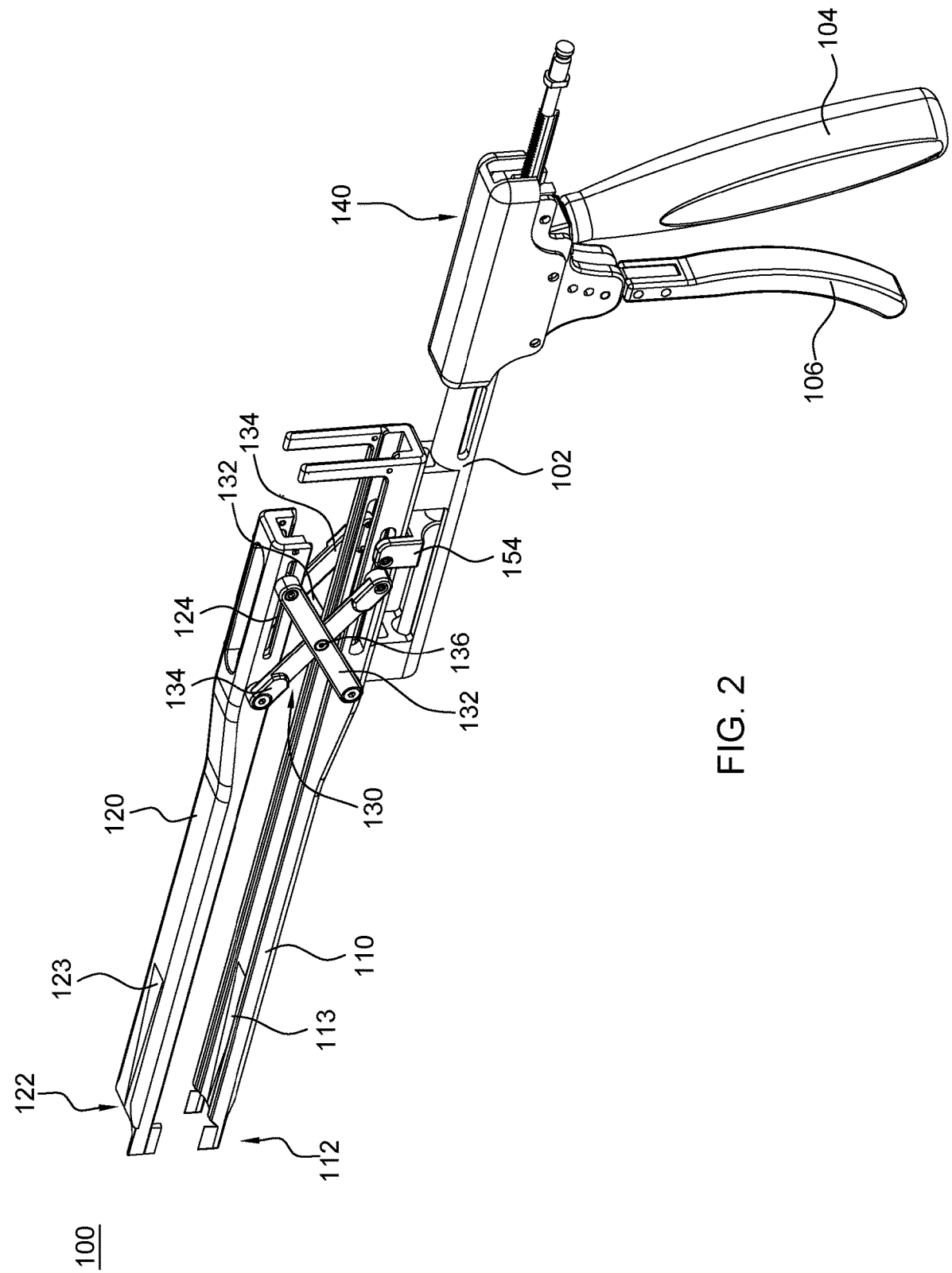
FIG. 2 is a rear, perspective view of the distraction instrument of FIG. 1, in accordance with an aspect of the present invention.
Figure 3:
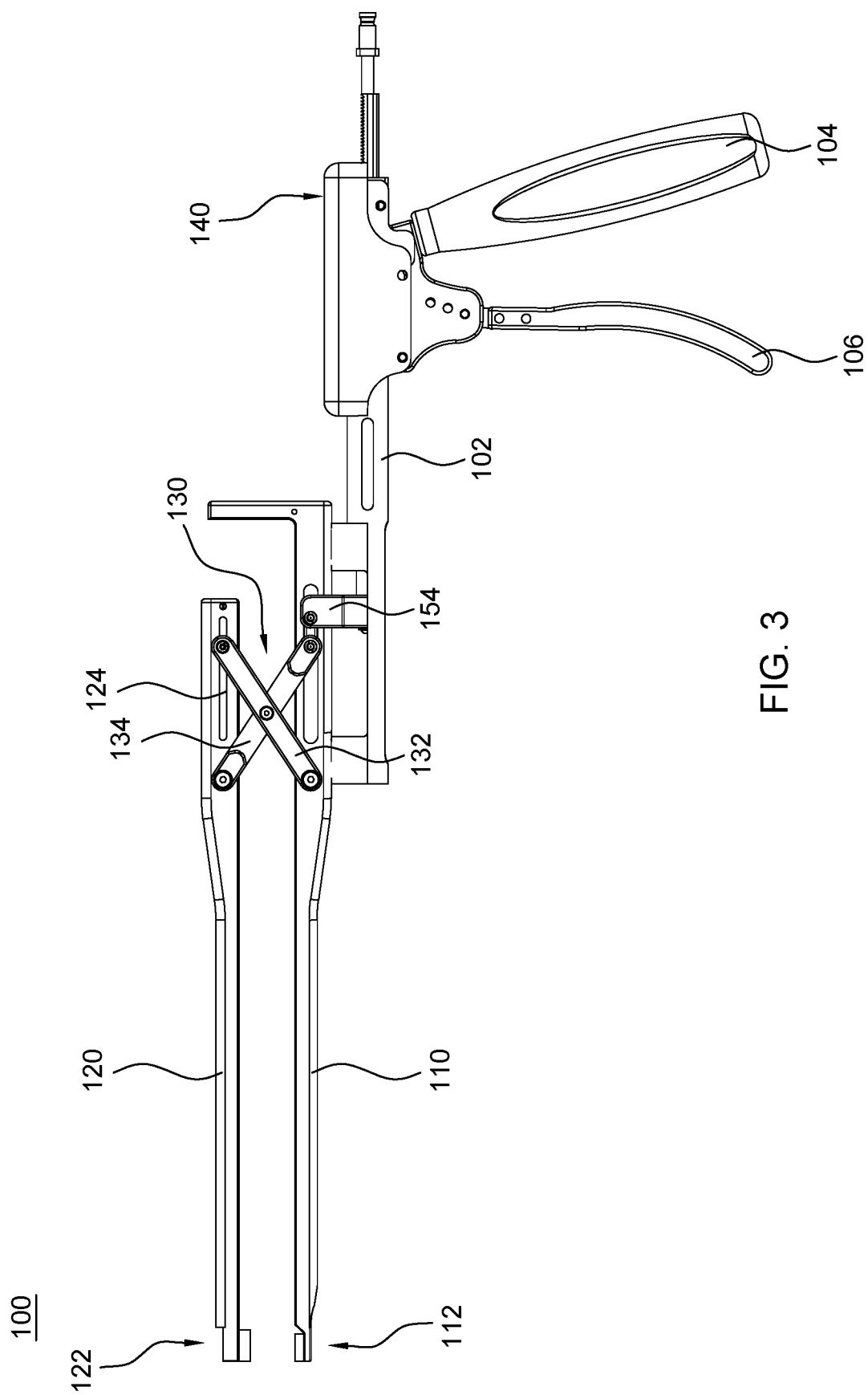
FIG. 3 is a side view of the distraction instrument of FIG. 1, in accordance with an aspect of the present invention.
Figure 4:
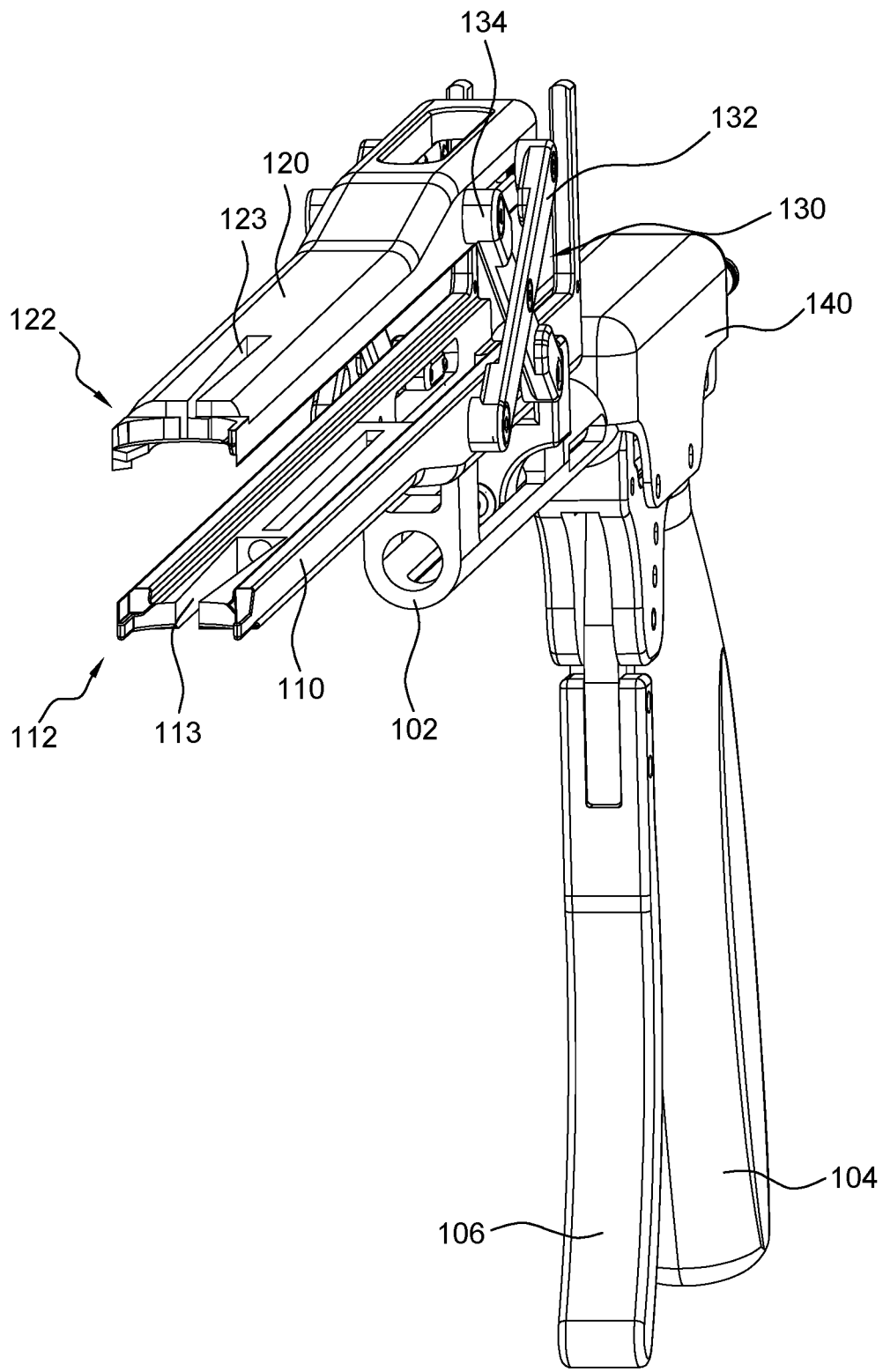
FIG. 4 is a front, perspective view of the distraction instrument of FIG. 1, in accordance with an aspect of the present invention.
Figure 5:
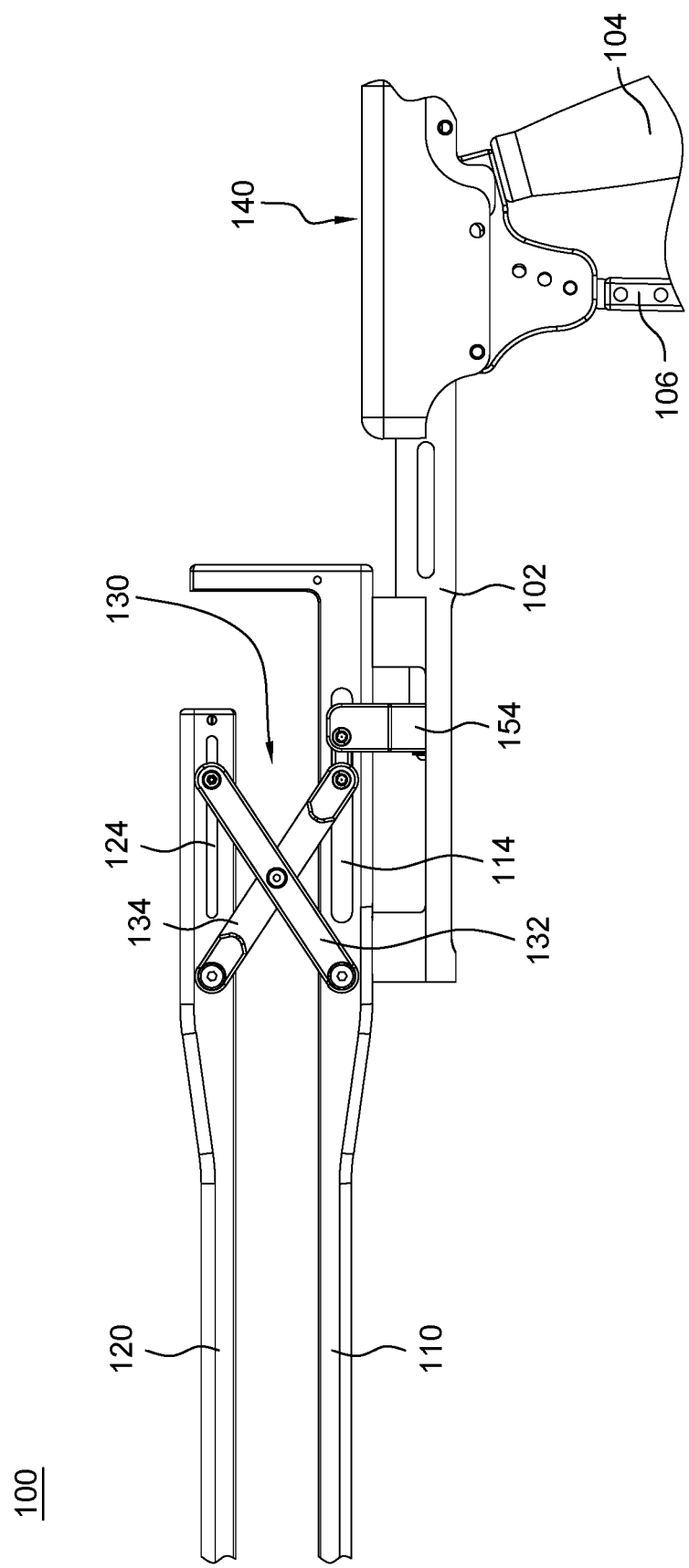
FIG. 5 is a side view of a portion of the distraction instrument of FIG. 1 showing the expansion system, in accordance with an aspect of the present invention.
Figure 6:
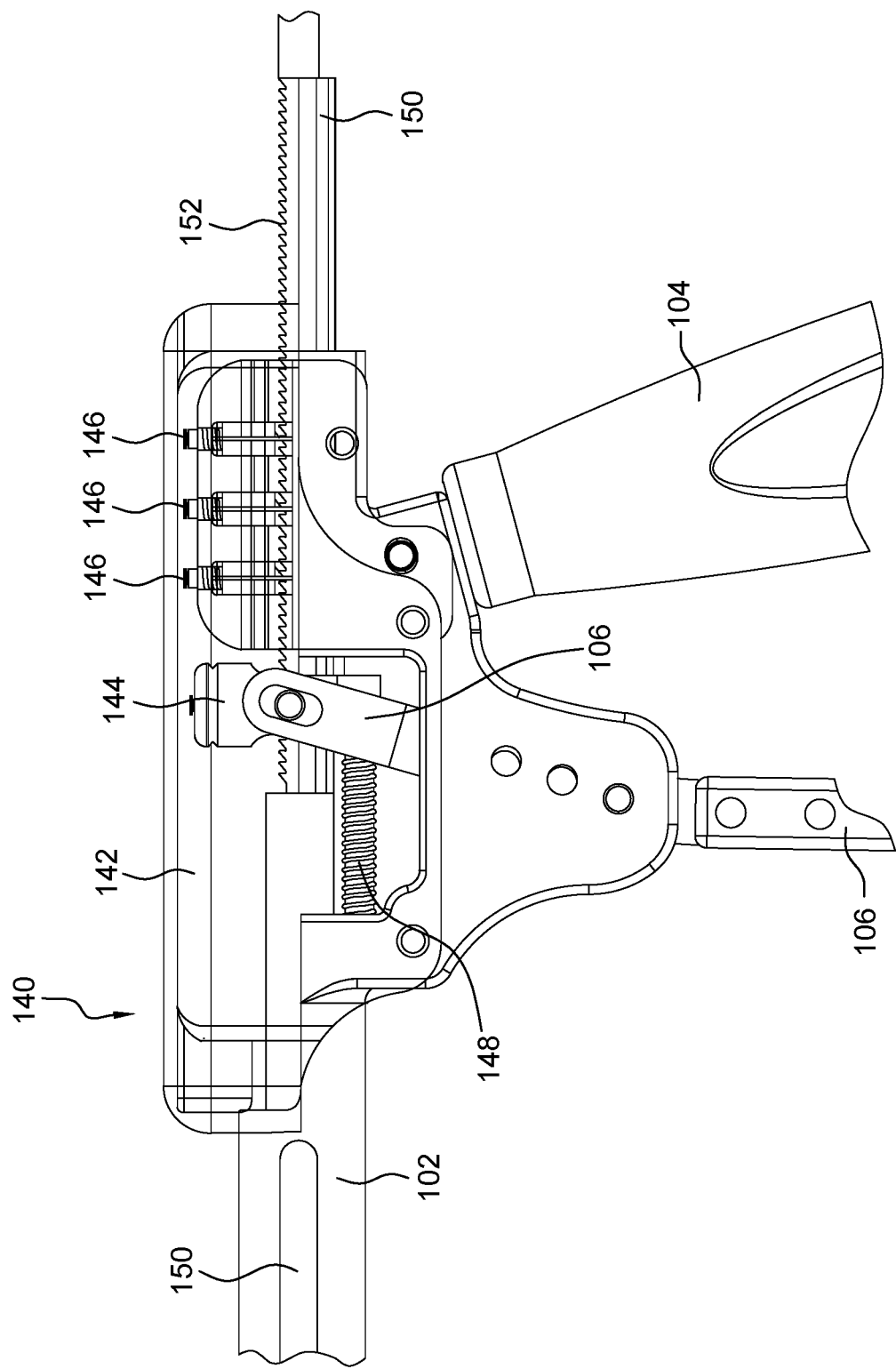
FIG. 6 is a side view of a portion of the distraction instrument of FIG. 1 with a transparent cover to show the ratcheting system, in accordance with an aspect of the present invention.
Figure 14:
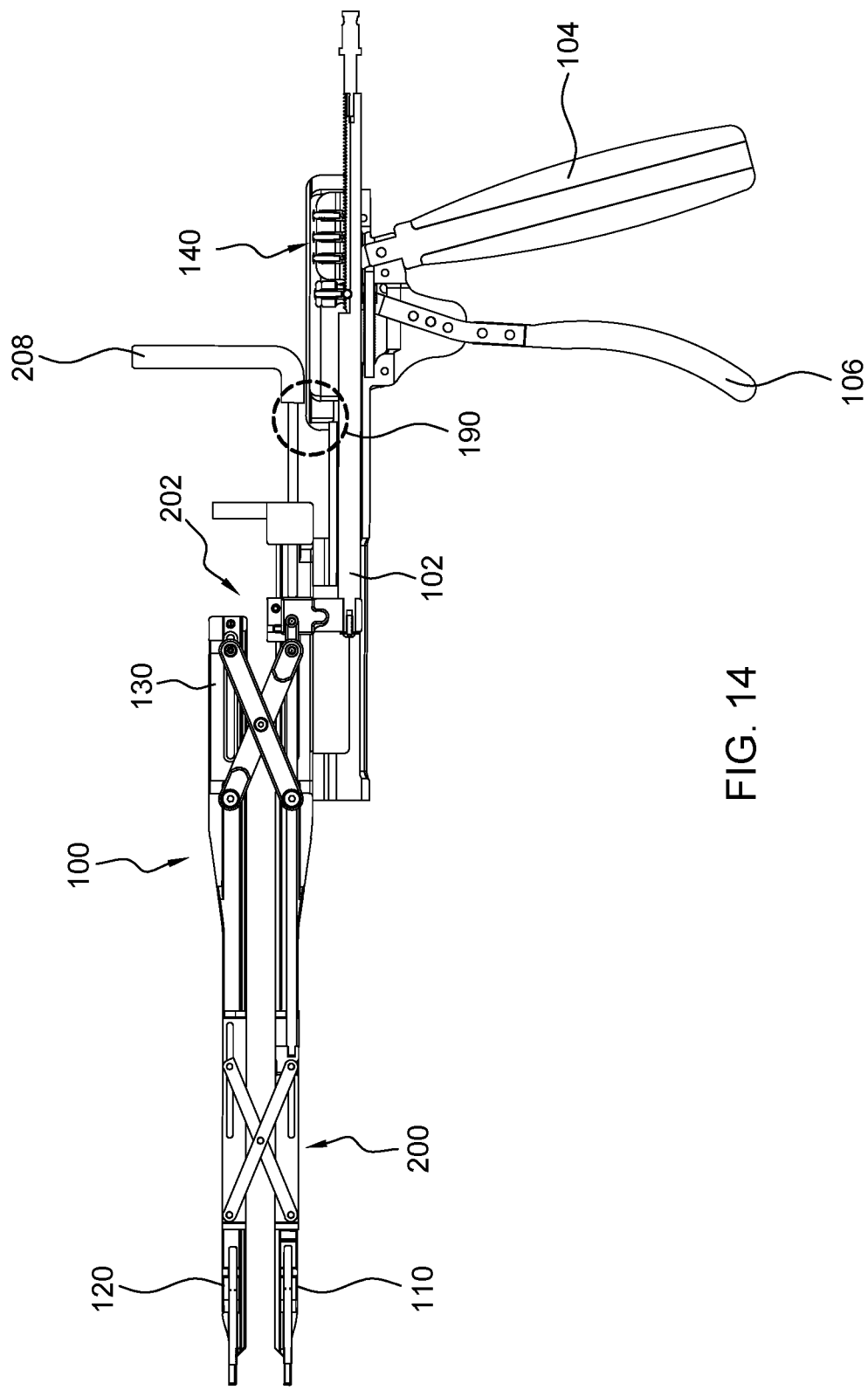
FIG. 14 is a side view of the distraction instrument of FIG. 1 with an expander mechanism inserted into the distraction instrument, in accordance with an aspect of the present invention.

With continued reference to FIGS. 1-11, 14-16, 22, 30-31, and 34-36, the handle 104 and trigger 106 may be secured to a bottom side of the body 102 at a second end. The movement system 140 may be coupled to a top side of the body 102 at the second end. The movement system 140 may include a cover 142 positioned over a drive mechanism 144 and at least one locking mechanism 146, as shown in FIGS. 6 and 14. The drive mechanism 144 may be coupled to the trigger 106 to allow for movement of the trigger 106 to actuate the drive mechanism 144. As the drive mechanism 144 is actuated, the drive mechanism 144 may move the distraction system 130 to expand the space between the first and second elongate members 110, 120. The movement system 140 may also include a spring 148 that engages the trigger 106 to move the trigger 106 back to a resting or starting position after release by a user. The movement system 140 may further include a translating member 150. The translating member 150 may be positioned within the body 102 and moveably engage the drive mechanism 144 to move the first elongate member 110. The translating member 150 may include teeth 152 along at least a portion of the translating member 150. As the drive mechanism 144 is activated, the drive mechanism 144 engages the teeth 152 of the translating member 150 to move the translating member 150 toward a proximal end of the distraction instrument 100. The translating member 150 may also include a slide mechanism 154 coupled to a first end of the translating member 150, such that as the translating member 150 is moved forward by the drive mechanism 144 the slide mechanism 154 also move forward. The slide mechanism 154 may be positioned within the channel 114 and engage the links 132, 134 of the distraction system 130 to move the links 132, 134 proximally to separate the first and second elongate members 110, 120.

Figure 7:
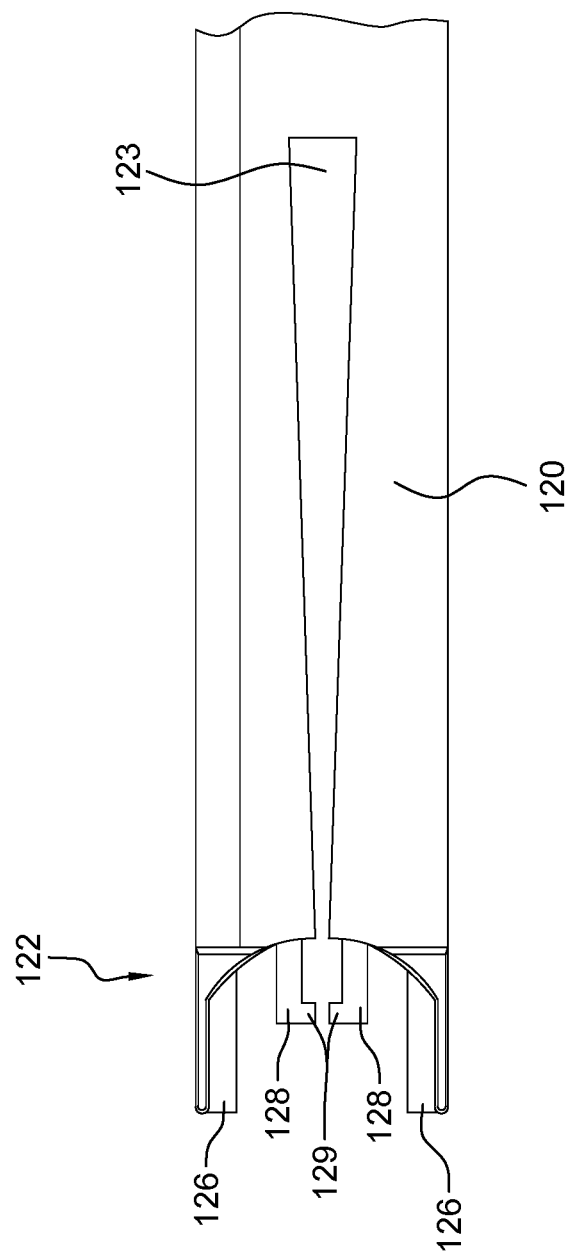
FIG. 7 is a top view of a connector portion of the distraction instrument of FIG. 1, in accordance with an aspect of the present invention.
Figure 8:
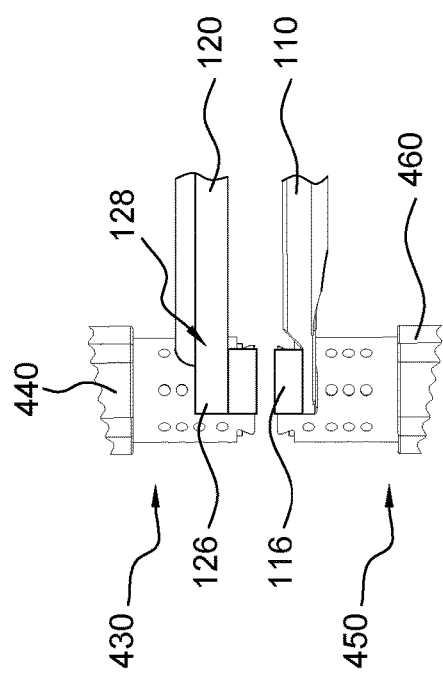
FIG. 8 is a side view of a portion of the distraction instrument of FIG. 1 engaging a first member and second member of a vertebral body implant, in accordance with an aspect of the present invention.
Figure 9:
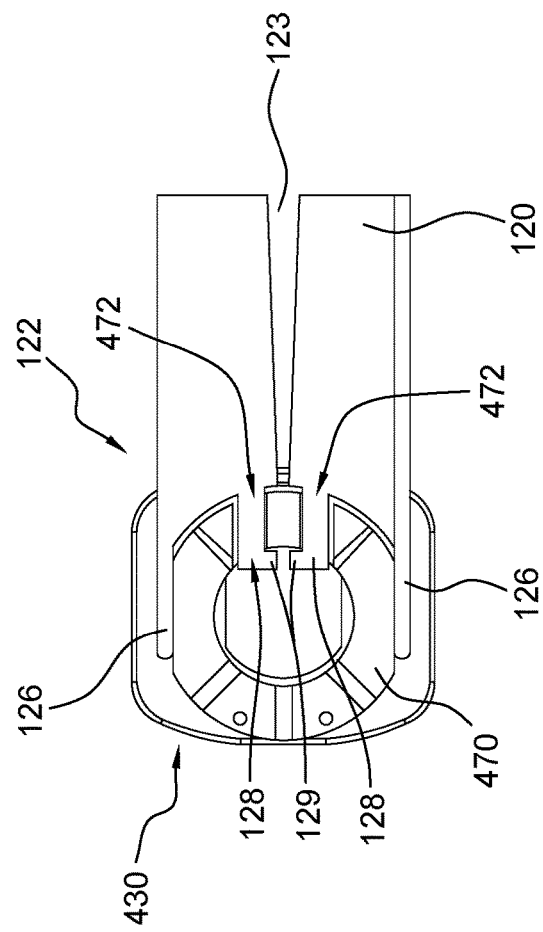
FIG. 9 is a top view of the distraction instrument and first member of FIG. 8, in accordance with an aspect of the present invention.

Referring now to FIGS. 7-9, the second elongate member 120 may, for example, include an opening 123 extending from the first end into a portion of the elongate member 120 toward the second end. The engagement portion 122 of the second elongate member 120 may include protrusions 126 extending out from the lateral edges of the elongate member 120 to couple to an exterior surface of an implant 400. The engagement portion 122 may also include gripping members 128 extending out from a center portion of the elongate member 120 between the protrusions 126. The gripping members 128 may each include a tooth or other like protrusion or pin 129 extending toward each other. The gripping members 128 may be positioned on either side of the opening 123. The opening 123 may be, for example, generally triangularly shaped to allow for movement of the gripping members 128 of the engagement portion 122. As shown in FIG. 9, the gripping members 128 may each be inserted into an opening 472 in the coupling portion 470 of one embodiment of the first member 430 of implant 400. The protrusions 126 of the engagement portion 122 may be positioned on the sides of the coupling portion 470 to provide additional support to the first member 430 during distraction of a patient's vertebrae.

Figure 11:
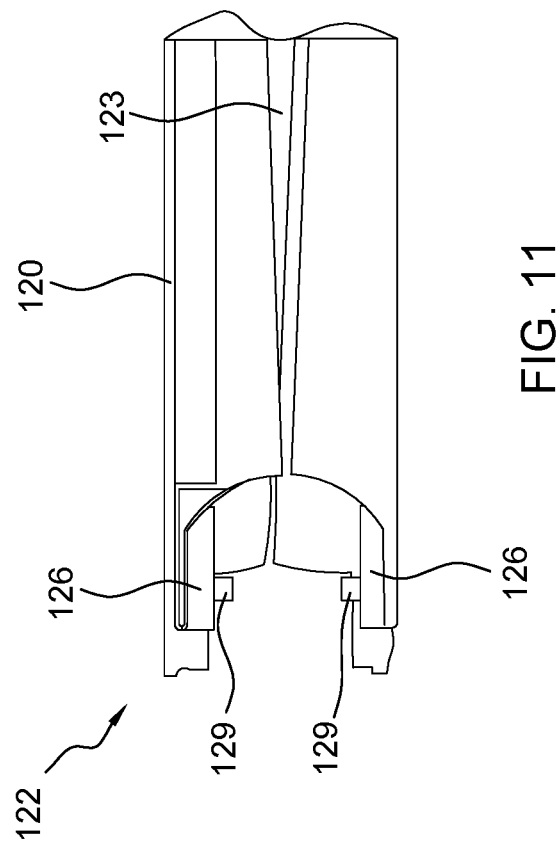
FIG. 11 is a top view of an elongate connector member of the distraction instrument of FIG. 10, in accordance with an aspect of the present invention.
Figure 10:
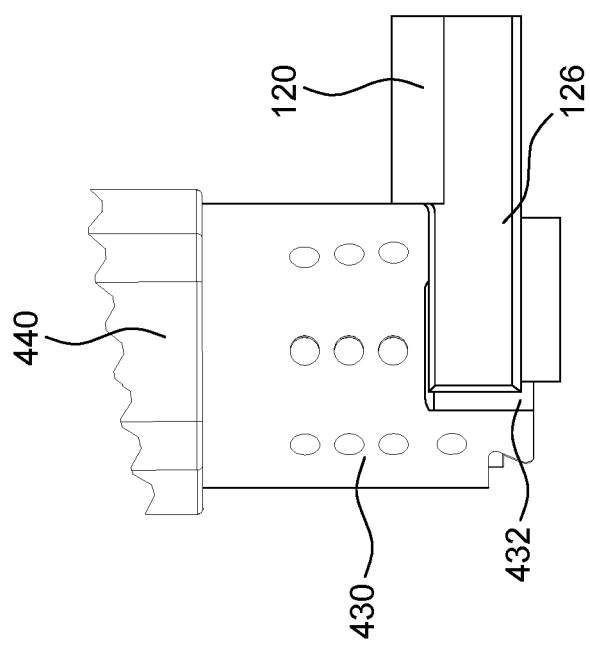
FIG. 10 is a side view of another embodiment of the distraction instrument of FIG. 1 engaging a first member of a vertebral body implant, in accordance with an aspect of the present invention.

An alternative engagement portion 122 of the second elongate member 120 is shown in FIGS. 10 and 11. The alternative engagement portion 122 may include the protrusions 126 extending out from the lateral edges of the elongate member 120 and a tooth 129 extending out from each protrusion 126 toward a midline along the longitudinal axis of the second elongate member 120. The teeth 129 are positioned to engage an exterior surface of a first member 430 of an implant 400. The protrusions 126 may be sized to provide additional stability to the first member 430 during insertion into the patient.

Referring now to FIGS. 12 and 13, an optional locking mechanism 500 is shown. The locking mechanism 500 may be, for example, an external locking mechanism or an internal locking mechanism. The external locking mechanism (not shown) may be positioned by sliding the locking mechanism (not shown) over the exterior surfaces of the elongate members 110, 120 of the distraction instrument 100 to prevent the first elongate member 110 from separating from the second elongate member 120. Alternatively, as shown in FIG. 12, the locking mechanism 500 may include a first portion 502 with a first internal groove 504 and a second portion 506 with a second internal groove 508. The first internal groove 504 may be formed in the interior surface of the first elongate member 110 and the second internal groove 508 may be formed in the interior surface of the second elongate member 120. A key member 510, as shown in FIG. 13, may include a base 512 with a first end 514 shaped to correspond to the first internal groove 504 and a second end 516 shaped to correspond to the second internal groove 508. The key member 510 may be inserted into the locking mechanism 500 to secure the first and second elongate members 110, 130 and prevent the elongate members 110, 130 from separating and distracting the attached implant components before distraction is desired.

Figure 15:
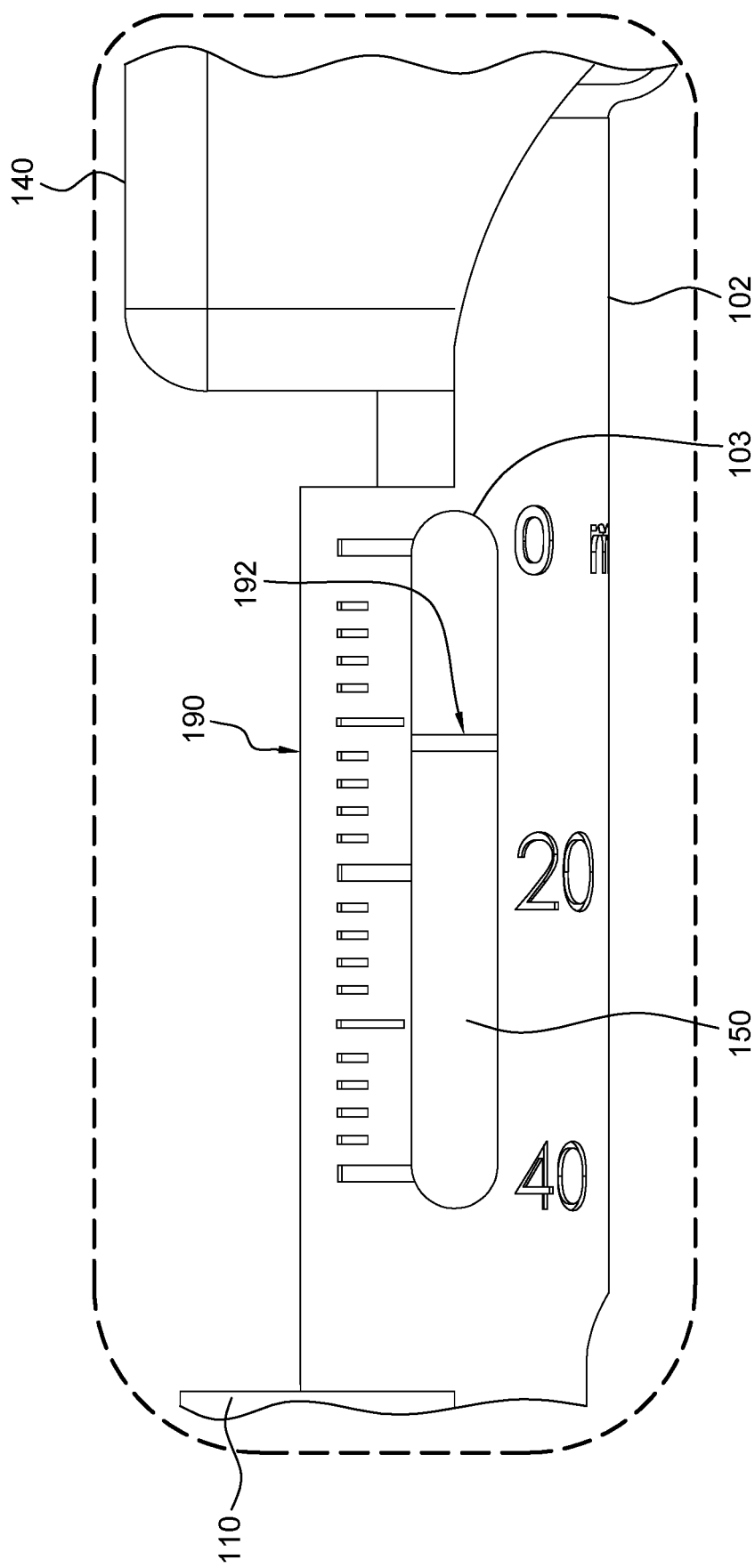
FIG. 15 is a detailed side view of the measurement mechanism shown as 190 in FIG. 14, in accordance with an aspect of the present invention.
Figure 16:
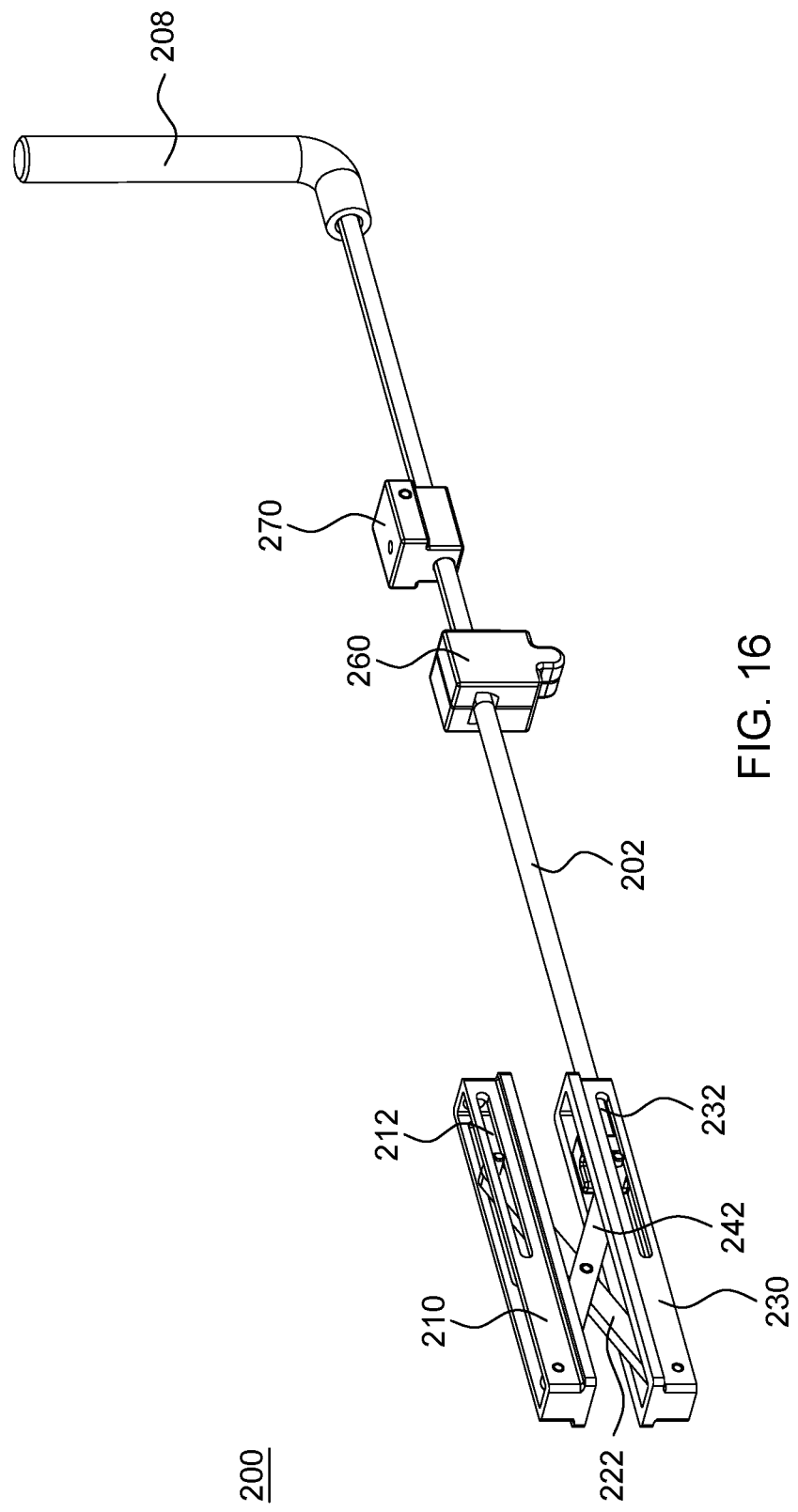
FIG. 16 is a perspective view of an expander mechanism, in accordance with an aspect of the present invention.
Figure 17:
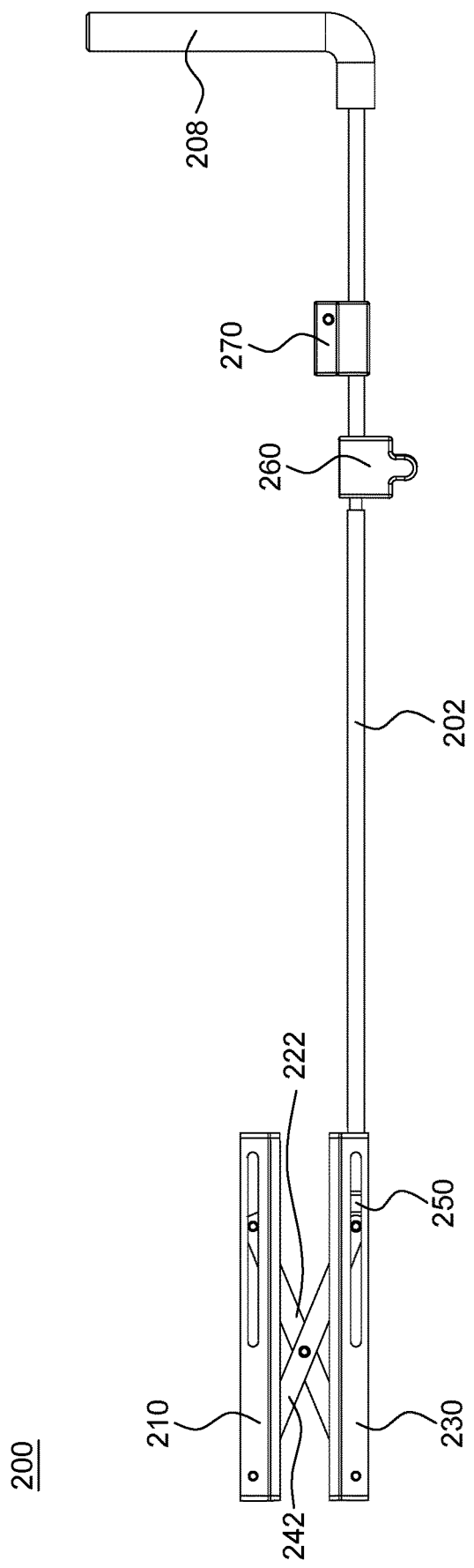
FIG. 17 is a side view of the expander mechanism of FIG. 16, in accordance with an aspect of the present invention.
Figure 18:
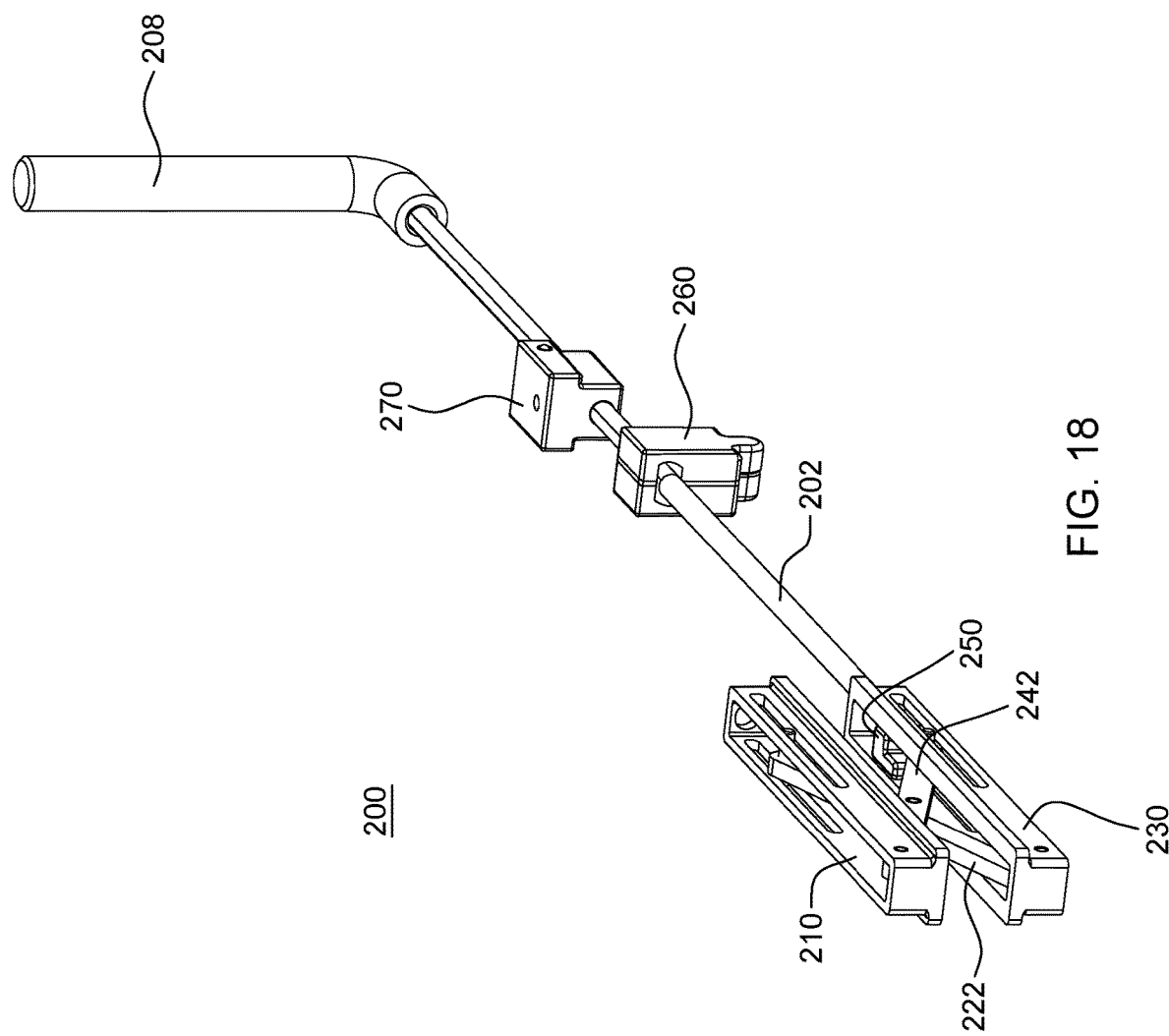
FIG. 18 is a front perspective view of the expander mechanism of FIG. 16, in accordance with an aspect of the present invention.
Figure 19:
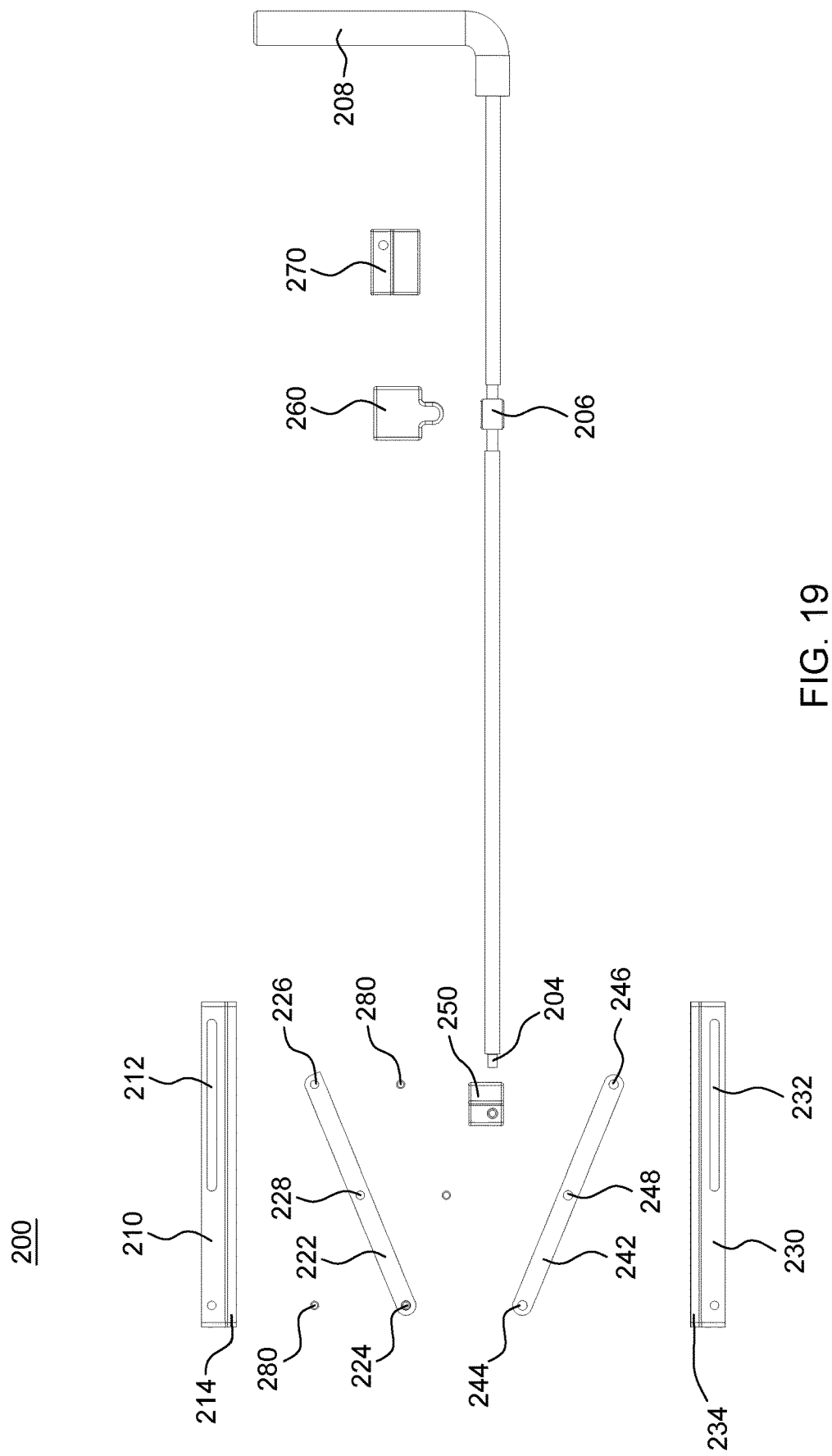
FIG. 19 is an exploded side view of the expander mechanism of FIG. 16, in accordance with an aspect of the present invention.
Figure 20:
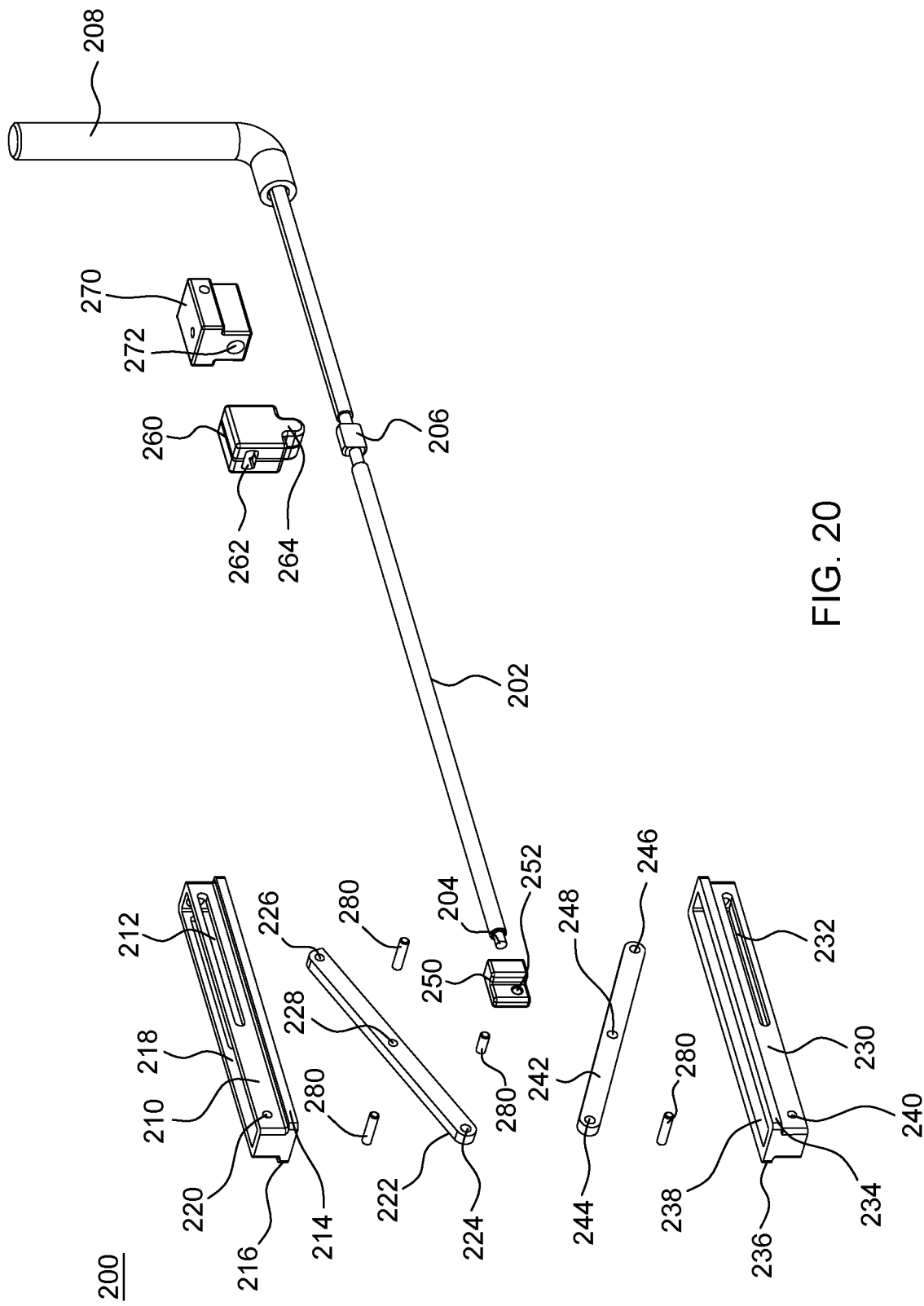
FIG. 20 is an exploded perspective view of the expander mechanism of FIG. 16, in accordance with an aspect of the present invention.

The distraction instrument 100 may also include a measurement mechanism 190 with an indicator line 192, as shown in FIGS. 14-15. The measurement mechanism 190 may be positioned on the body 102. The indicator line 192 may be positioned on the translating member 150 and may be, for example, a groove inset into the translating member 150. The body may include an opening 103 to enable the user to view the indicator line 192. The measurement mechanism 190 may be coupled to the movement system 140 to measure the translation of the movement system 140 which in turn provides the amount of distraction or separation performed on the first and second members 430, 450.

The expander mechanism 200, as shown in FIGS. 14 and 16-20, may include a rod 202, a first track member 210, a second track member 230, a first link member 222, a second link member 242, a sliding member 250, a movement member 260, and a locator 270. The rod 202 has a first end including an attachment portion 204 and a second end with a handle 208. The rod 202 may also include a protrusion 206 which may include, for example, a groove on either side of the protrusion 206. The proximal end of the rod 202 extends through an opening (not shown) in the second end of the second track member 230. The proximal end of the rod 202 is coupled to the sliding member 250 within an interior portion 238 in the second track member 230. The second track member 230 may also include a channel 232, a first edge protrusion 234, a second edge protrusion 236, and an interior portion 238. The second track member 230 may fit within the interior portion of the first elongate member 110 and the first and second edge protrusions 234, 236 may sit on the top of the first elongate member 110. The first track member 210 may include a channel 212, a first edge protrusion 214, a second edge protrusion 216, and an interior portion 218. The first track member 210 may fit within the interior portion of the second elongate member 120 and the first and second edge protrusions 214, 216 may sit on the bottom of the second elongate member 120.

The first link member 222 may include a first opening 224 secured to the second track member 230 through opening 240 with a fastener 280. The first link member 222 may also include a second opening 228 that may be used to secure the first link member 222 to the second link member 242 through a second opening 248 with a fastener 280. In addition, the first link member 222 may include a third opening 226 for receiving a fastener 280 to movably couple the first link member 222 to the channel 212 of the first track member 210. The second link member 242 also include a first opening 244 for securing the second link member 242 to the first track member 210 through opening 220 with a fastener 280. The second link member 242 may further include a third opening 246 for receiving a fastener 280 to movably couple the second link member 242 to the channel 232 of the second track member 230. The second link member 242 may also be secured to the sliding member 250 by inserting a fastener 280 through the channel 232 on a first side of the second track member 230, the third opening 246 of the second link member 242, the opening 252 in the sliding member 250, and the channel 232 on a second side of the second track member 230. The sliding member 250 is positioned to move the second track member 230 as force is applied to the movement member 260. The movement member 260 may have, for example, a first portion coupled to a second portion to receive the protrusion 206. The movement member 260 may include an opening 262 for the body 202 to extend through the movement member 260 and an extension member 264 for engaging the slide mechanism 154. The locator 270 may include an opening 272 for being positioned on the body 202 of the expander mechanism 200. The locator 270 provides a visual positioning marker for the user. The locator 270 may also be used as a stopper to mark how far the expander mechanism 200 should be inserted into the distraction instrument 100.

Figure 21:
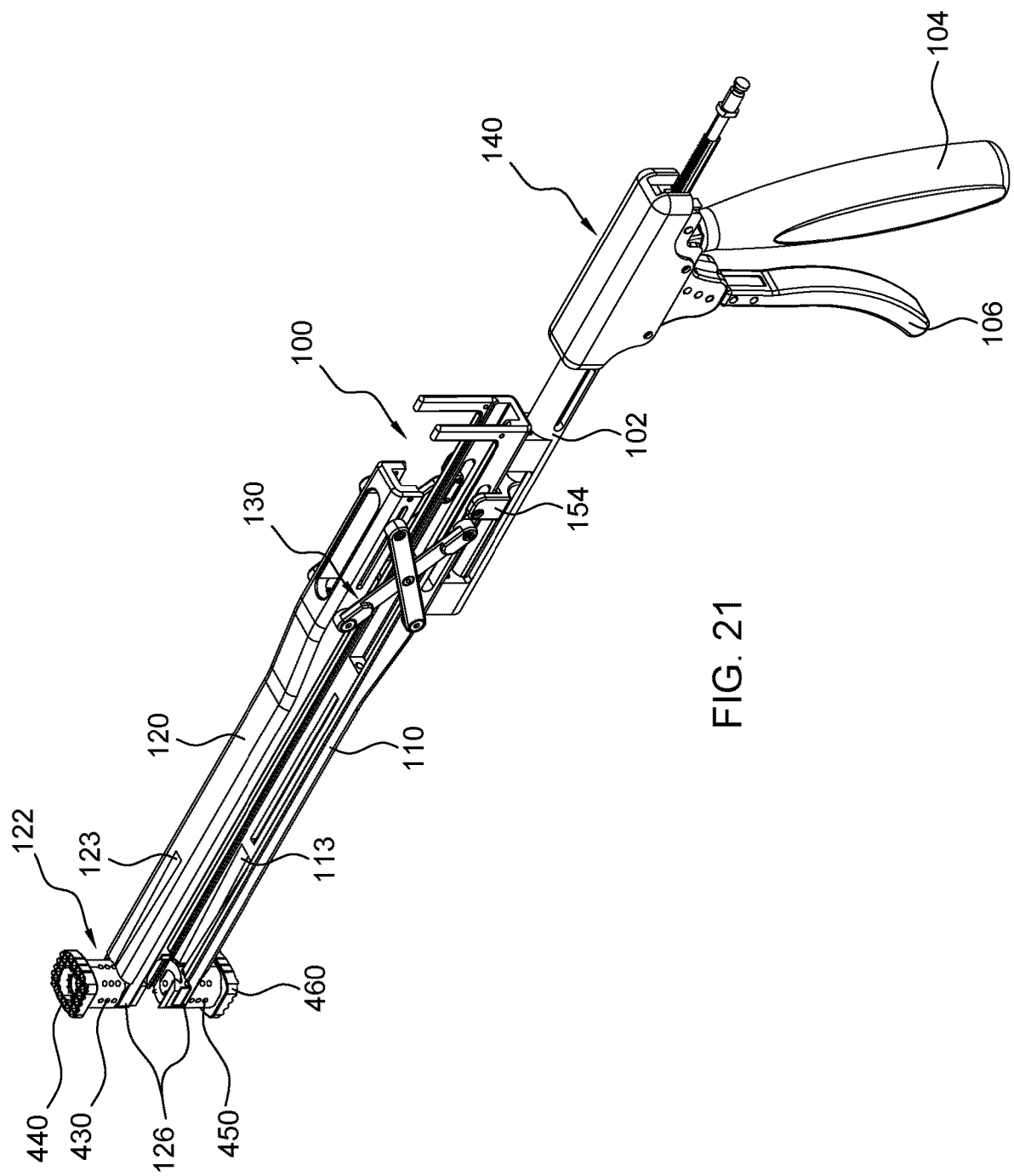
FIG. 21 is a perspective view of the distraction instrument of FIG. 1 in an expanded position and coupled to first and second members of an implant, in accordance with an aspect of the present invention.
Figure 22:
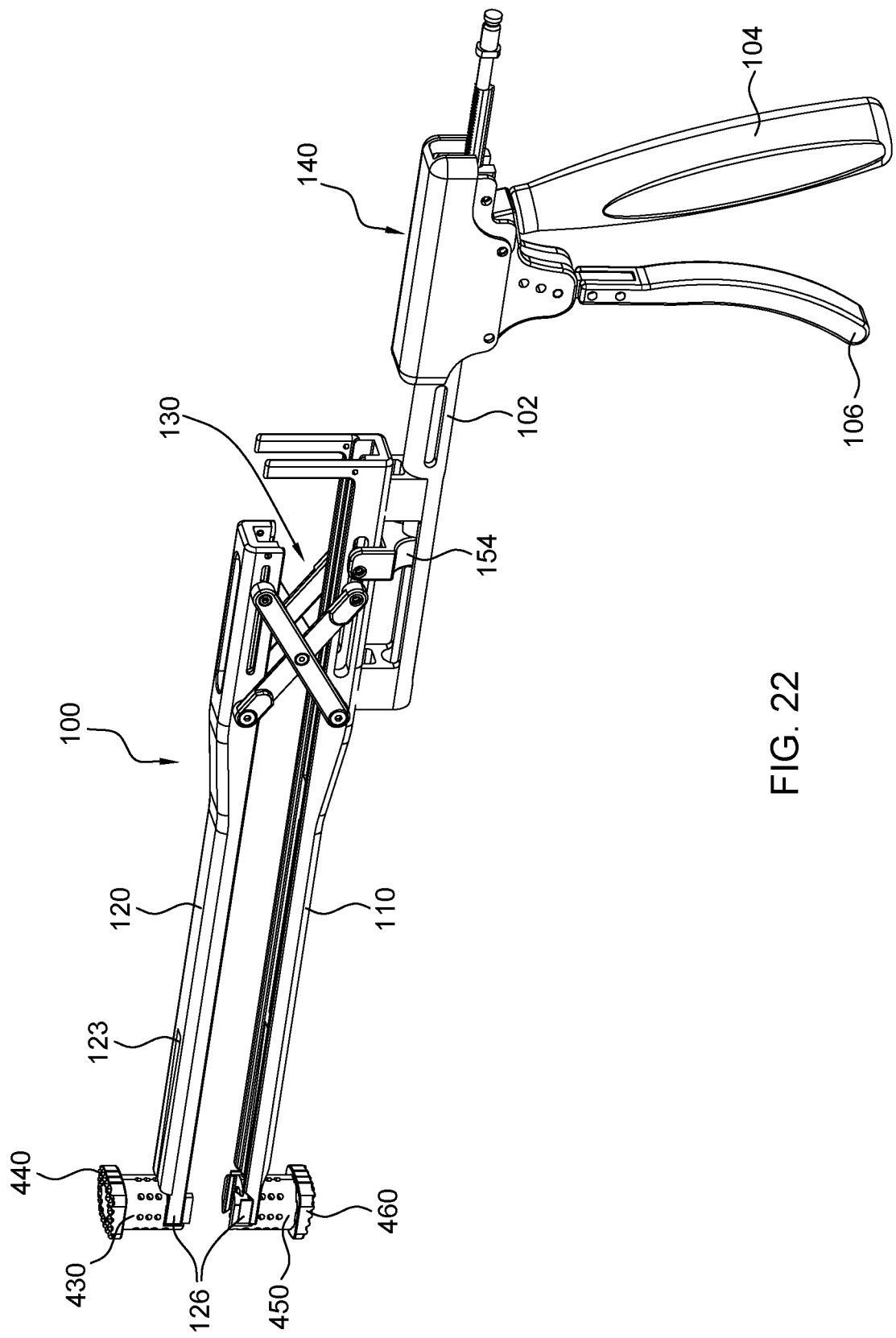
FIG. 22 is a side perspective view of the distraction instrument and first and second members of FIG. 21, in accordance with an aspect of the present invention.

As shown in FIG. 14, the expander mechanism 200 may be inserted into the distraction instrument 100 and positioned near a proximal end of the distraction instrument 100 prior to expansion. The expander mechanism 200 may be positioned near the proximal end to provide uniform expansion between the first and second elongate members 110, 120. By positioning the expander mechanism 200 near the proximal end of the distraction instrument 100 it may assist in preventing deflection of the engagement portions 112, 122. After distraction is performed with the expander mechanism 200, as shown in FIG. 14, the expander mechanism 200 may then be removed from the distraction instrument 100 leaving the distraction instrument 100 and the first and second members 430, 450 in an expanded position, as shown in FIGS. 21 and 22. Also shown in FIGS. 21 and 22 is a first member 430 coupled to the second elongate member 120 and a second member 450 coupled to the first elongate member 110.

Referring now to FIGS. 23-25, the spacer inserter 300 may include a handle 302 with an actuation mechanism 304. The actuation mechanism 304 is configured to enable the engagement shaft 306 to be secured in a first position wherein an implant spacer member 410 is secured to the proximal end 308 of the engagement shaft 306 for insertion into a patient. Then upon actuation of the actuation mechanism 304, the handle 302 is released and free to move in a longitudinal direction along the shaft 306. Once the handle 302 is released, the surgeon may use the handle 302 as a slide or slap hammer to facilitate tapping of the spacer member 410 through the tracks 434, 454 in the first and second members 430, 450. The spacer inserter 300 may also include an alignment head 310 for alignment of the intermediate spacer member 410 on the spacer inserter 300 for insertion into the patient. The spacer inserter 300 may further include a movable housing 312 coupled to a tab 314 to assist in the alignment and insertion of the intermediate spacer member 410 between the first and second elongate members 110, 120 of the distraction mechanism 100. The spacer inserter 300 may also include an engagement member 316 positioned on the housing 312. The housing 312 may be actuated by the tab 314 to engage the spacer 410. As the tab 314 is moved forward the housing 312 slides forward and causes the arms of the alignment head 310 to move closer together to engage the spacer 410. The arms of the alignment head 310 clamp onto the spacer 410 during insertion. Once the spacer 410 is inserted between the first and second members 430, 450 of the implant 400, the tab 314 may be moved in a rearward direction towards the handle 302 moving the housing 312 towards the handle 302 and releasing the arms of the alignment head 310. After the arms of the alignment head 310 disengage from the spacer 410, the spacer inserter 300 may be removed from the patient.

The engagement member 316 may be used to assist with moving the spacer 410 into position between the first and second members 430, 450 of the implant 400. The engagement member 316 may engage the extensions 111 of the distraction mechanism 100 to assist with moving the spacer 410 into position. The engagement member 316 may act as a stopper for holding the spacer inserter 300 in position while additional force is applied to the spacer 410 using the handle 302 and threads 318. The spacer inserter 300 may further include a threaded portion 318 positioned between the housing 312 and the handle 302. The threaded portion 318 may be used to provide additional leverage for the user when moving the implant 400 into position. To use the threaded portion 318, the actuation mechanism 304 may be depressed and the handle 302 moved proximally to engage the threaded portion 318. Then, the handle 302 may be screwed onto the threaded portion 318 to push the spacer 410 into position between the first and second members 430, 450 of the implant 400.

Figure 26:
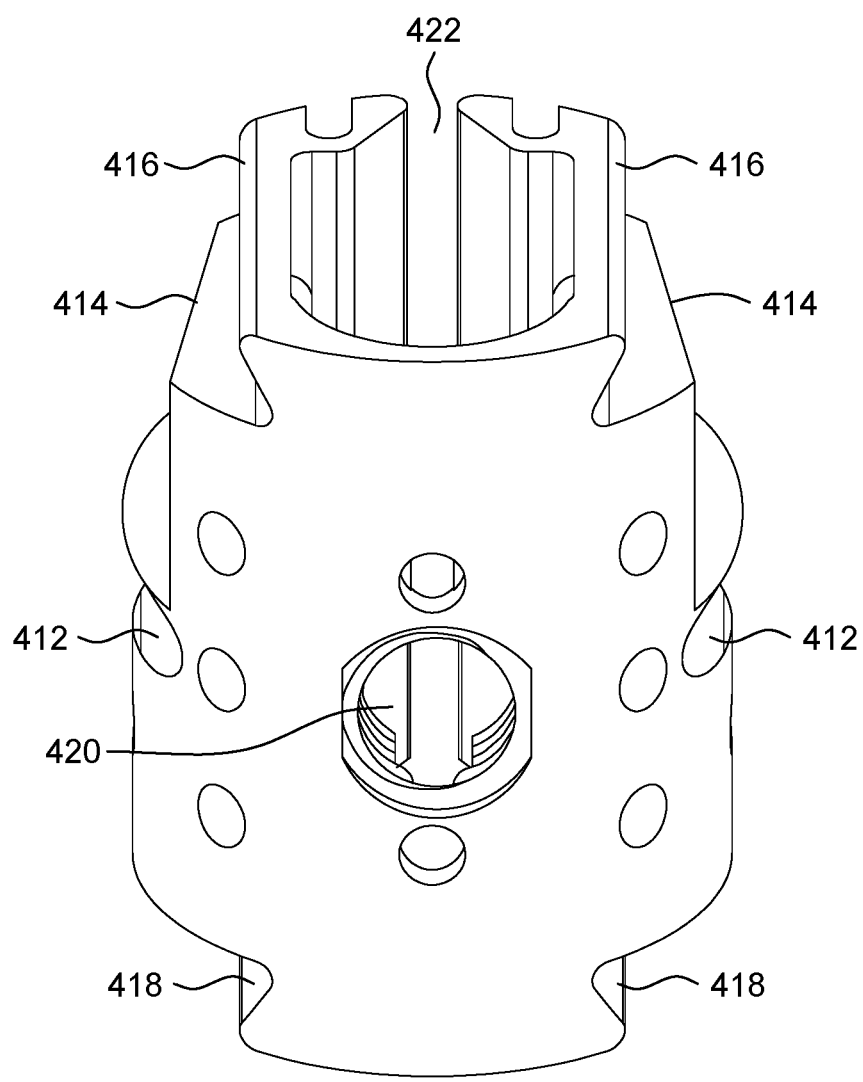
FIG. 26 is a front perspective view of the spacer of FIG. 24, in accordance with an aspect of the present invention.
Figure 27:
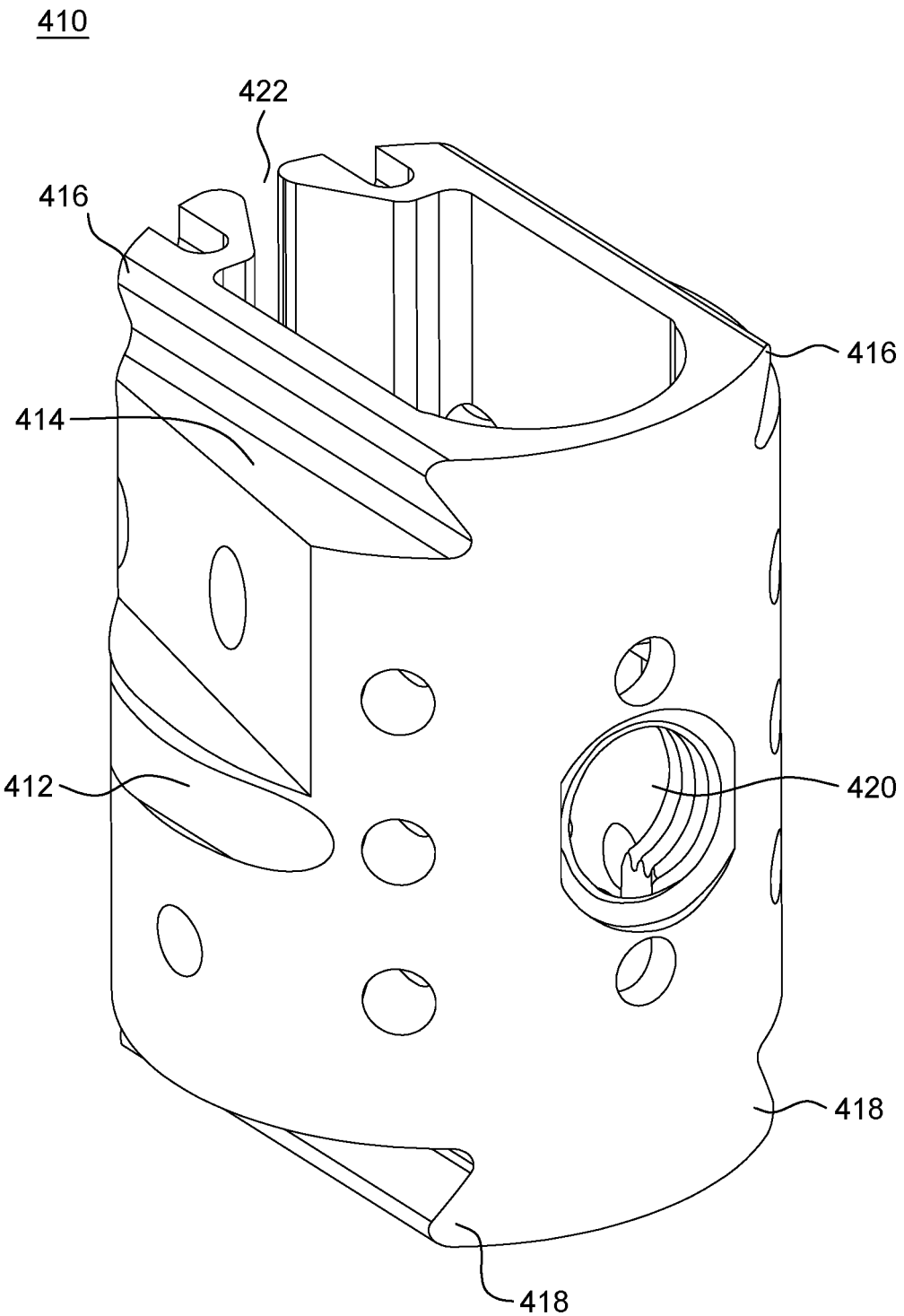
FIG. 27 is a side perspective view of the spacer of FIG. 26, in accordance with an aspect of the present invention.
Figure 29:
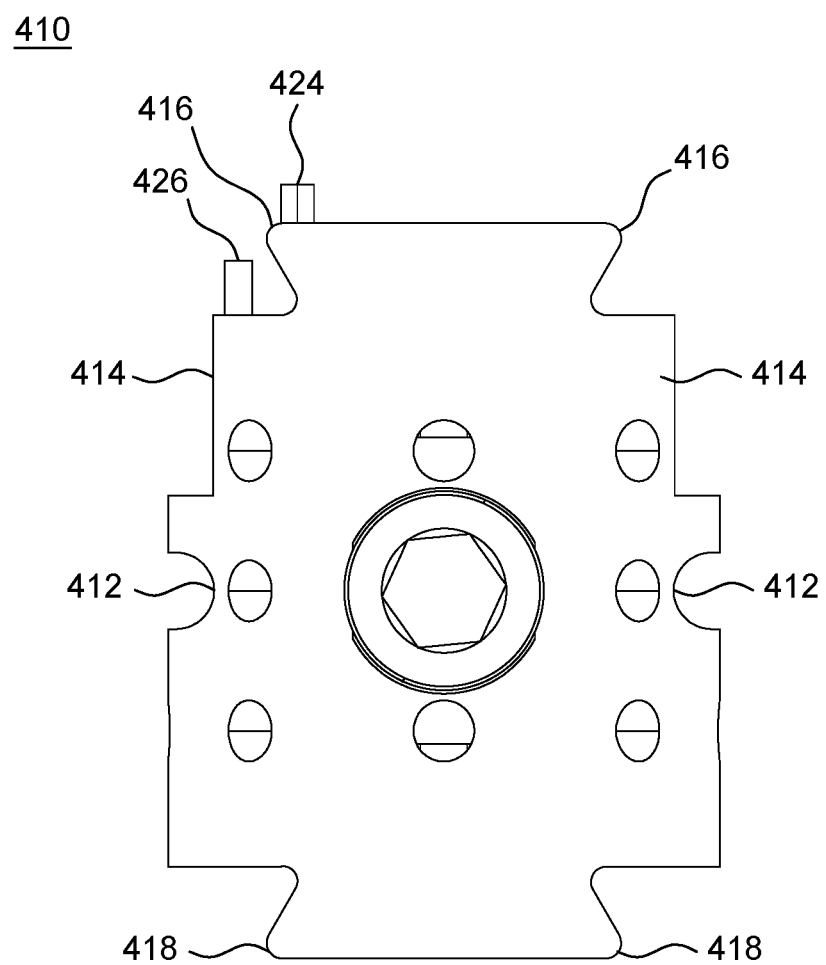
FIG. 29 is a front view of another embodiment spacer, in accordance with an aspect of the present invention.

Referring now to FIGS. 24-29 and 32, the intermediate spacer 410 is shown. The intermediate spacer 410 may include a first end and a second end. The intermediate spacer 410 may include a coupling mechanism 416 for engaging the first member 430 on the first end and a coupling mechanism 418 for engaging the second member 450 on the second end. The coupling mechanisms 416, 418 may be, for example, the male portions of a dovetail mechanism. The intermediate spacer 410 may also include at least one instrument coupling mechanism 412 on a side of the exterior surface of the intermediate spacer 410. In the depicted embodiment, the intermediate spacer 410 includes an instrument coupling mechanism 412 on each side of the exterior surface, as shown in FIGS. 26 and 29. The instrument coupling mechanisms 412 may be, for example, grooves or channels on the exterior side surfaces of the spacer 410. The grooves 412 are sized and shaped to engage the alignment head 310 of the spacer inserter 300.

Figure 30:
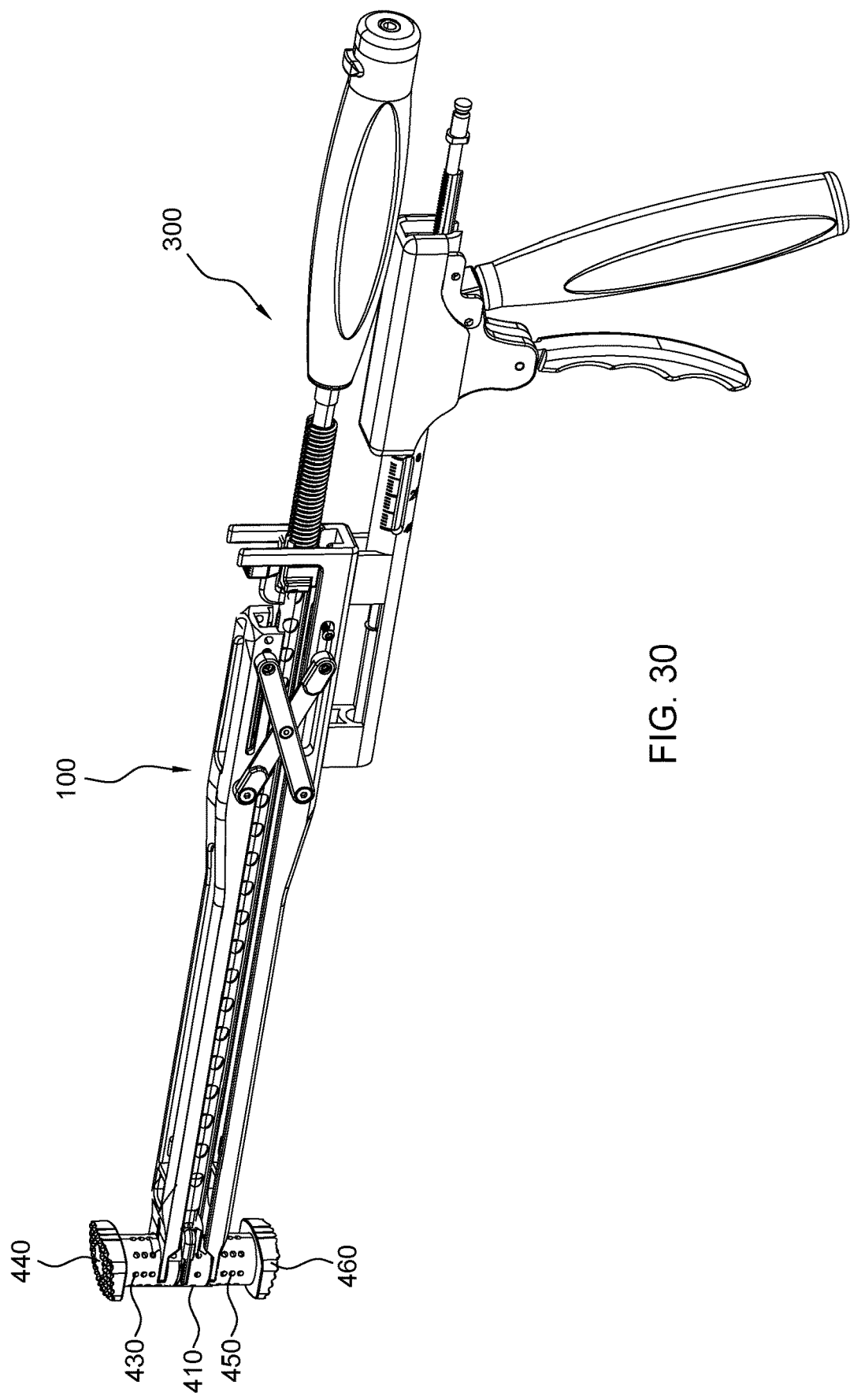
FIG. 30 is a side perspective view of the distraction instrument of FIG. 22 with the spacer inserter of FIG. 23 inserting the spacer of FIG. 25 between the first and second members of the implant, in accordance with an aspect of the present invention.
Figure 32:
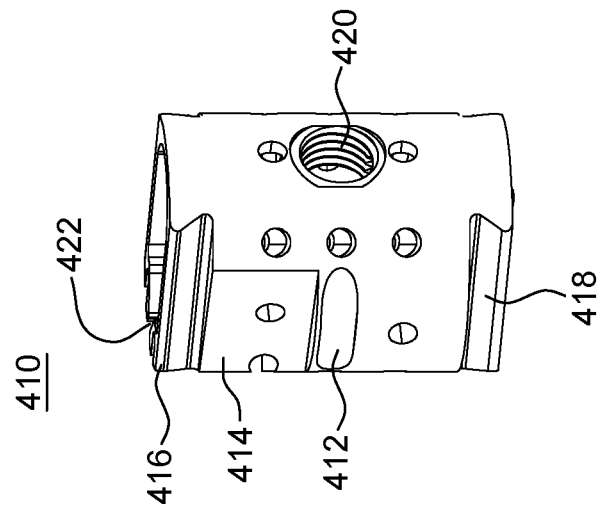
FIG. 32 is a side perspective view of the spacer of FIG. 30, in accordance with an aspect of the present invention.
Figure 31:
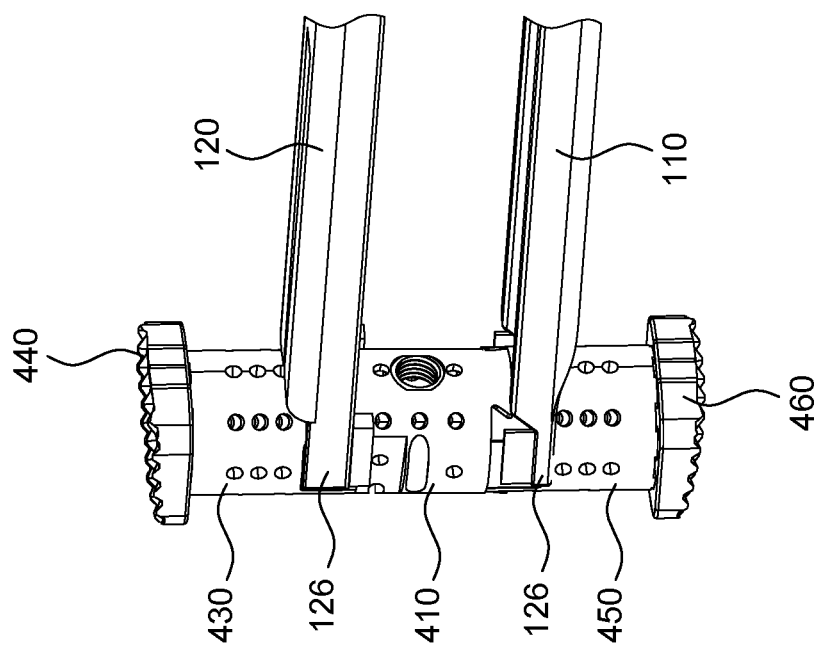
FIG. 31 is a detailed view of the proximal end of the system of FIG. 30, in accordance with an aspect of the present invention.
Figure 35:
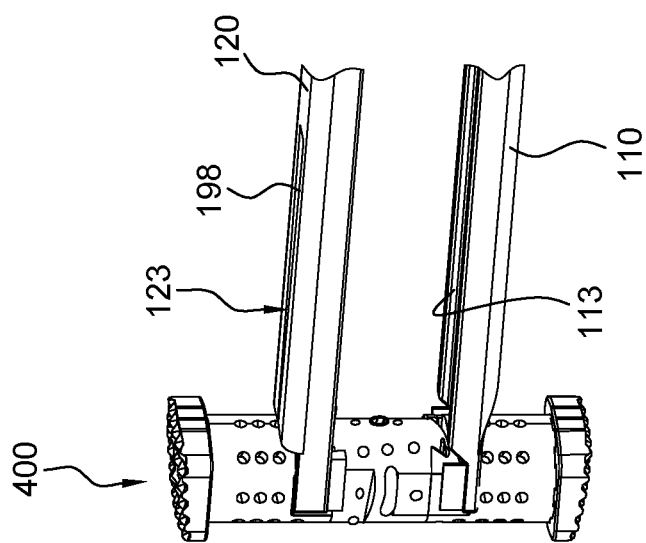
FIG. 35 is a detailed view of the proximal end of the system of FIG. 34, in accordance with an aspect of the present invention.
Figure 34:
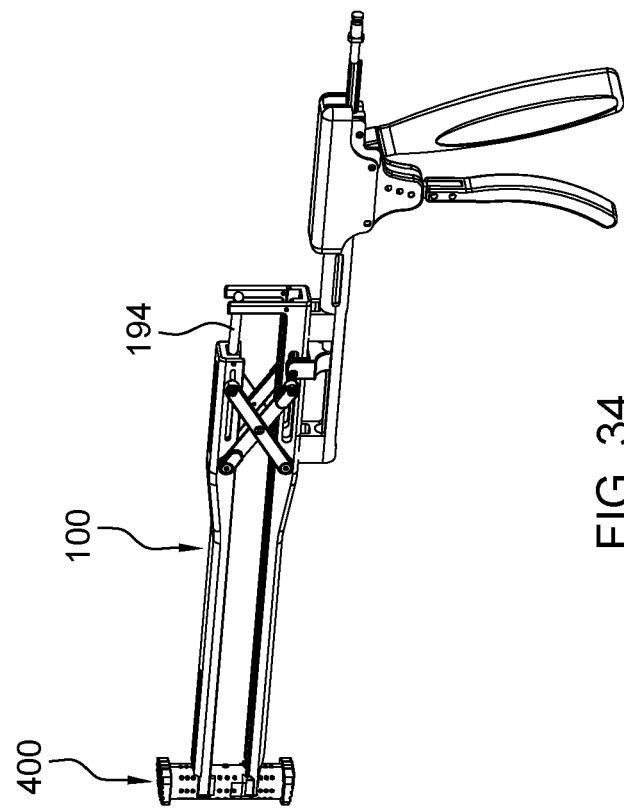
FIG. 34 is a perspective view of the distraction instrument of FIG. 1 after insertion of the implant and the expansion mechanism of FIG. 33, in accordance with an aspect of the present invention.

The intermediate spacer 410 may further include a tapered portion 414 positioned between the groove 412 and the coupling mechanism 416 on each side of the spacer 410 near the first end. The tapered portion 414 may taper from the front side to the back side of the intermediate spacer 410. The tapered portion 414 may be sized to expand the protrusions 126 of the engagement portion 122 as the intermediate spacer 410 is inserted between the first and second members 430, 450. As the protrusions 126 expand, the elongate members 110, 120 of the distraction mechanism 100 are released from the first and second members 430, 450, as shown in FIG. 30, and the distraction mechanism 100 may be removed from the implant 400. As shown in FIG. 31, the spacer inserter 300 may optionally be removed from the spacer 410 prior to removing the disengaged distraction mechanism 100 from the first and second members 430, 450. The spacer 410 may further include a fastener hole 420 on the front for receiving a fastener (not shown). The fastener hole 420 may be used to assist with insertion of the spacer 410 into the patient by coupling the spacer 410 to the inserter 300 during insertion. The fastener hole 420 may also receive a fastener (not shown) to secure the spacer 410 to the first and second members 430, 450. In addition, the spacer 410 may include a gap or channel 422 on the back of the spacer 410 to allow for slight deflection of the spacer 410 during insertion between the first and second members 430, 450.

As shown in FIG. 29, the spacer 410 may also optionally include a button 424 or button 426. The button 424, 426 may be positioned to engage at least one of the teeth 129 on the second elongate member 120 shown in FIGS. 10 and 11. The button 424, 426 may be positioned, for example, on a top surface of the spacer 410, as illustrated in FIG. 29. As the spacer 410 is inserted between the first and second members 430, 450 the button 424, 426 will engage at least one tooth 129 and push it out of an opening (not shown) in the side of the engagement portion 432 of the first member 430. Once the tooth 129 is disengaged from the first member 430, the distraction instrument 100 is free to be removed from engagement with the first and second members 430, 450. It is also contemplated that the spacer 410 may include a button 424, 426 on the second end or alternatively, on both the first and second ends.

FIG. 33 illustrates an alternative expansion mechanism 194 for releasing the protrusions 126 of the elongate members 110, 120 from the first and second members 430, 450. The expansion mechanism 194 may include a shaft portion 196 and a wedge portion 198. The wedge portion 198 may be sized to engage the opening 123 and as the wedge portion 198 travels proximally within the opening 123 the protrusions 126 are released from the first and second members 430, 450 to allow for removal of the distraction mechanism 100. The expansion mechanism 194 is shown in use with the distraction mechanism 100 in FIGS. 34-35. It is also contemplated that the expansion mechanism 194 may be used in an opening 113 in the first elongate member 110.

Figure 36:
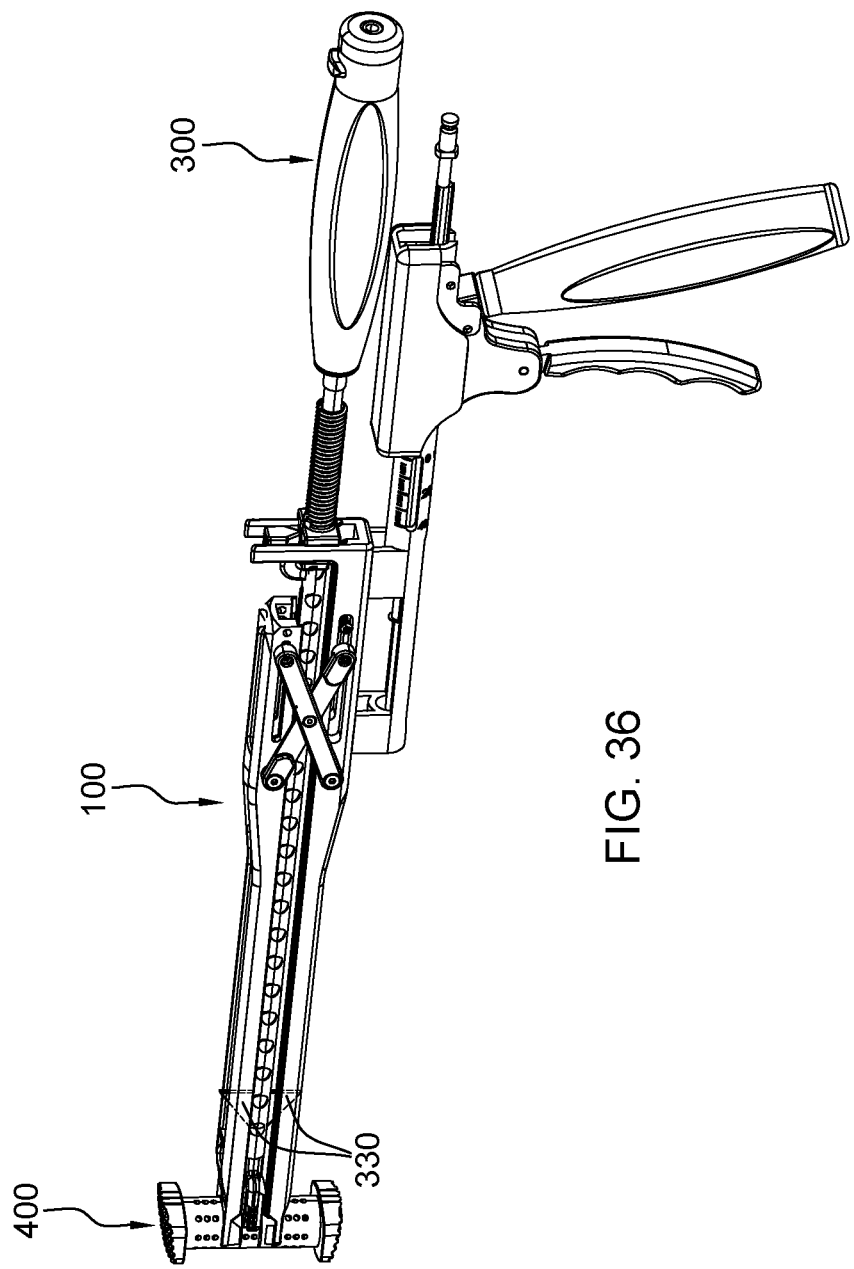
FIG. 36 is a perspective view of the system of FIG. 30 illustrating an alternative embodiment of an expansion mechanism positioned on the spacer inserter of FIG. 23, in accordance with an aspect of the present invention.

Another alternative expansion mechanism 330 is shown in FIG. 36. The expansion mechanism 330 may be coupled to the housing 312 of the spacer inserter 300 near the proximal end 308. As the spacer inserter 300 is moved proximally within the distraction mechanism 100 the expansion mechanism 330 will be positioned within at least one opening 113, 123 and the expansion mechanism 330 will expand the protrusions 126 away from each other to disengage the distraction mechanism 100 from the first and second members 430, 450.

Figure 38:
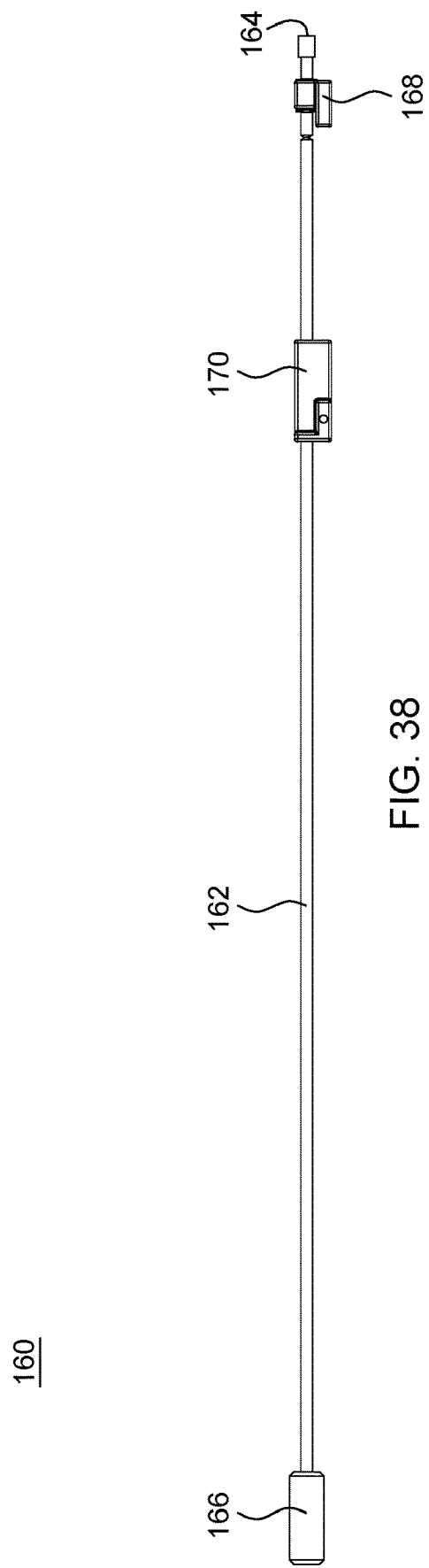
FIG. 38 is a perspective view of the first adjustment mechanism of FIG. 37 from a second end, in accordance with an aspect of the present invention.

FIGS. 37 and 38 illustrate a first adjustment mechanism 160 which may be used to secure the first member 430 to the spacer 410 once a final position is achieved. The first adjustment mechanism 160 may include a shaft 162 with a drive mechanism 164 at a first end and a handle 166 at a second end. The first adjustment mechanism 160 may also include a first guide portion 168 and a second guide portion 170. The first and second guide portions 168, 170 may be used to position the first adjustment mechanism 160 with respect to the second elongate member 120 and the first member 430 of the implant 400. The first adjustment mechanism 160 is a separate instrument for use with the distraction mechanism 100. It is also contemplated that a first adjustment mechanism could be integrated into the distraction mechanism 100 for securing the first member 430 in the desired position.

FIGS. 39 and 40 show a second adjustment mechanism 180 which may be used to secure the second member 450 to the spacer 410 once a final position is achieved. The second adjustment mechanism 180 may include a shaft 182 with a drive mechanism 184 at a first end and a handle 186 at a second end. The first adjustment mechanism 180 may also include a first guide portion 188 and a second guide portion 189. The first and second guide portions 188, 189 may be used to position the second adjustment mechanism 180 with respect to the first elongate member 110 and the second member 450 of the implant 400. The second adjustment mechanism 180 is a separate instrument for use with the distraction mechanism 100. It is also contemplated that a second adjustment mechanism could be integrated into the distraction mechanism 100 for securing the second member 450 in the desired position.

A spinal implant 400 is shown in FIGS. 41-47. The implant 400 may include, for example, an intermediate spacer 410, a first member 430, a first end member 440, a second member 450, and a second end member 460. Although not shown, it is also contemplated that the implant 400 may include, for example, the intermediate spacer 410, the first member 430, and the second member 450. In the alternative embodiment, a first end of the first member 430 and a second end of the second member 450 may have a bone contacting surface with, for example, a coating or textured surface to allow for bone ingrowth or ongrowth. The intermediate spacer 410 is described in greater detail above with reference to FIGS. 24-29 and 32. The first member 430 may include an engagement portion or insertion instrument coupling portion 432 on the exterior surface of the first member 430. The insertion instrument coupling portion 432 may optionally include an opening (not shown) extending into the first member 430. The first member 430 may also include a coupling mechanism 434, which may be, for example, a female portion of a dovetail mechanism. The first member 430 may further include an engagement portion 436 at a first end with at least one channel 438 for coupling the first end member 440. The engagement portions 436 may, for example, engage the openings or pockets in the first end member 440 and may prohibit the first end member 440 from rotating along the long axis with respect to the first member 430 once assembled. The first end member 440 may include a coupling member 442 extending out from a bottom surface of the first end member 440 to engage an undercut on an inner diameter of the engagement portion 436 of the first member 430. The tabs of the coupling member 442 may, for example, snap to engage the undercut of the first member 430 to prevent axial separation of the end member 440 from the first member 430. The first end member 440 may also include a bone contacting surface 444 on the top end, which may include, for example, a coating, texture, or the like to assist with securing the implant 400 to the bone and allowing for bone ongrowth or ingrowth.

With continued reference to FIGS. 41-47, the second member 450 may include an engagement portion or insertion instrument coupling portion 452 on the exterior surface of the second member 450. The insertion instrument coupling portion 452 may optionally include an opening (not shown) extending into the second member 450. The second member 450 may also include a coupling mechanism 454, which may be, for example, a female portion of a dovetail mechanism. The second member 450 may further include an engagement portion 456 at a first end with at least one channel 458 for coupling the second end member 460. The engagement portions 456 may, for example, engage the openings or pockets in the second end member 460 and may prohibit the second end member 460 from rotating along the long axis with respect to the second member 450 once assembled. The second end member 460 may include a coupling member 462 extending out from a top surface of the second end member 460 to engage an undercut on an inner diameter of the engagement portion 456 of the second member 450. The tabs of the coupling member 462 may, for example, snap to engage the undercut of the second member 450 to prevent axial separation of the end member 460 from the second member 450. The second end member 460 may also include a bone contacting surface 464 on the bottom end, which may include, for example, a coating, texture, or the like to assist with securing the implant 400 to the bone and allowing for bone ongrowth or ingrowth.

A distraction instrument 1000 is shown in FIGS. 48-61. The distraction instrument 1000, as shown in FIGS. 48-54 and 56-58, may include a first inserter member 1110 and second inserter member 1130 at a first end 1102. The distraction instrument 1000 may also include a first arm 1150 coupled to the first inserter member 1110 and second arm 1160 coupled to the second inserter member 1130. The distraction instrument 1000 may further include a distraction system 1180 engaging the first and second arms 1150, 1160. In addition, the distraction instrument 1000 may include a first handle 1210 and a second handle 1230 at the second end 1104. The first handle 1210 may be coupled to the second end of the first arm 1150 and the second member 1190 and the second handle 1230 may be coupled to the second end of the second arm 1160 and the first member 1182. The distraction instrument 1000 may also include a stop member 1202 positioned to engage the first and second handles 1210, 1230 to hold the distraction instrument 1000 in the expanded position.

Figure 55:
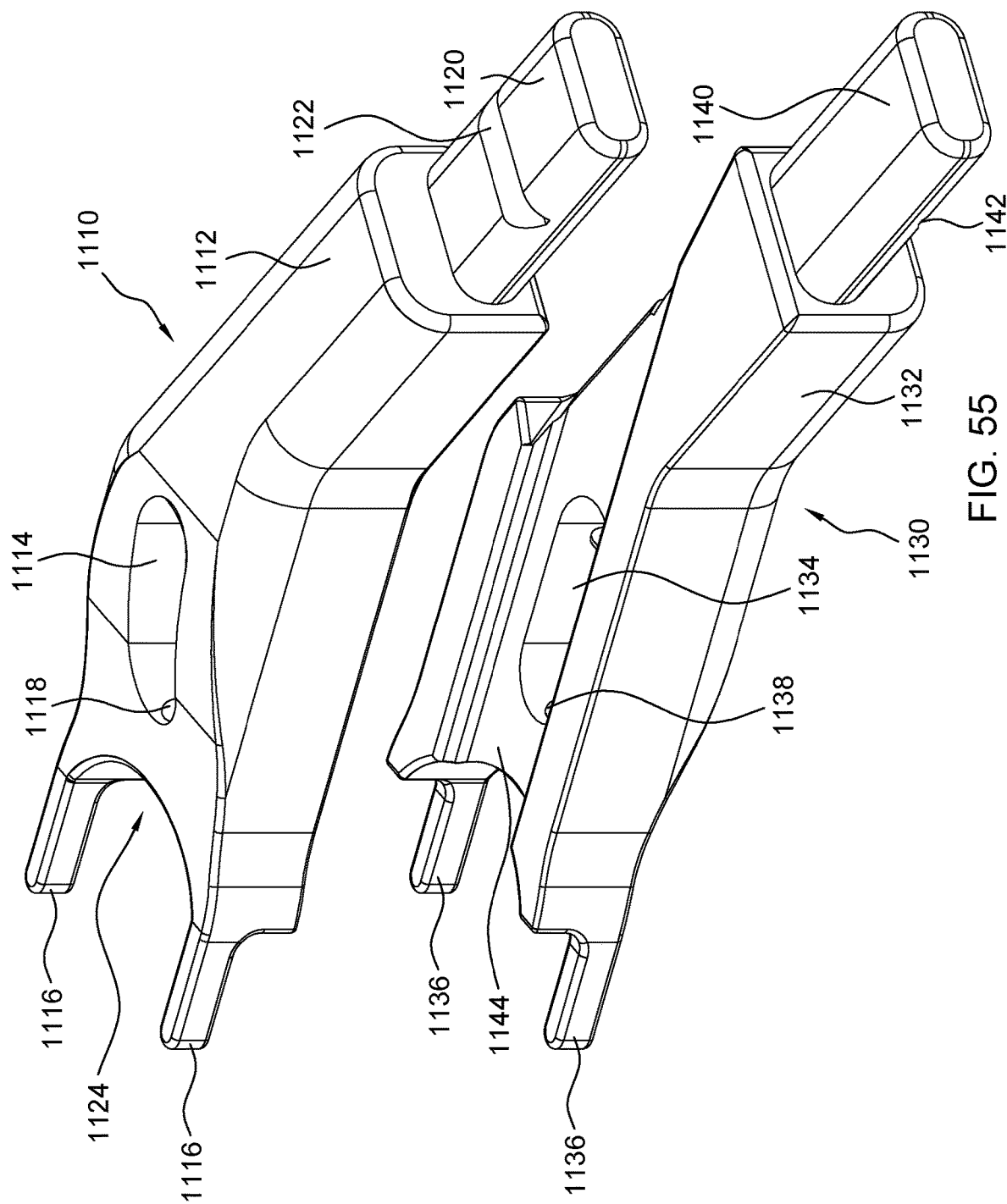
FIG. 55 is a perspective view of the inserter members of the distraction instrument of FIG. 48, in accordance with an aspect of the present invention.
Figure 57:
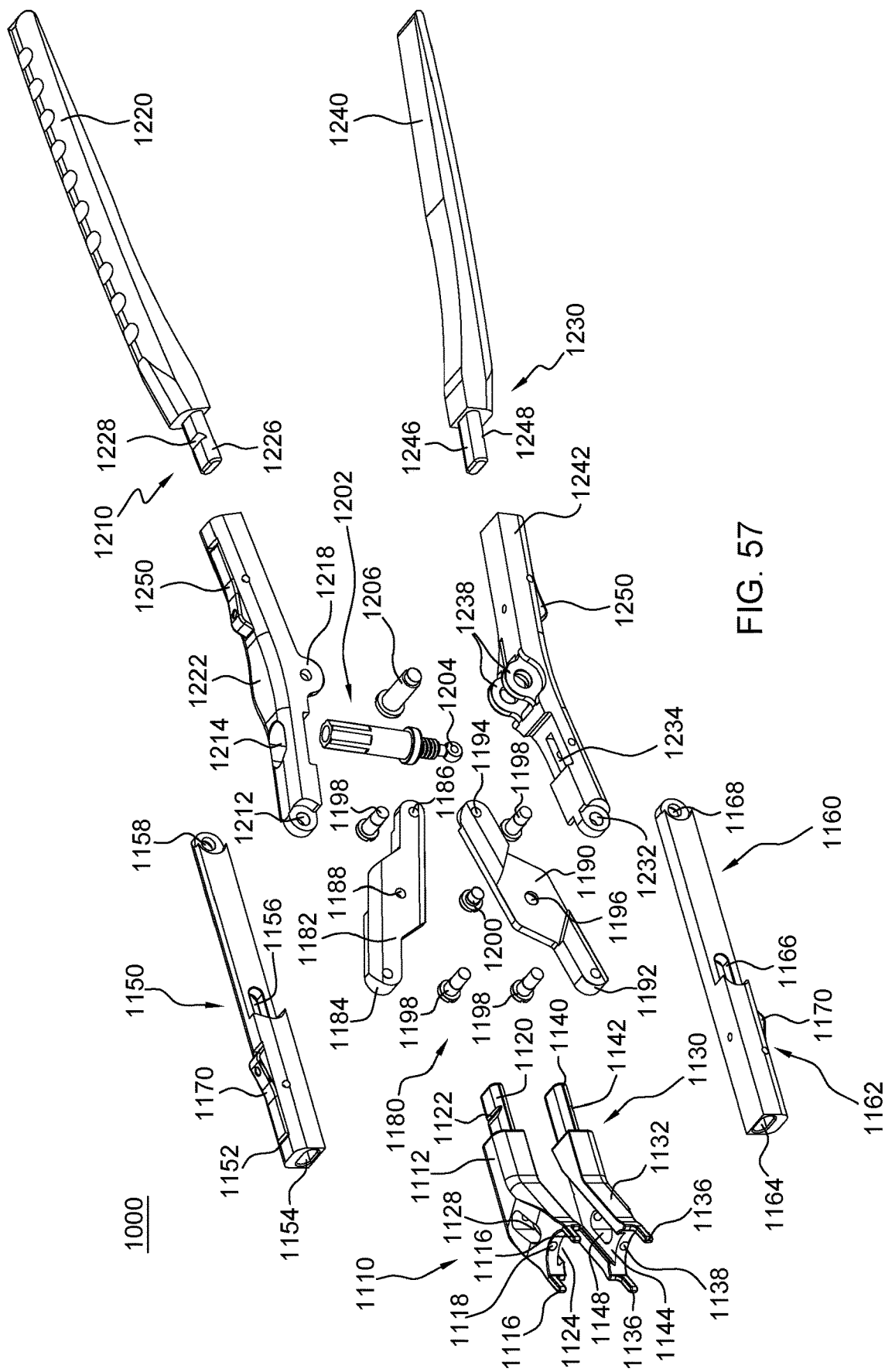
FIG. 57 is a partially exploded perspective view of the distraction instrument of FIG. 48, in accordance with an aspect of the present invention.
Figure 58:
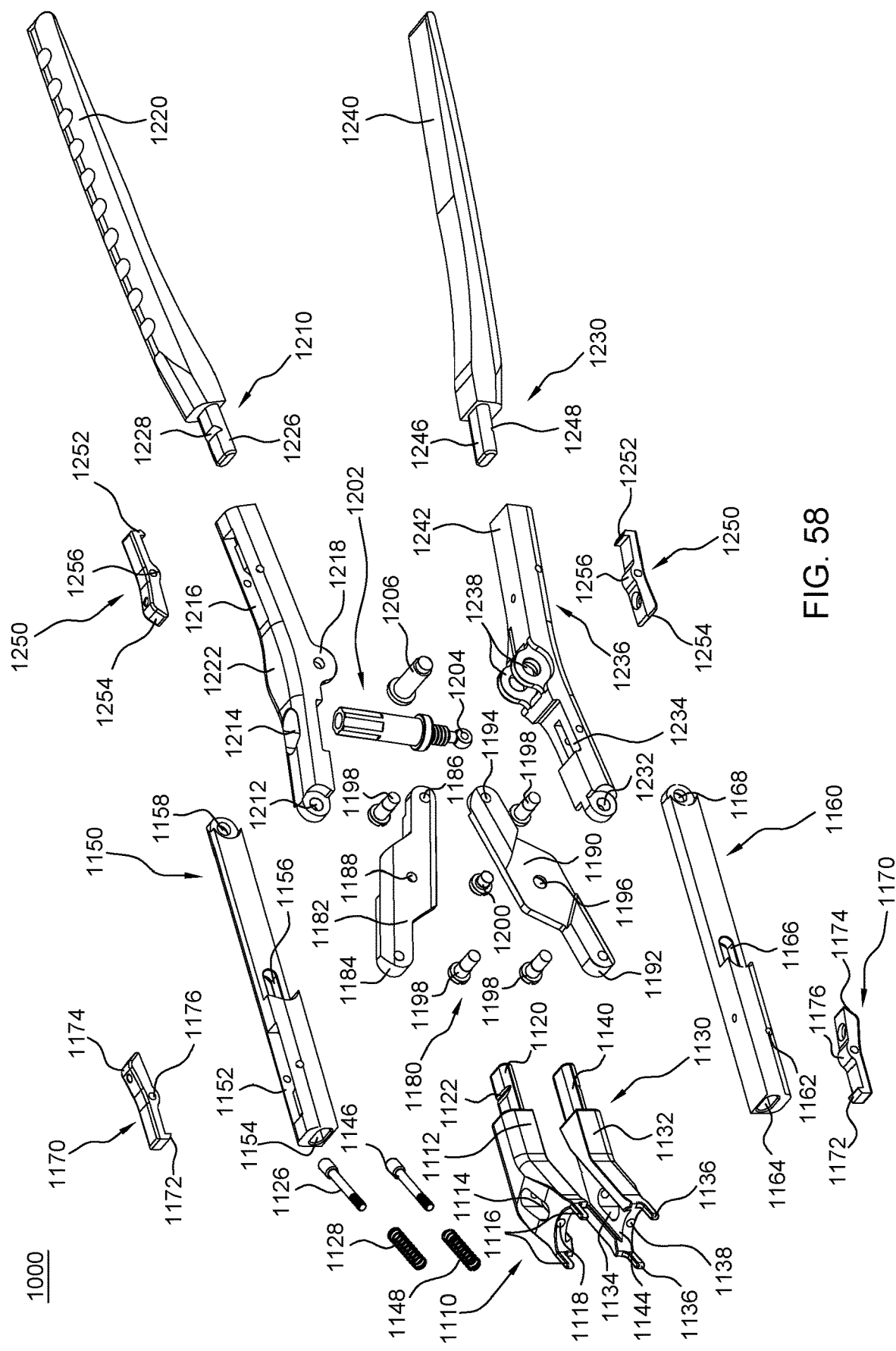
FIG. 58 is an exploded view of the distraction instrument of FIG. 48, in accordance with an aspect of the present invention.
Figure 59:
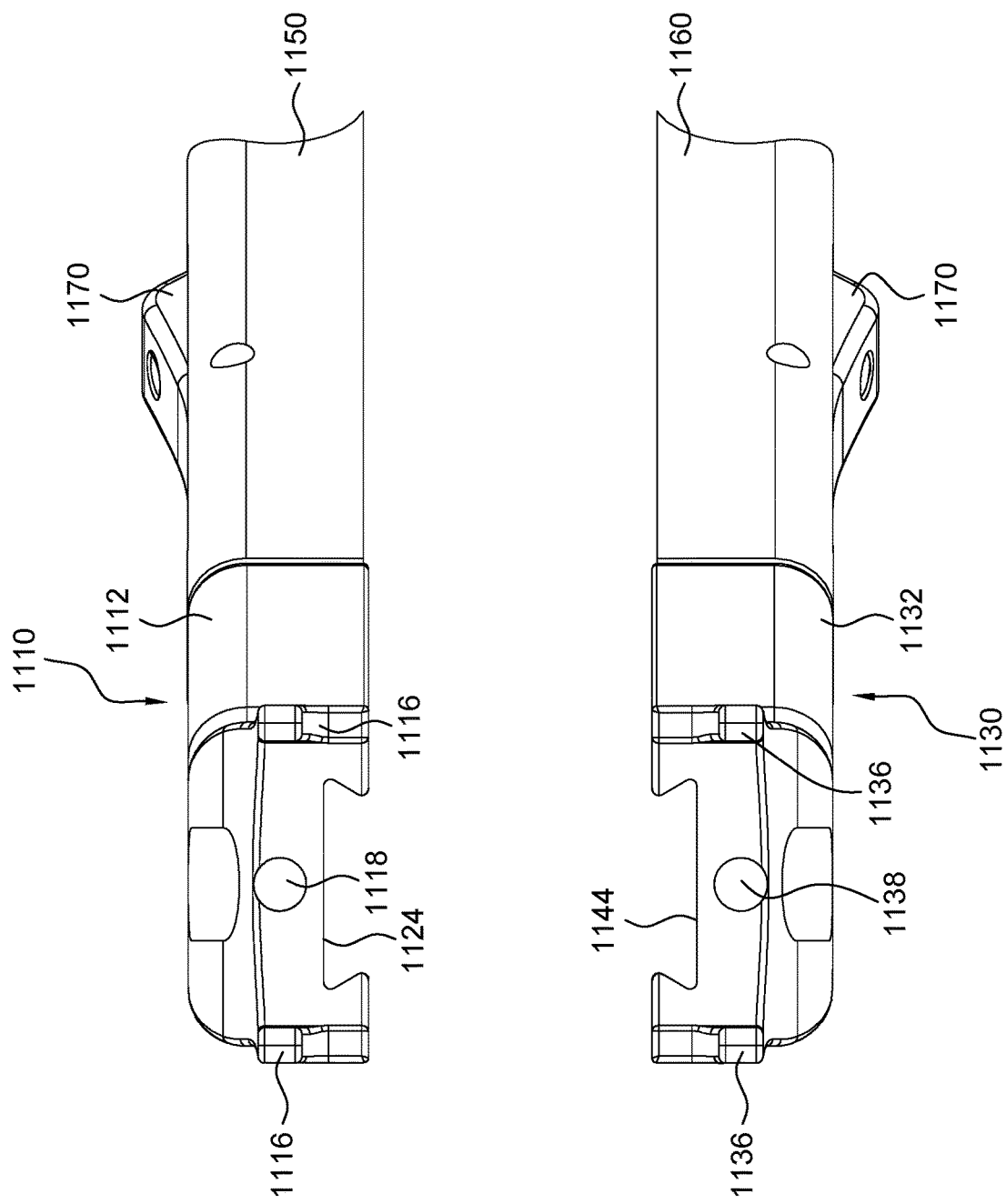
FIG. 59 is a detailed side view of the first end of the distraction instrument of FIG. 48, in accordance with an aspect of the present invention.
Figure 60:
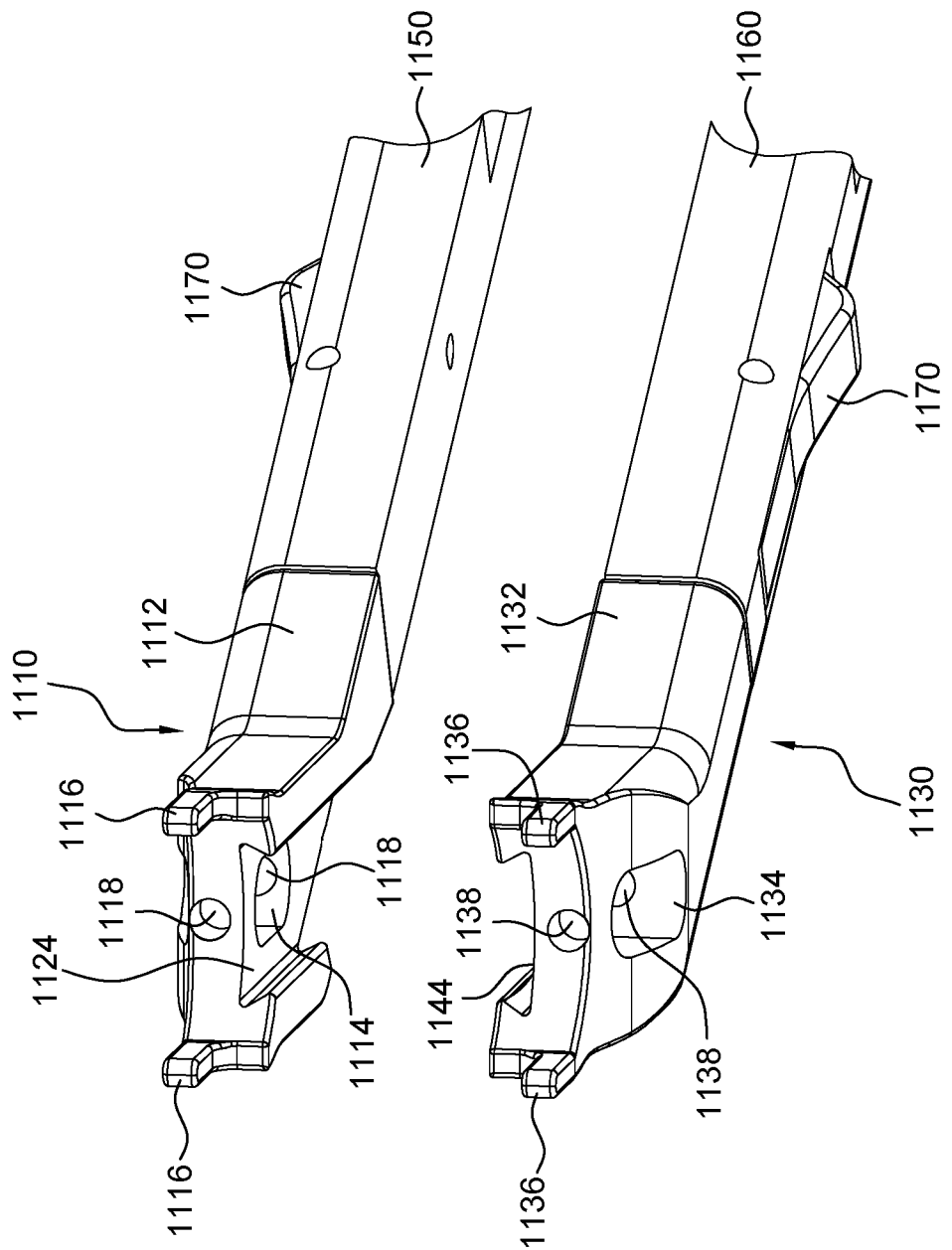
FIG. 60 is a detailed bottom perspective view of the first end of the distraction instrument of FIG. 48, in accordance with an aspect of the present invention.

As shown in FIGS. 55, 57, and 58, the first inserter member 1110 may include a body 1112 with a first opening 1114 extending from a top surface through to a bottom surface. The first inserter member 1110 may also include engagement protrusions 1116 extending out from the first end of the body 1112 for engaging a portion of a spinal implant. The first inserter member 1110 may further include a hole 1118 extending from a side of the first inserter member 1110 through the opening 1114 and out the front of the inserter member 1110. In addition, the first inserter member 1110 may include a coupling member 1120 extending out from the second end of the body 1112. The coupling member 1120 may have a locking groove 1122 on a top surface of the coupling member 1120. The coupling member 1120 may have, for example, a width and height that is smaller than the width and height of the body 1112. The first inserter member 1110 may also include an insertion track 1124 for receiving a spinal implant spacer, as discussed in greater detail below with reference to FIGS. 65-68. The insertion track 1124 may be, for example, a groove set into a bottom surface of the body 1112 and extending from a first end out a side of the first inserter member 1110. The insertion track 1124 may be, for example, a dovetail shaped groove to receive a correspondingly shaped spinal implant spacer.

The second inserter member 1130 may include a body 1132 with a first opening 1134 extending from a top surface through to a bottom surface, as shown in FIGS. 55, 57, and 58. The second inserter member 1130 may also include engagement protrusions 1136 extending out from the first end of the body 1132 for engaging a portion of a spinal implant. The second inserter member 1130 may further include a hole 1138 extending from a side of the second inserter member 1130 through the opening 1134 and out the front of the inserter member 1130. In addition, the second inserter member 1130 may include a coupling member 1140 extending out from the second end of the body 1132. The coupling member 1140 may have a locking groove 1142 on a bottom surface of the coupling member 1140. The coupling member 1140 may have, for example, a width and height that is smaller than the width and height of the body 1132. The second inserter member 1130 may also include an insertion track 1144 for receiving a spinal implant spacer, as discussed in greater detail below with reference to FIGS. 65-68. The insertion track 1144 may be, for example, a groove set into a top surface of the body 1132 and extending from a first end out a side of the second inserter member 1130. The insertion track 1144 may be, for example, a dovetail shaped groove to receive a correspondingly shaped spinal implant spacer.

Figure 69:
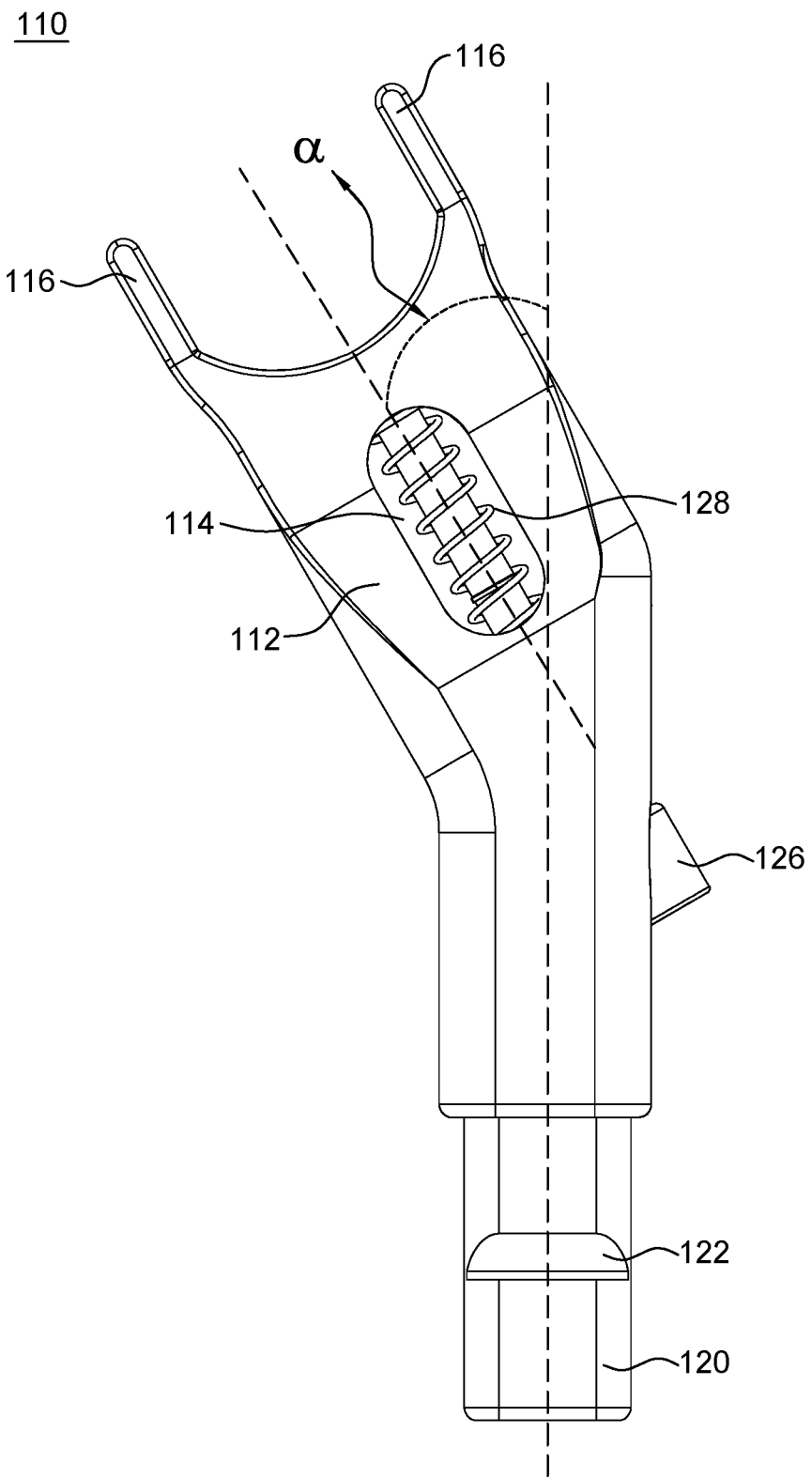
FIG. 69 is a top view of an inserter member for the distraction instrument of FIG. 48, in accordance with an aspect of the present invention.
Figure 70:
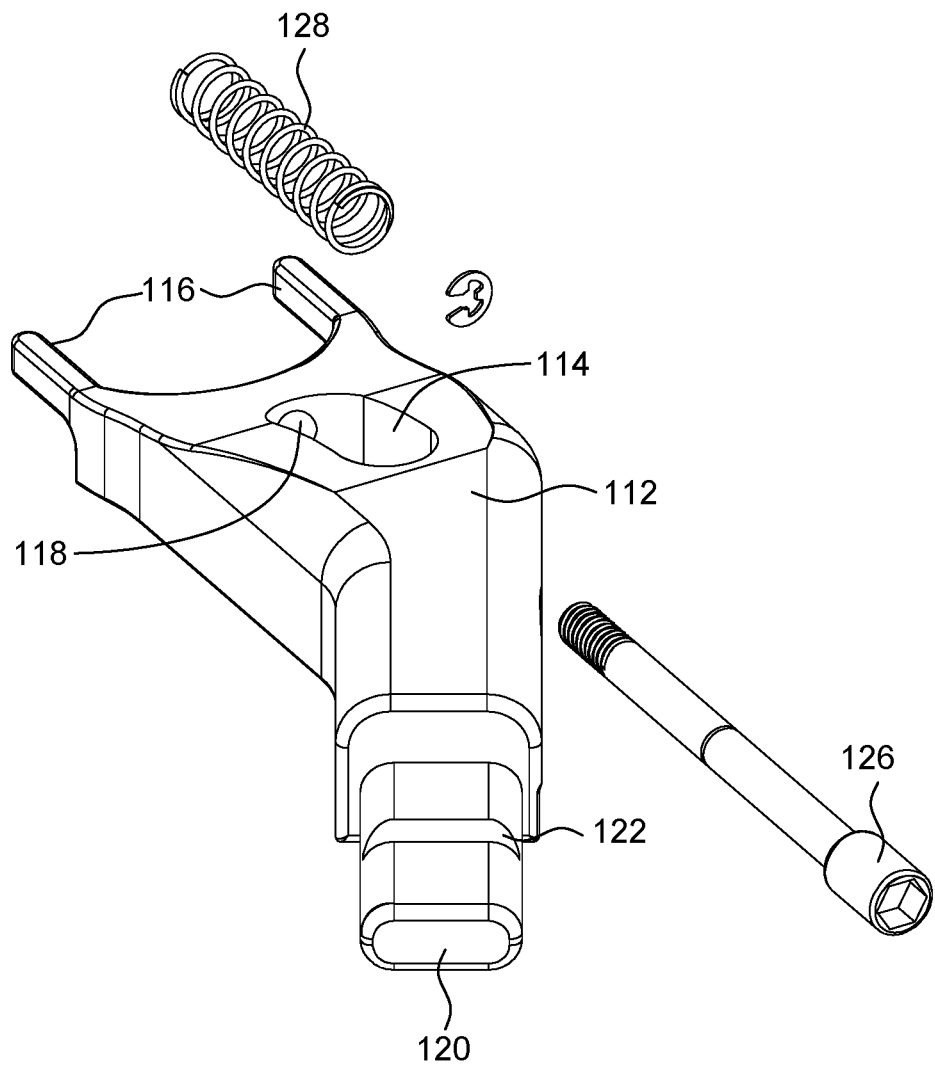
FIG. 70 is an exploded rear, perspective view of the inserter member of FIG. 69, in accordance with an aspect of the present invention.

As shown in FIGS. 69-70, the inserter members 1110, 1130 may be angled from the longitudinal axis at an angle α. The angle α may, for example, range from approximately 0° to approximately 60° and more particularly may be 0°, 30°, 45°, 60°. The angle α may be selected to provide visualization of the patient's spine and for ease of insertion of the spinal implant.

Figure 61:
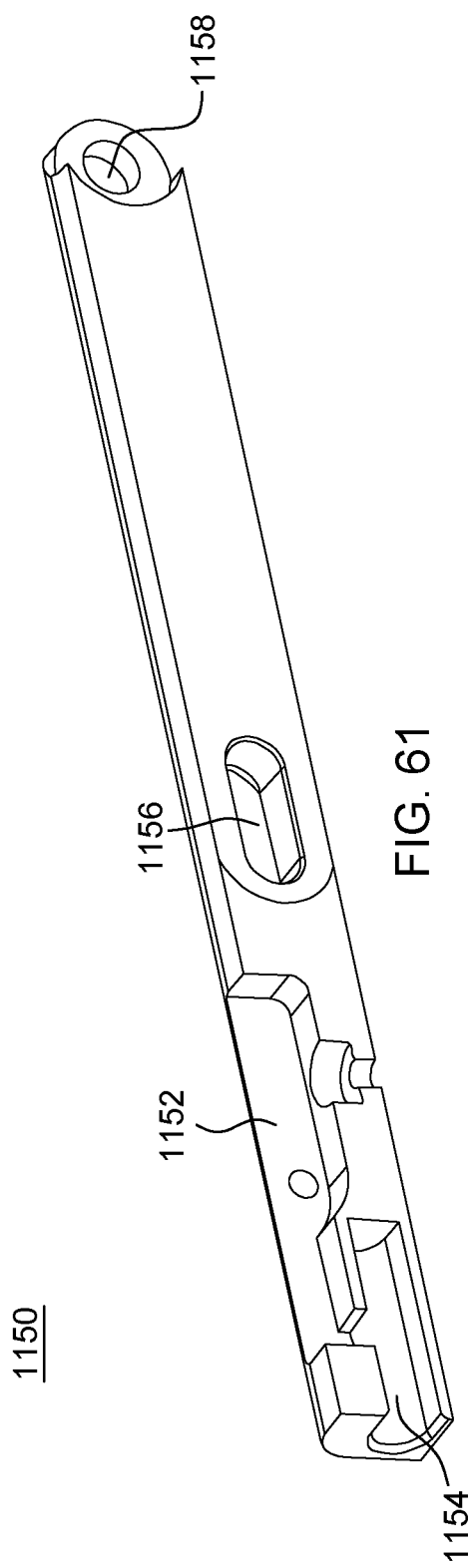
FIG. 61 is a cross-sectional view of a first arm of the distraction instrument of FIG. 48, in accordance with an aspect of the present invention.
Figure 62:
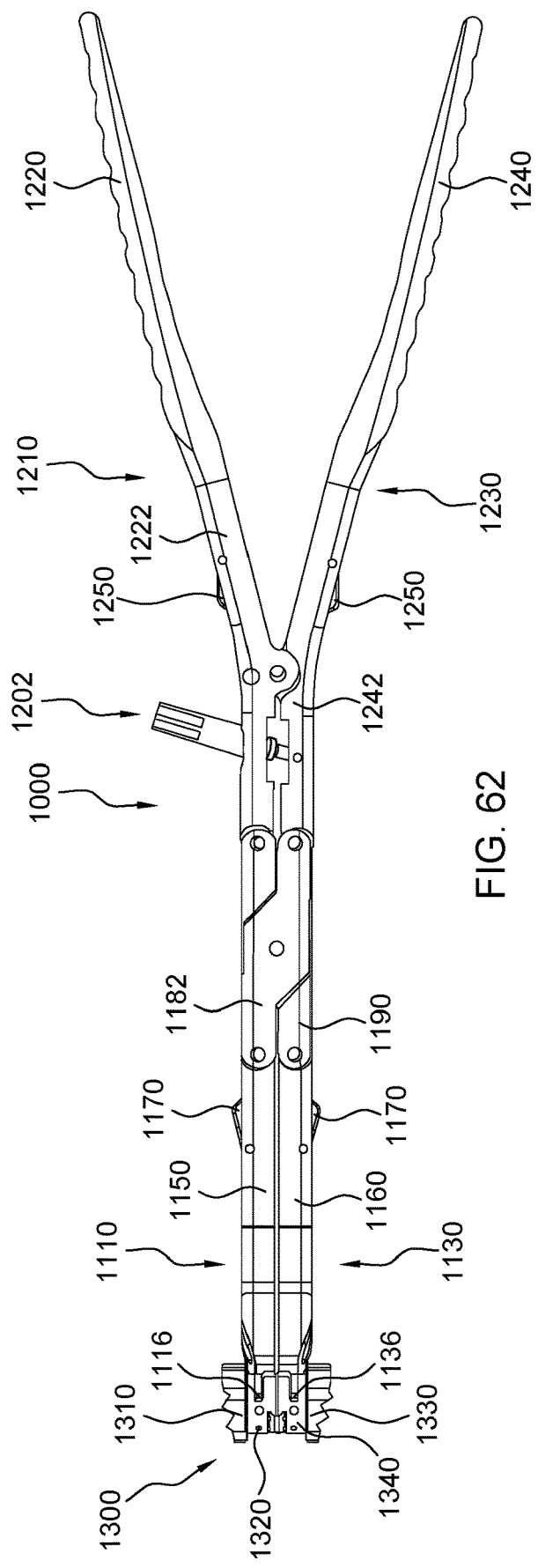
FIG. 62 is a side view of the distraction instrument of FIG. 48 engaging a portion of a spinal implant in an insertion position, in accordance with an aspect of the present invention.
Figure 63:
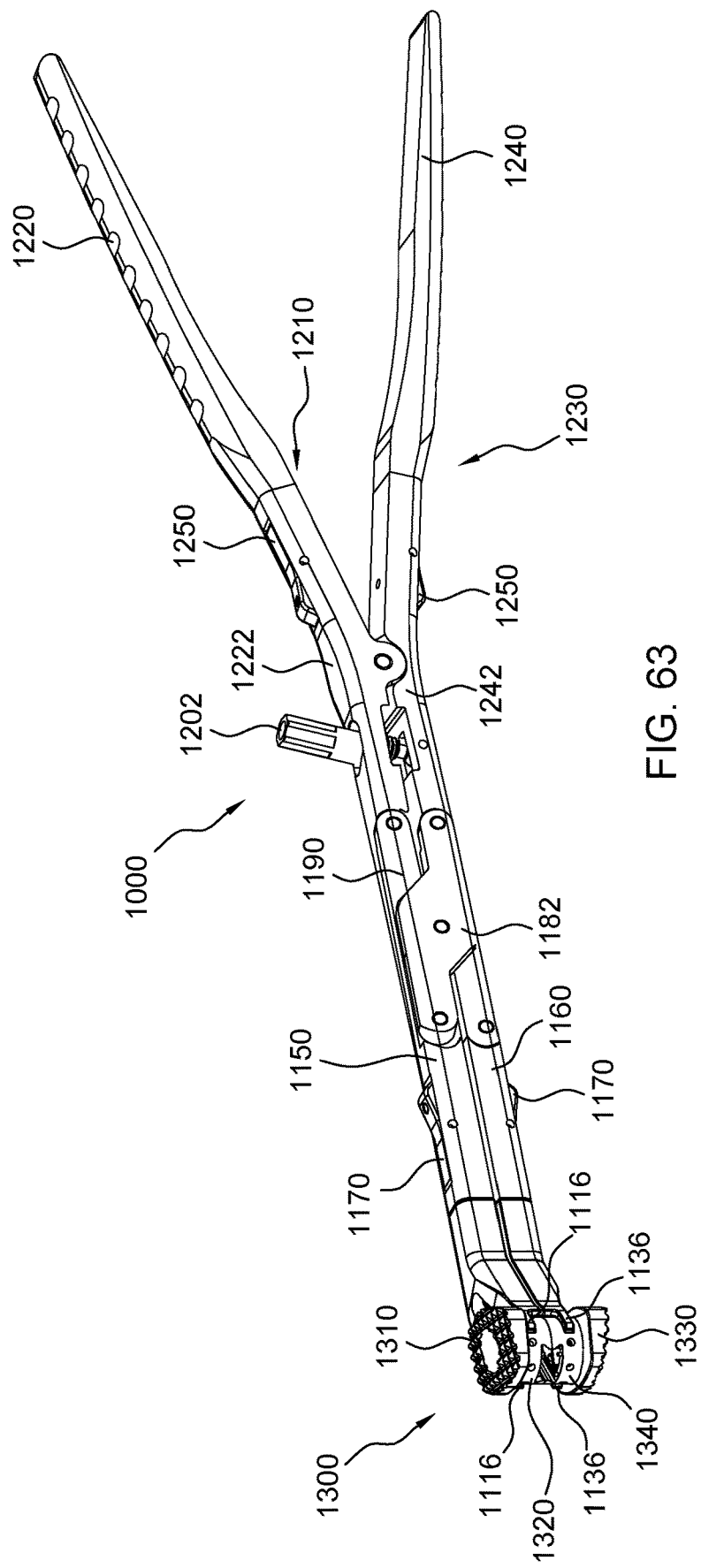
FIG. 63 is a perspective view of the distraction instrument and spinal implant of FIG. 62, in accordance with an aspect of the present invention.

The first arm 1150 of the distraction instrument 1000, as shown in FIGS. 57, 58, and 61, may include a lever opening 1152 positioned near the first end of the first arm 1150 on a top surface. The lever opening 1152 may be sized and shaped to receive a lever 1170. The first arm 1150 may also include an inserter member hole 1154 for receiving the coupling member 1120 of the first inserter member 1110. In addition, the first arm 1150 may include a groove 1156 extending through the side of the first arm 1150 for coupling to a first end 1184 of the first member 1182. The groove 1156 may be positioned, for example, near a center point of the first arm 1150. The first arm 1150 may further include an opening 1158 near the second end of the first arm 1150 for coupling to the second end 1194 of the second member 1190 and the first handle 1210.

The second arm 1160 of the distraction instrument 1000, as shown in FIGS. 57 and 58, and the reverse of first arm 1150 in FIG. 61, may include a lever opening 1162 positioned near the first end of the second arm 1160 on a bottom surface. The lever opening 1162 may be sized and shaped to receive a lever 1170. The second arm 1160 may also include an inserter member hole 1164 for receiving the coupling member 1140 of the second inserter member 1130. In addition, the second arm 1160 may include a groove 1166 extending through the side of the second arm 1160 for coupling to a first end 1192 of the second member 1190. The groove 1166 may be positioned, for example, near a center point of the second arm 1160. The second arm 1160 may further include an opening 1168 near the second end for coupling to the second end 1186 of the first member 1182 and the second handle 1230.

As shown in FIGS. 49, 51, 53, 54, 57, and 58, the distraction system 1180 of the distraction instrument 1000 may include the first member 1182, the second member 1190, and a center hinge pin 1200. The first member 1182 may include a first end 1184, a second end 1186, and a center opening 1188. The first end 1184 may include an opening for receiving a hinge pin 1198 for moveably coupling the first end 1184 of the first member 1182 to the groove 1156 of the first arm 1150. The second end 1186 may include an opening for receiving a hinge pin 1198 for rotatably coupling the first member 1182 to the second end of the second arm 1160 and the first end of the second handle 1230. The second member 1190 may include a first end 1192, a second end 1194, and a center opening 1196. The first end 1192 may include an opening for receiving a hinge pin 1198 for moveably coupling the first end 1192 of the second member 1190 to the groove 1166 of the second arm 1160. The second end 1194 may include an opening for receiving a hinge pin 1198 for rotatably coupling the second member 1190 to the second end of the first arm 1150 and the first end of the first handle 1210. The center opening 1188 of the first member 1182 may be aligned with the center opening 1196 of the second member 1190 and the center hinge pin 1200 may rotatably couple the first member 1182 to the second member 1190.

Figure 54:
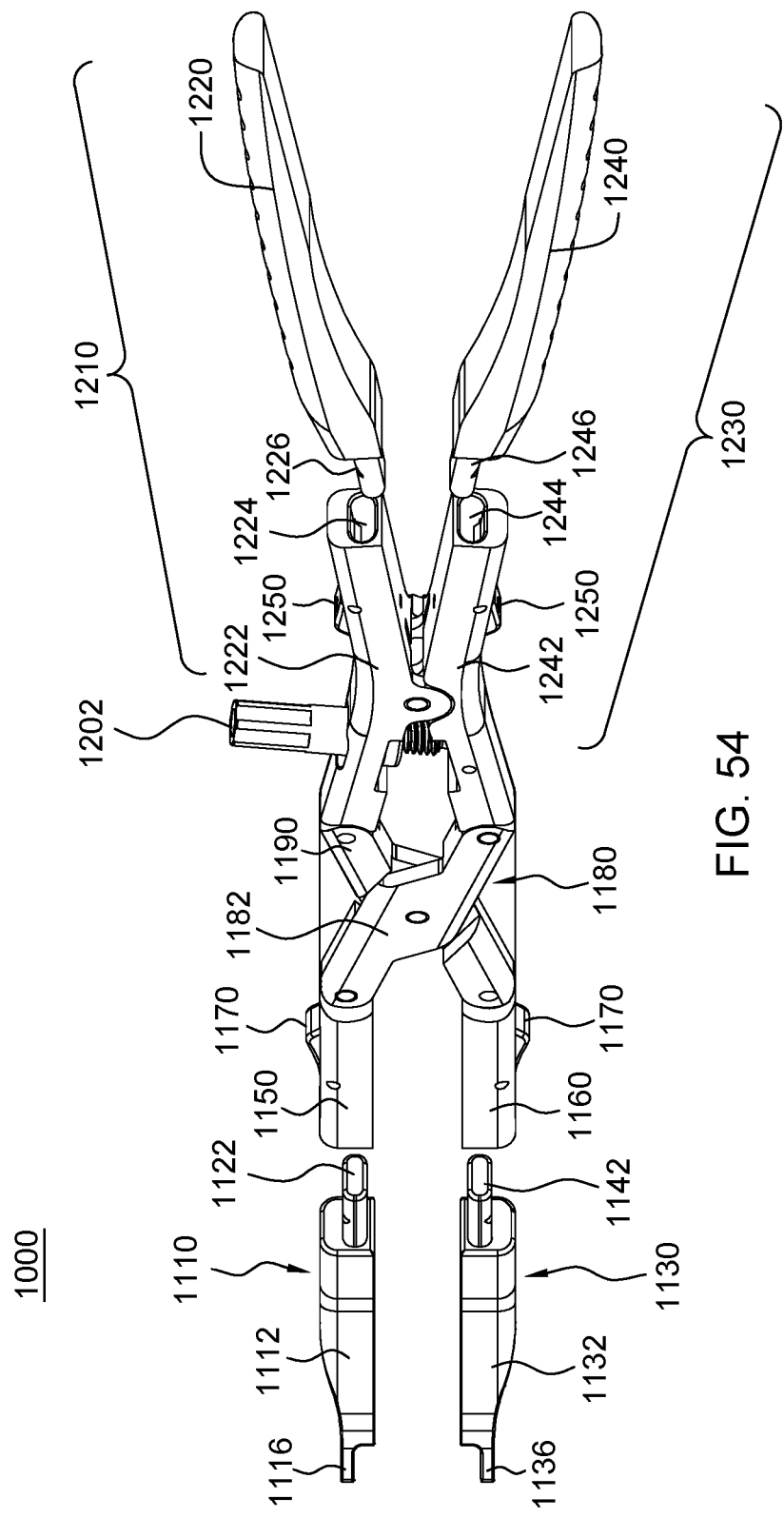
FIG. 54 is a partially exploded back perspective view of the distraction instrument of FIG. 48, in accordance with an aspect of the present invention.

As shown in FIGS. 48-54 and 56-58, the first handle 1210 may include a body 1222 removeably coupled to a handle portion 1220. The body 1222 may include an opening 1212 at a first end, a stop member channel 1214 near the first end, a lever opening 1216 near the second end, and a hinge member 1218 positioned near a center point of the body 1222. As shown in FIG. 54, the body 1222 may also include an inserter member hole 1224 at the second end. The inserter member hole 1224 may extend into the lever opening 1216. The handle portion 1220 may include a coupling member 1226 extending away from the first end of the handle portion 1220. The coupling member 1226 may include a locking groove 1228 on a top surface. The coupling member 1226 may be inserted into the inserter member hole 1224 and extend into the lever opening 1216. A lever 1250 may be coupled to the lever opening 1216 to secure the coupling member 1226 of the handle portion 1220 to the body 1222. The lever 1250 may have a locking protrusion 1252 at a first end, a button 1254 at a second end, and a hinge member 1256 positioned near a center point of the lever 1250. The locking protrusion 1252 may engage the locking groove 1228 of the coupling member 1226 to secure the handle portion 1220 to the body 1222. The handle portion 1220 may be released from the body 1222 by depressing the button 1254.

Figure 56:
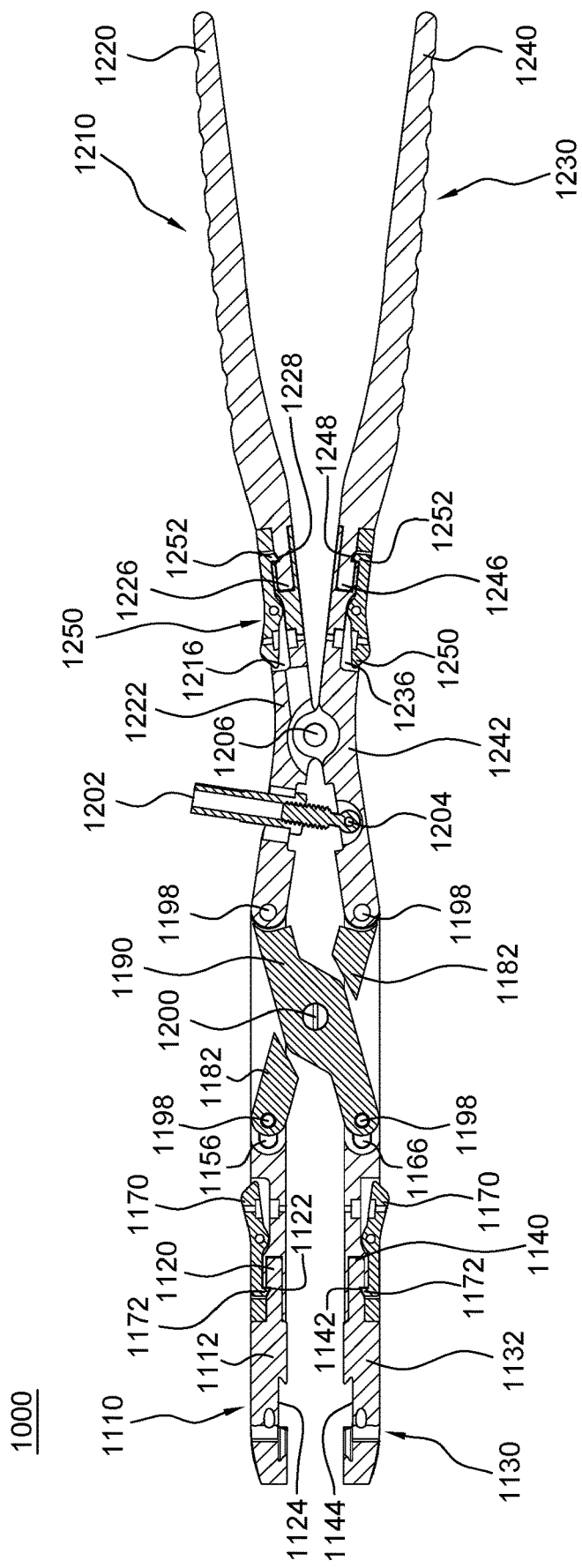
FIG. 56 is a cross-sectional view of the distraction instrument of FIG. 48 taken along line 56-56 in FIG. 52, in accordance with an aspect of the present invention.

As shown in FIGS. 48-54 and 56-58, the second handle 1230 may include a body 1242 removeably coupled to a handle portion 1240. As shown in FIGS. 56 and 58, the body 1242 may include an opening 1232 at a first end, a stop member channel 1234 near the first end, a lever opening 1236 near the second end, and a hinge member 1238 positioned near a center point of the body 1242. As shown in FIG. 54, the body 1242 may also include an inserter member hole 1244 at the second end. The inserter member hole 1244 may extend into the lever opening 1236. The handle portion 1240 may include a coupling member 1246 extending away from the first end of the handle portion 1240. The coupling member 1246 may include a locking groove 1248 on a bottom surface. The coupling member 1246 may be inserted into the inserter member hole 1244 and extend into the lever opening 1236. A lever 1250 may be coupled to the lever opening 1236 to secure the coupling member 1246 of the handle portion 1240 to the body 1242. The lever 1250 may have a locking protrusion 1252 at a first end, a button 1254 at a second end, and a hinge member 1256 positioned near a center point of the lever 1250. The locking protrusion 1252 may engage the locking groove 1248 of the coupling member 1246 to secure the handle portion 1240 to the body 1242. The handle portion 1240 may be released from the body 1242 by depressing the button 1254.

Figure 71:
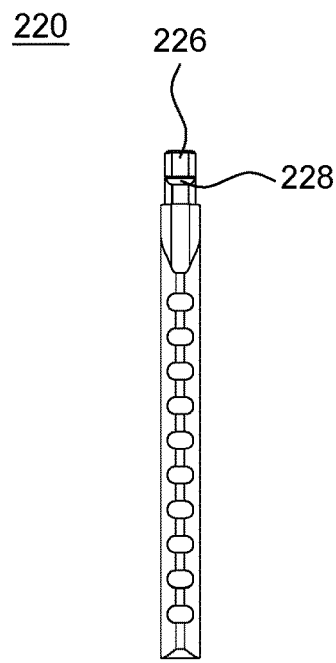
FIG. 71 is a top view of a handle member of the distraction instrument of FIG. 48, in accordance with an aspect of the present invention.
Figure 72:
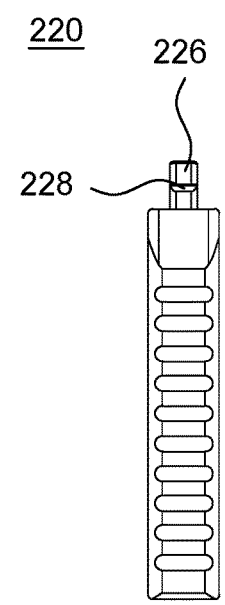
FIG. 72 is a top view of an alternative handle member for the distraction instrument of FIG. 48, in accordance with an aspect of the present invention.
Figure 73:
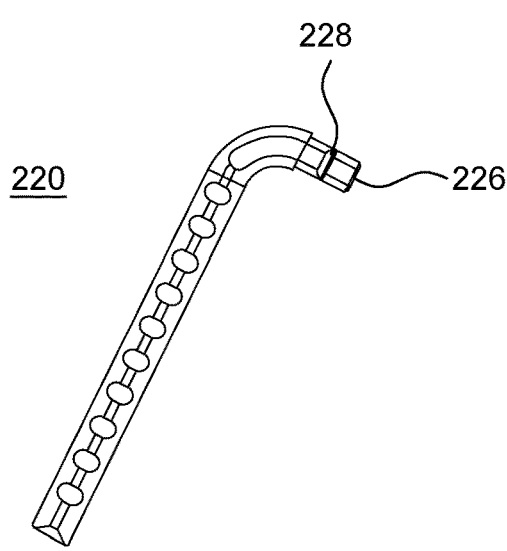
FIG. 73 is a top view of another handle member for the distraction instrument of FIG. 48, in accordance with an aspect of the present invention.

Alternative first and second handle portions 1220, 1240 are also contemplated. For example, as shown in FIGS. 71-73, the handle portions 1220, 1240 may come in multiple sizes with varying widths and heights. In addition, the handle portions 1220, 1240 may be, for example, angled along the longitudinal axis, as shown in FIG. 73. The handle portions 1220, 1240 may be, for example, angled in a range of approximately 0° to 90°. The handle portions 1220, 1240 may also come in multiple lengths, widths, and shapes.

As shown in FIGS. 48-52 and 56, the distraction instrument 1000 may be assembled by attaching the first body 1222 to the second body 1242 with a pin 1206. The coupling portion 1204 of the stop member 1202 may be secured in the stop member channel 1234 and the stop member 1202 may extend through the stop member channel 1214. The opening 1212 of the first body 1222 may be aligned with the opening 1158 of the first arm 1150 and the opening in the second end 1194 of the second member 1190. A pin 1198 may be inserted through the openings to attach the first body 1222, the first arm 1150, and the second member 1190. In addition, the opening 1232 of the second body 1242 may be aligned with the opening 1168 of the second arm 1160 and the opening in the second end 1186 of the first member 1182. A pin 1198 may be inserted through the openings to attach the second body 1242, the second arm 1160, and the first member 1182. The center opening 1188 of the first member 1182 is aligned with the center opening 1196 of the second member 1190. Then, a center hinge pin 1200 is inserted into the openings 1188, 1196 to moveably couple the first member 1182 to the second member 1196.

Next, with continued reference to FIGS. 48-52 and 56, the opening in the first end 1184 of the first member 1182 is aligned with the groove 1156 of the first arm 1150 and a pin 1198 may be used to moveably secure the first member 1182 to the first arm 1150. The pin 1198 may translate within the groove 1156 to allow for the distraction instrument 1000 to expand. The opening in the first end 1192 of the second member 1190 is aligned with the groove 1166 of the second arm 1160 and a pin 1198 may be used to moveably secure the second member 1190 to the second arm 1160. The pin 1198 may translate within the groove 1166 to allow for the distraction instrument 1000 to expand. In addition, a lever 1170 may be inserted into the lever opening 1152 in the first arm 1150 and a lever 1170 may be inserted into the lever opening 1162 in the second arm 1160. In addition, a lever 1250 may be inserted into the lever opening 1216 in the first body 1222 and a lever 1250 may be inserted into the lever opening 1236 in the second body 1242. The levers 1170, 1250 may be secured in the lever openings 1152, 1162, 1216, 1236 using pins, screws, rivets, or the like that allows the levers 1170, 1250 to move with respect to the lever openings 1152, 1162, 1216, 1316.

Then, as shown in FIGS. 57-58 and 69-70, a spring 1128 may be inserted into the opening 1114 in the first inserter member 1110 and a threaded rod 1126 may be inserted through the hole 1118 and the spring 1128. In addition, a spring 1148 may be inserted into the opening 1134 in the second inserter member 1130 and a threaded rod 1146 may be inserted through the hole 1138 and the spring 1148. The threaded rods 1126, 1146 may engage a portion of a spinal implant, as shown in FIGS. 62-68. The springs 1128, 1148 may preload the threaded rods 1126, 1146 to enable the threaded rods 1126, 1146 to disengage from the spinal implants. Thus, once the threaded rods 1126, 1146 disengage from the spinal implants, the springs 1128, 1148 will cause the threaded rods 1126, 1146 to retract into the inserter members 1110, 1130 to fully disengage from the spinal implants. Referring now to FIGS. 48-52 and 56, the first inserter member 1110 may be coupled to the first arm 1150 by inserting the coupling member 1120 into the inserter member hole 1154. The locking protrusion 1172 may engage the locking groove 1122 to secure the first inserter member 1110 to the first arm 1150. The second inserter member 1130 may be coupled to the second arm 1160 by inserting the coupling member 1140 into the inserter member hole 1164. The locking protrusion 1172 may engage the locking groove 1142 to secure the second inserter member 1130 to the second arm 1160. The first handle portion 1220 may be coupled to the first body 1222 by inserting the coupling member 1226 into the inserter member hole 1224. The locking protrusion 1252 may engage the locking groove 1228 to secure the handle portion 1220 to the first body 1222. The second handle portion 1240 may be coupled to the second body 1242 by inserting the coupling member 1246 into the inserter member hole 1244. The locking protrusion 1252 may engage the locking groove 1248 to secure the handle portion 1240 to the second body 1242.

Figure 74:
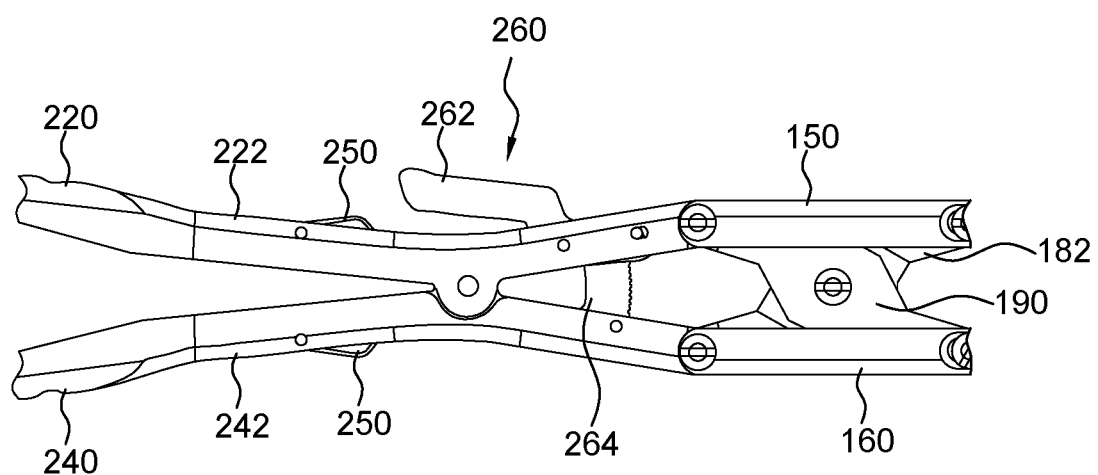
FIG. 74 is a side view of the distraction instrument of FIG. 48 with an alternative stop member, in accordance with an aspect of the present invention.
Figure 75:
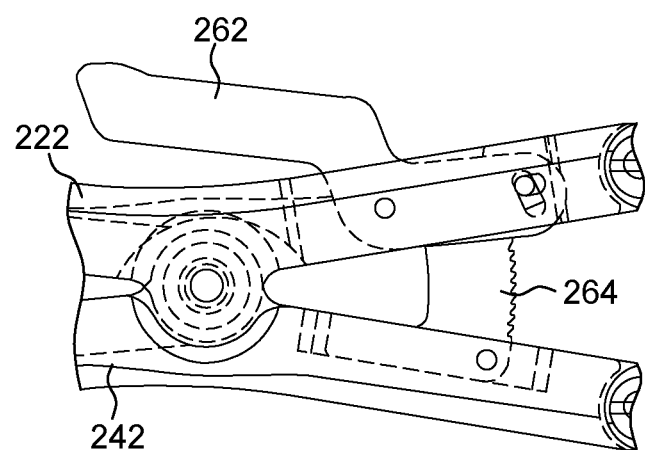
FIG. 75 is a detailed side view of the stop member of FIG. 74, in accordance with an aspect of the present invention.

An alternative stop member 1202 is shown in FIGS. 74-75. The alternative stop member 1202 may be a ratcheting mechanism 1260. The ratcheting mechanism 1260 may include, for example, a lever arm 1262, a tooth member 1264 for engaging the lever arm 1262, and a toothed clutch 1266 to assist with maintaining the position of the inserter members 1110, 1130 after expansion and distraction of the patient's spine.

Figure 68:
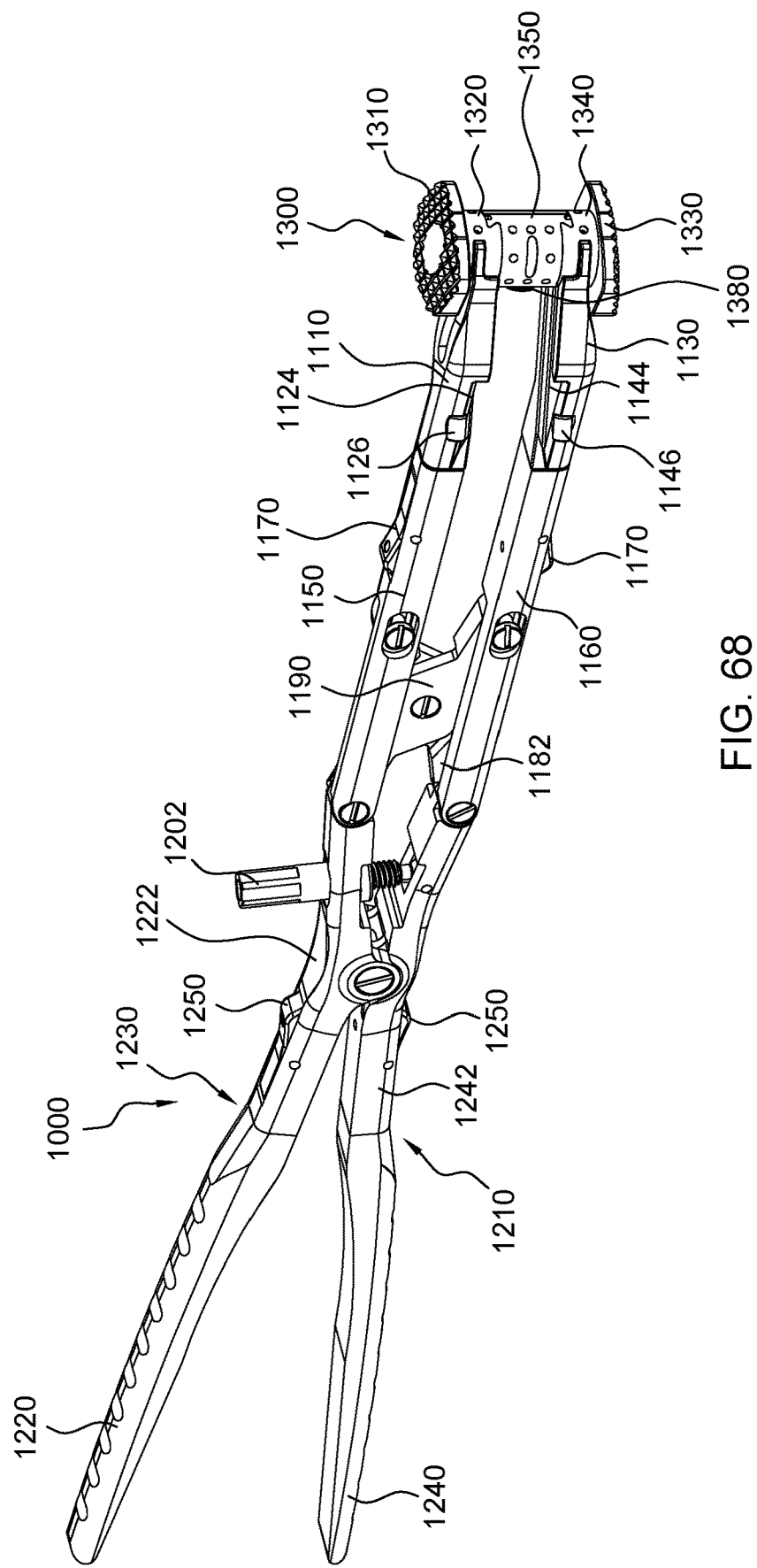
FIG. 68 is a perspective view of the distraction instrument of FIG. 48 in an expanded position and engaging the assembled spinal spacer implant, in accordance with an aspect of the present invention.
Figure 76:
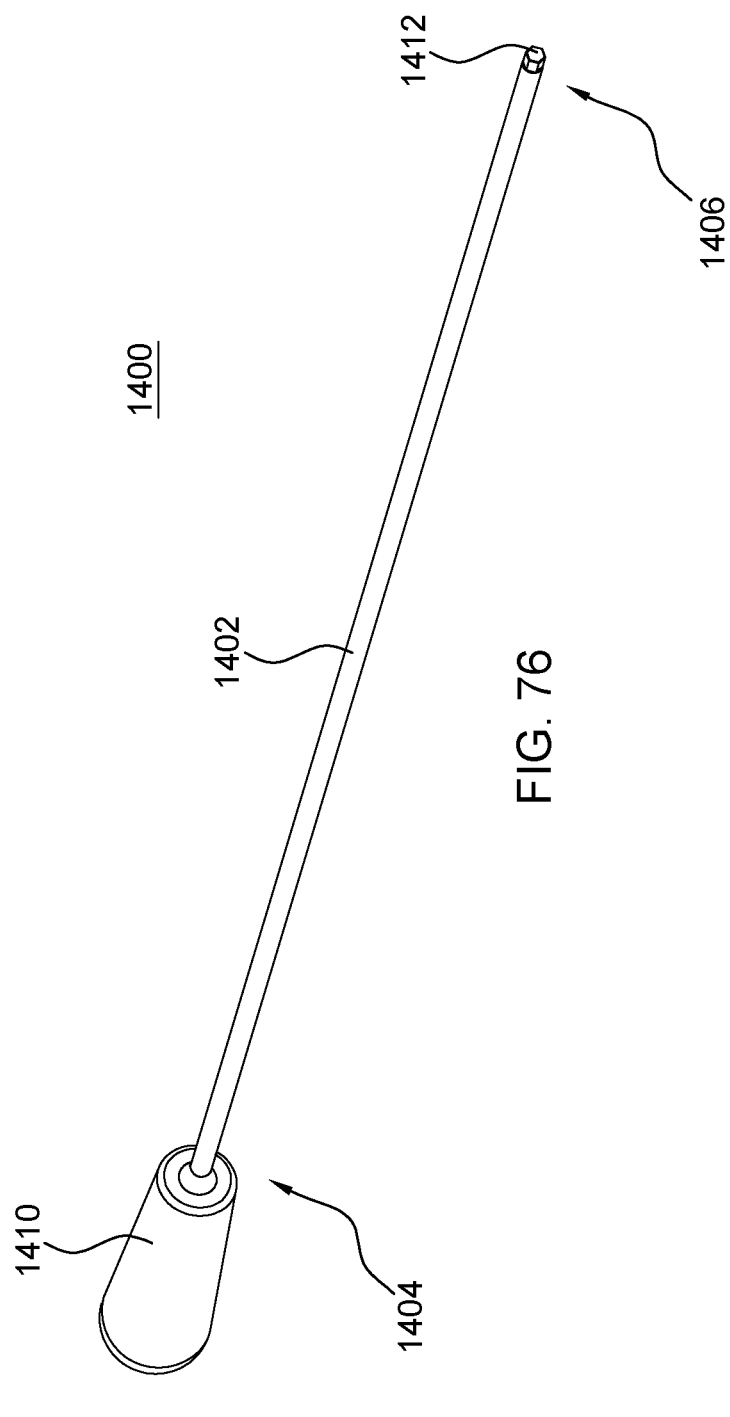
FIG. 76 is a perspective view of a locking driver instrument for locking the spacer in position between the first and second portions of the spinal implant, in accordance with an aspect of the present invention.
Figure 77:
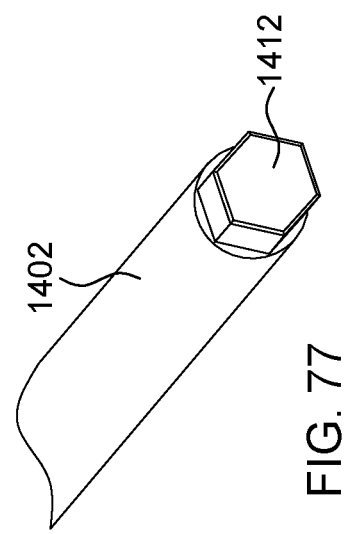
FIG. 77 is a perspective view of a first end of the locking driver instrument of FIG. 76, in accordance with an aspect of the present invention.

Referring now to FIGS. 76 and 77, a locking driver instrument 1400 for locking the spacer 1350 in position between the first and second portions 1320, 1340 of the spinal implant 1300 is shown. The locking driver instrument 1400 may include a shaft 1402 with a handle 1410 at a first end 1404 and a driver tip 1412 at a second end 1406. The shaft 1402 may have, for example, a length to enable insertion of the spacer 1350 through the distraction instrument 1000 and into position between the first and second portions 1320, 1340 of the spinal implant 1300. The driver tip 1412 may be shaped to engage the locking member 1380, as shown in FIG. 68, in the spacer 1350. The driver tip 1412 may have a cross-section with, for example, a hexagonal shape, a polygonal shape, or other shape that corresponds to the shape of the opening in the locking member 1380. After the driver tip 1412 is inserted into the locking member 1380, the handle 1410 of the locking driver instrument 1400 may be rotated to secure the spacer 1350 in position between the first and second portions 1320, 1340. Alternatively, the handle 1410 of the locking driver instrument 1400 may be rotated in the opposite direction to disengage the locking member 1380 and release the spacer 1350 from the first and second portions 1320, 1340, for example, to replace the spacer 1350 or the entire spinal implant 1300.

Figure 66:
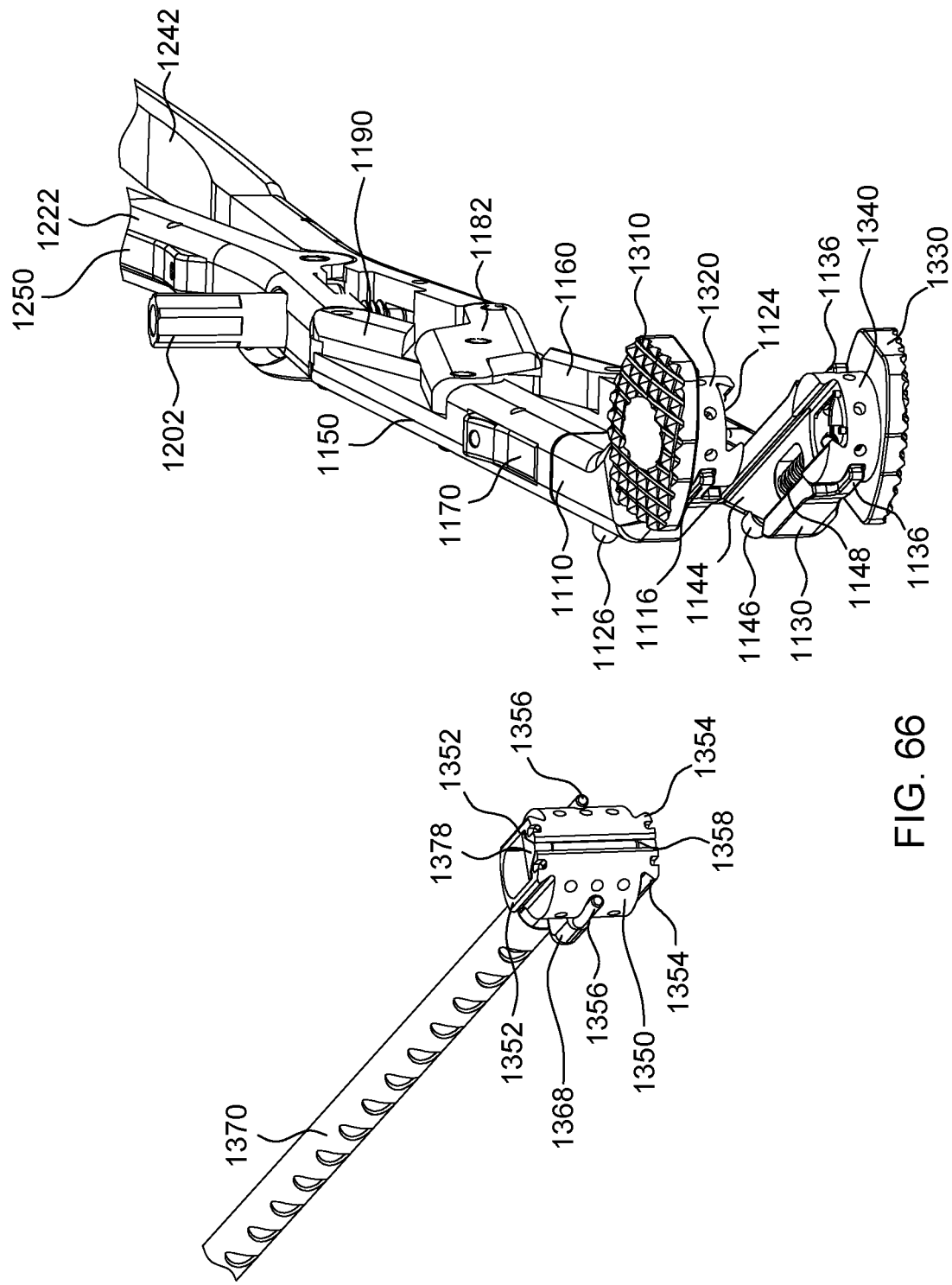
FIG. 66 is a detailed perspective view of the first end of the spinal spacer assembly of FIG. 65, in accordance with an aspect of the present invention.
Figure 78:
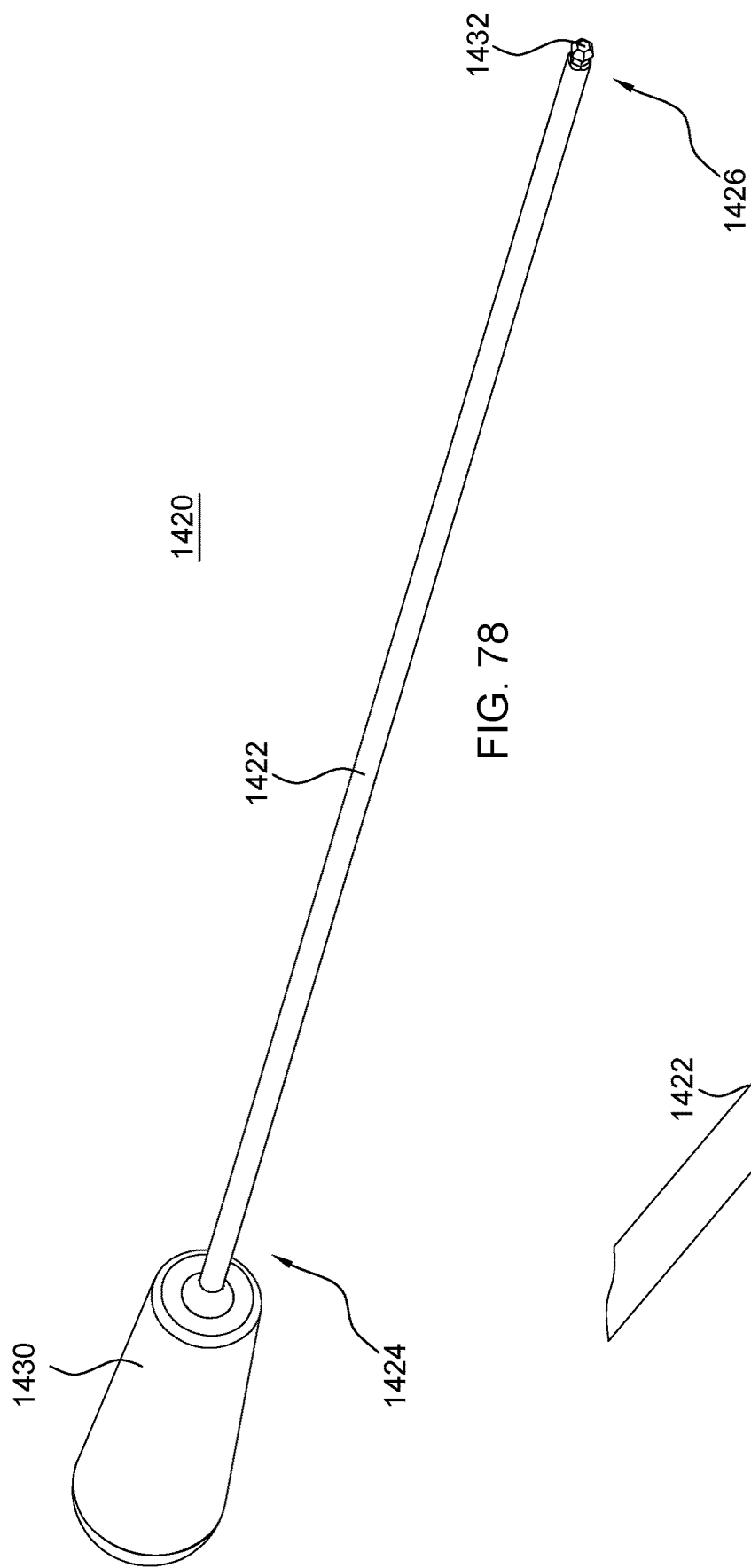
FIG. 78 is a perspective view of a threaded rod driver instrument for securing the threaded rods of the distraction instrument of FIG. 48 to the spinal implant, in accordance with an aspect of the present invention.
Figure 79:
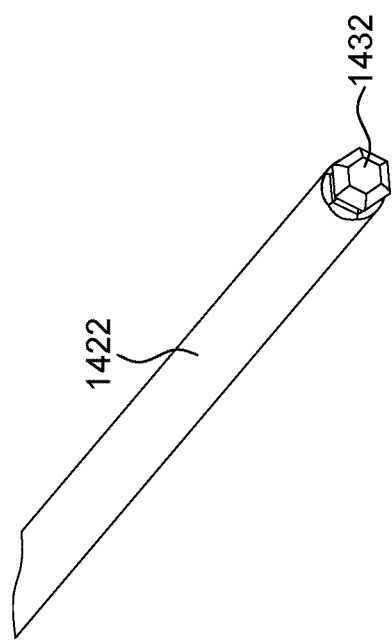
FIG. 79 is a perspective view of a first end of the threaded rod driver instrument of FIG. 78, in accordance with an aspect of the present invention.

A threaded rod driver instrument 1420 is shown in FIGS. 78 and 79. The threaded rod driver instrument 1420 may be used to secure the threaded rods 1126, 1146 of the distraction instrument 1000 to the spinal implant 1300, as shown in FIGS. 66 and 68. The threaded rod driver instrument 1420 may include a shaft 1422 with a handle 1430 at a first end 1424 and a driver tip 1432 at a second end 1426. The shaft 1422 may have, for example, a length to enable insertion into the patient during surgery to disengage the threaded rods 1126, 1146 from the first and second portions 1320, 1340 of the spinal implant 1300. The driver tip 1432 may be shaped to engage the head of the threaded rods 1126, 1146. The driver tip 1432 may have a cross-section with, for example, a hexagonal shape, a polygonal shape, or other shape that corresponds to the shape of the opening in the head of the threaded rods 1126, 1146. The driver tip 1432 may also have a curved or rounded end to, for example, allow for insertion into the head of the threaded rods 1126, 1146 at multiple angles. The driver tip 1432 may be inserted into the heads of the threaded rods 1126, 1146 and the handle 1430 rotated in a first direction to engage the first and second portions 1320, 1340 of the spinal implant 1300 to secure the first and second portions 1320, 1340 to the distraction instrument 1000. Once the spinal implant 1300 is inserted between the patient's vertebrae, the driver tip 1432 of the threaded rod driver instrument 1420 may be inserted into each of the heads of the threaded rods 1126, 1146. The handle 1430 of the driver instrument 1420 may then be rotated in a second direction to disengage the threaded end of the threaded rods 1126, 1146 from the first and second portions 1320, 1340 of the spinal implant 1300.

Figure 80:
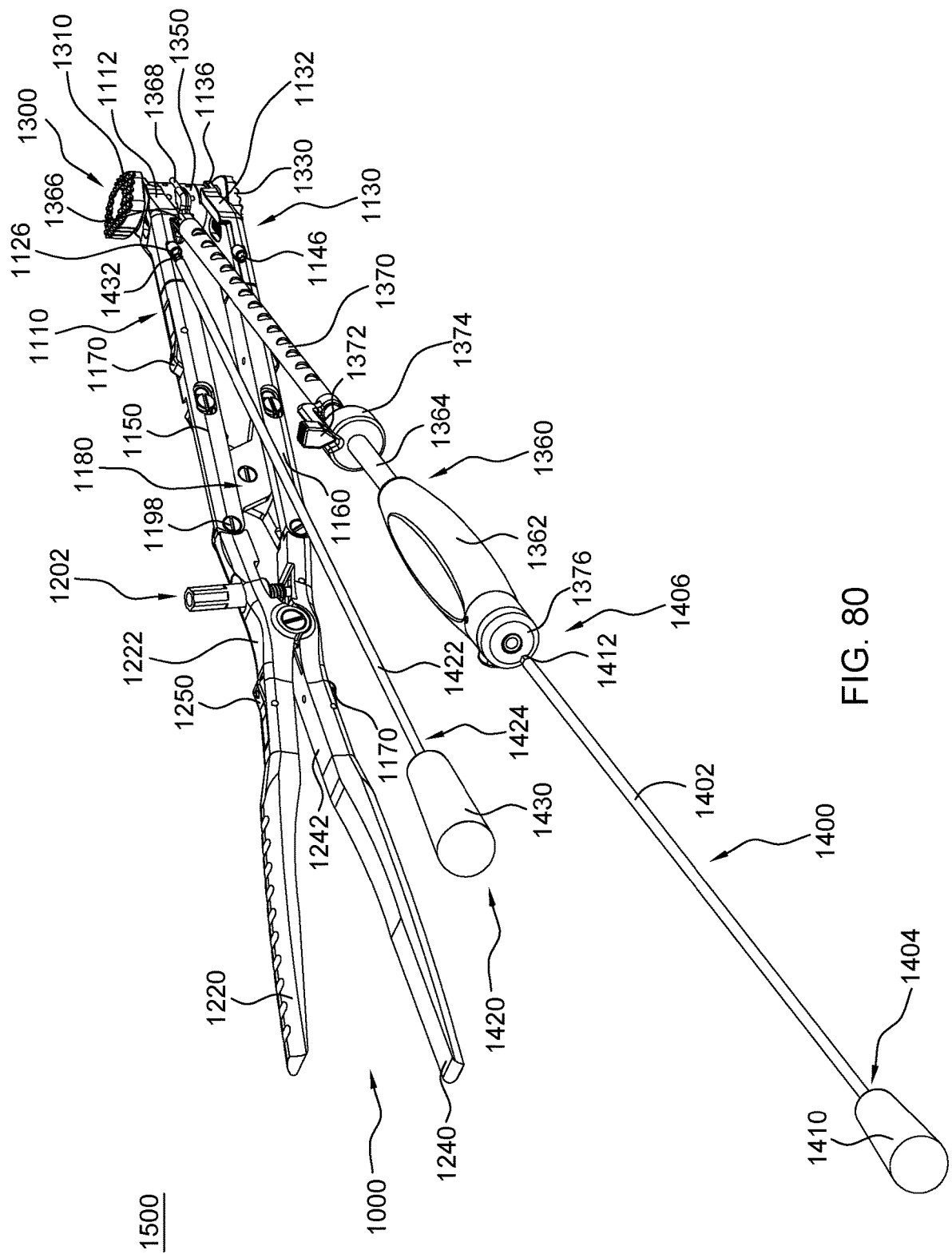
FIG. 80 is a partially exploded perspective view of a vertebral body replacement system including the distraction instrument, the spinal implant, and the spacer inserter of FIG. 67, the locking driver instrument of FIG. 76, and the threaded rod driver instrument of FIG. 78, in accordance with an aspect of the present invention.
Figure 81:
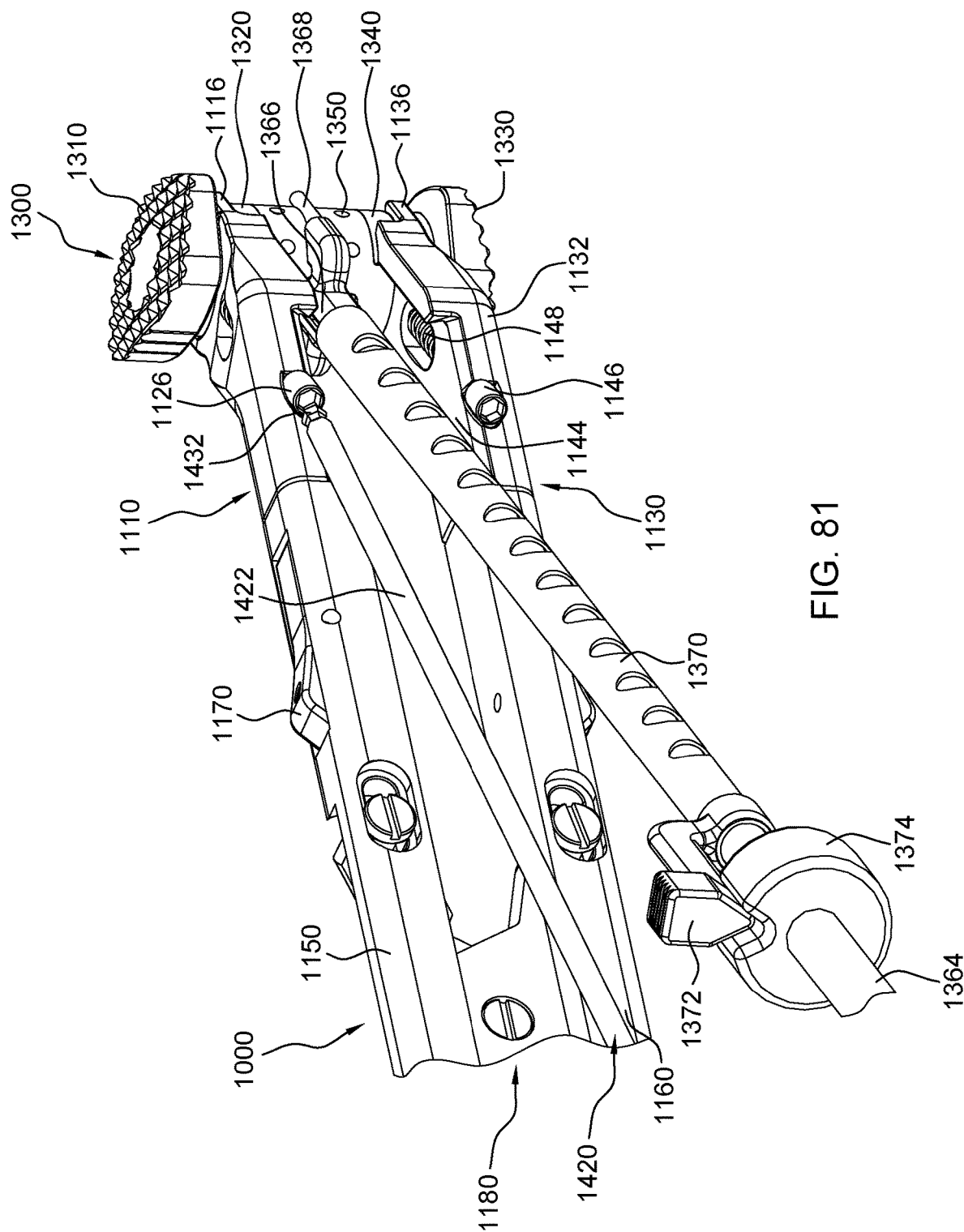
FIG. 81 is a detailed perspective view of the first end of the vertebral body replacement system of FIG. 80, in accordance with an aspect of the present invention.
Figure 82:
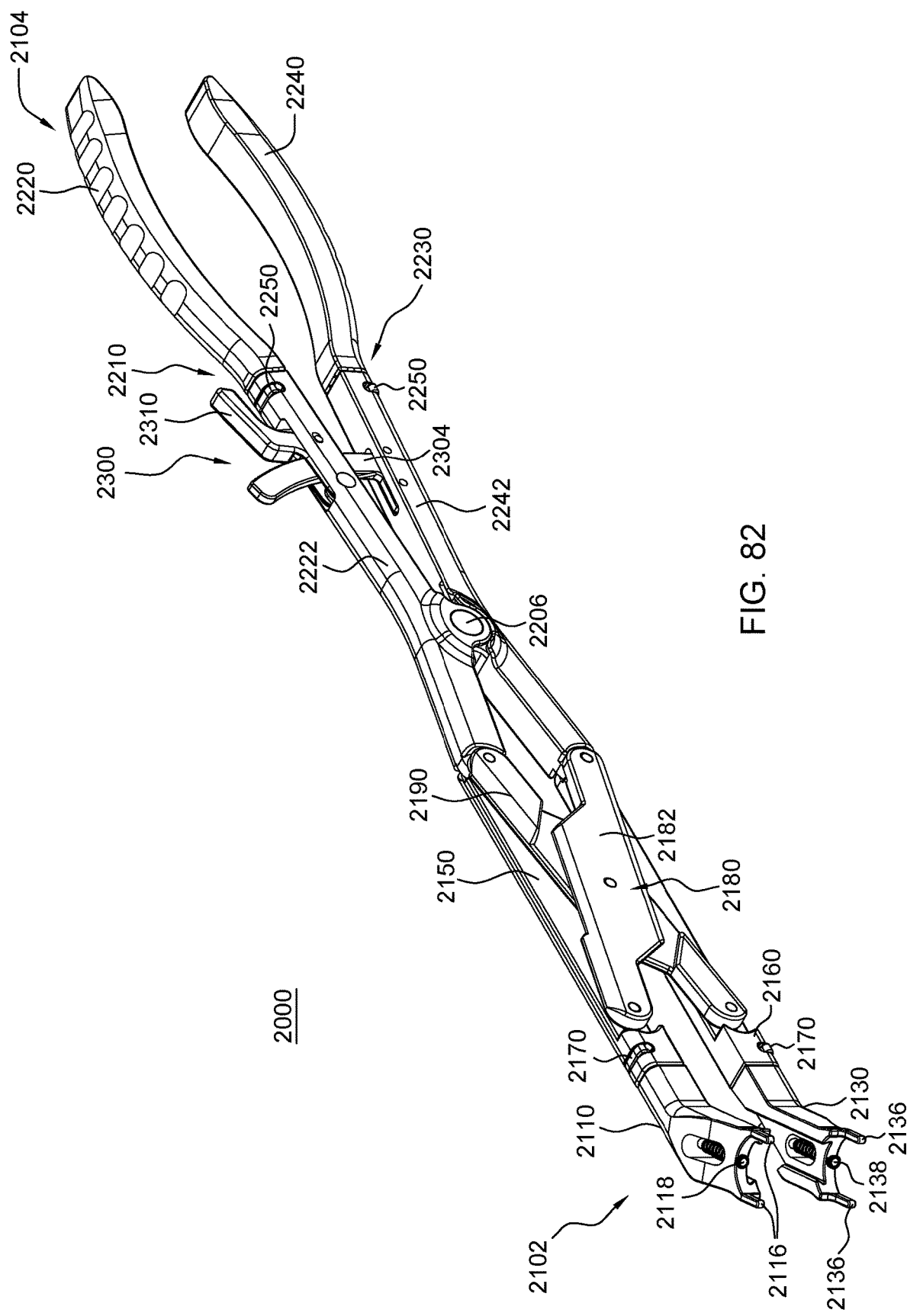
FIG. 82 is a first front perspective view of another distraction instrument of a vertebral body replacement system in an open position, in accordance with an aspect of the present invention.

Referring now to FIGS. 80 and 81, a vertebral body replacement system 1500 including the distraction instrument 1000, the spinal implant 1300, the spacer inserter 1360, the locking driver instrument 1400, and the threaded rod driver instrument 1420 is shown. The distraction instrument 1000, the spinal implant 1300, the spacer inserter 1360, the locking driver instrument 1400, and the threaded rod driver instrument 1420 are as described above with reference to FIGS. 48-79.

Figure 64:
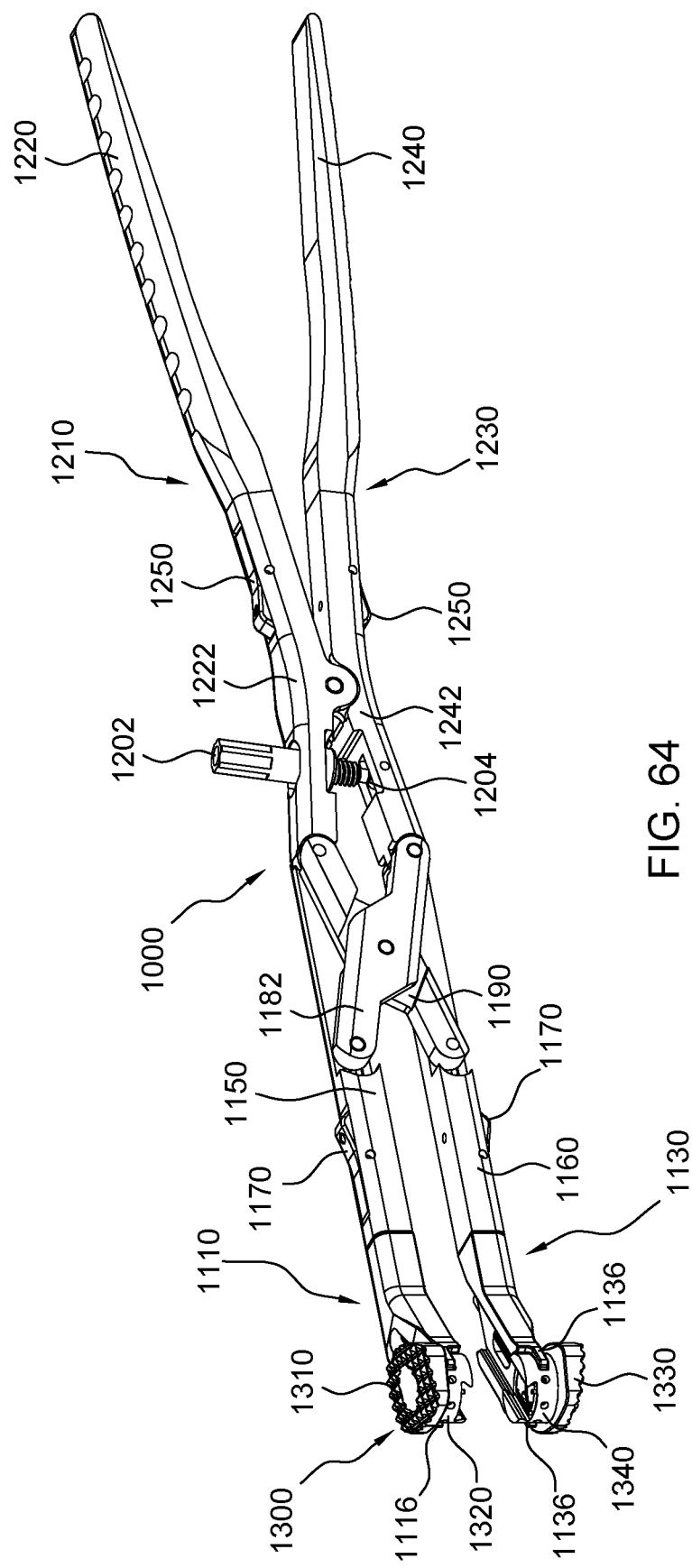
FIG. 64 is a perspective view of the distraction instrument and spinal implant of FIG. 62 in an expanded position, in accordance with an aspect of the present invention.
Figure 65:
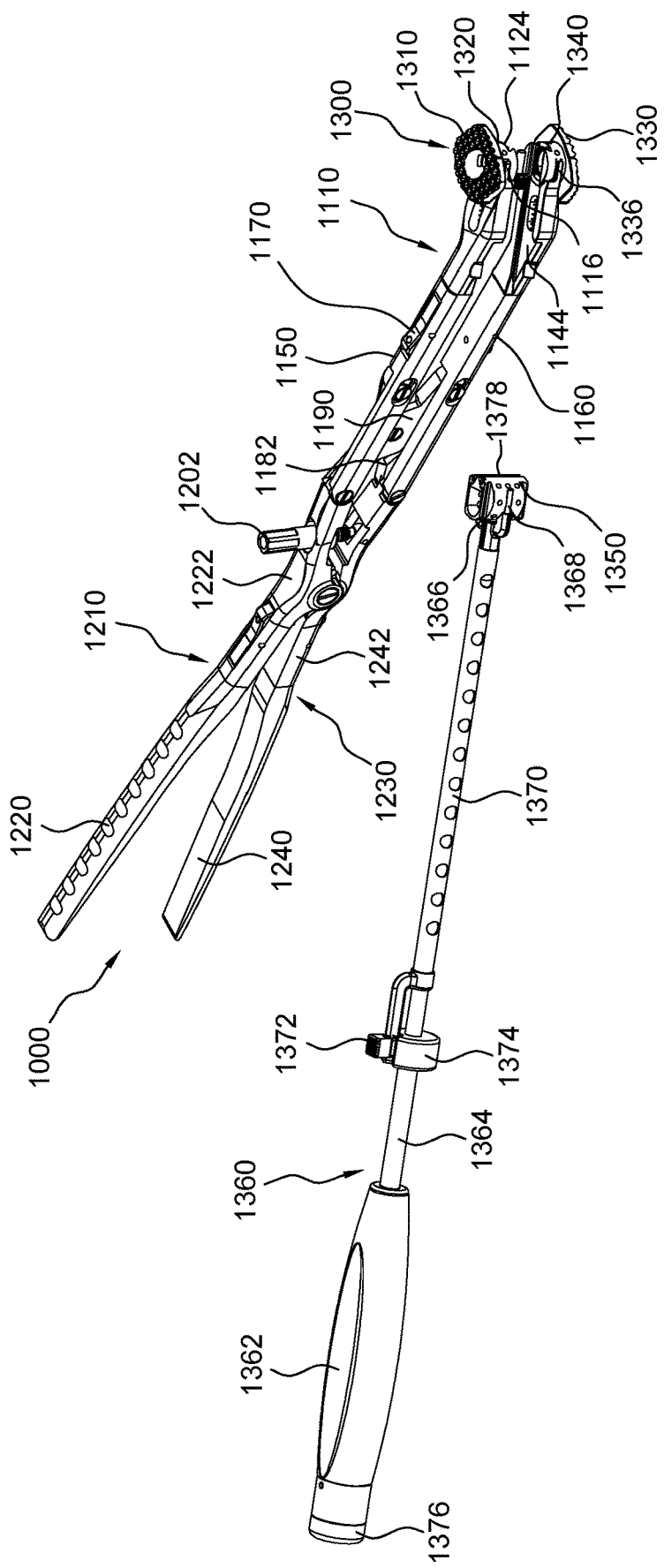
FIG. 65 is a partially exploded perspective view of a spinal spacer assembly including the distraction instrument and spinal implant of FIG. 62 and a spacer inserter and spinal implant spacer, in accordance with an aspect of the present invention.

Referring now to FIGS. 62-68, a method of inserting a spinal implant 1300 is shown. The spinal implant 1300 may include a first end plate 1310, a first portion 1320, a second end plate 1330, a second portion 1340, and a spacer 1350. Although not shown, it is also contemplated that the implant 1300 may include, for example, the first portion 1320, the second portion 1340, and the spacer 1350. In the alternative embodiment, a first end of the first portion 1320 and a second end of the second portion 1340 may have a bone contacting surface with, for example, a coating or textured surface to allow for bone ingrowth or ongrowth. The first end plate 1310 may couple to the first portion 1320 and the second end plate 1330 may couple to the second portion 1340. The distraction instrument 1000 may engage the first and second portions 1320, 1340 of the spinal implant 1300. The first portion 1320 may include grooves (not shown) to engage the protrusions 1116 of the first inserter member 1110 for insertion of the spinal implant. Once the first portion 1320 engages the protrusions 1116, the threaded rod 1126 may be inserted into the first portion 1320 with the threaded rod driver instrument 1420. The second portion 1340 may also include grooves (not shown) to engage the protrusions 1136 of the second inserter member 1130 for insertion of the spinal implant. Once the second portion 1340 engages the protrusions 1136, the threaded rod 1146 may be inserted into the second portion 1340 with the threaded rod driver instrument 1420. After the first and second portions 1320, 1340 are coupled to the distraction instrument 1000, the spinal implant 1300 may be inserted into a patient's spine. When the spinal implant 1300 is positioned in the desired position, the spinal implant 1300 may be expanded to realign the patient's spine. The inserter members 1110, 1130 may be expanded by squeezing the handle portions 1220, 1240. As the handle portions 1220, 1240 are squeezed the inserter members 1110, 1130 expand away from each other, separating the first and second portions 1320, 1340 of the spinal implant 1300, as shown in FIGS. 64-66. The stop member 1202 maintains the expanded position of the inserter members 1110, 1130 and the first and second portions 1320, 1340 while the spacer 1350 is inserted between the first and second portions 1320, 1340.

Figure 67:
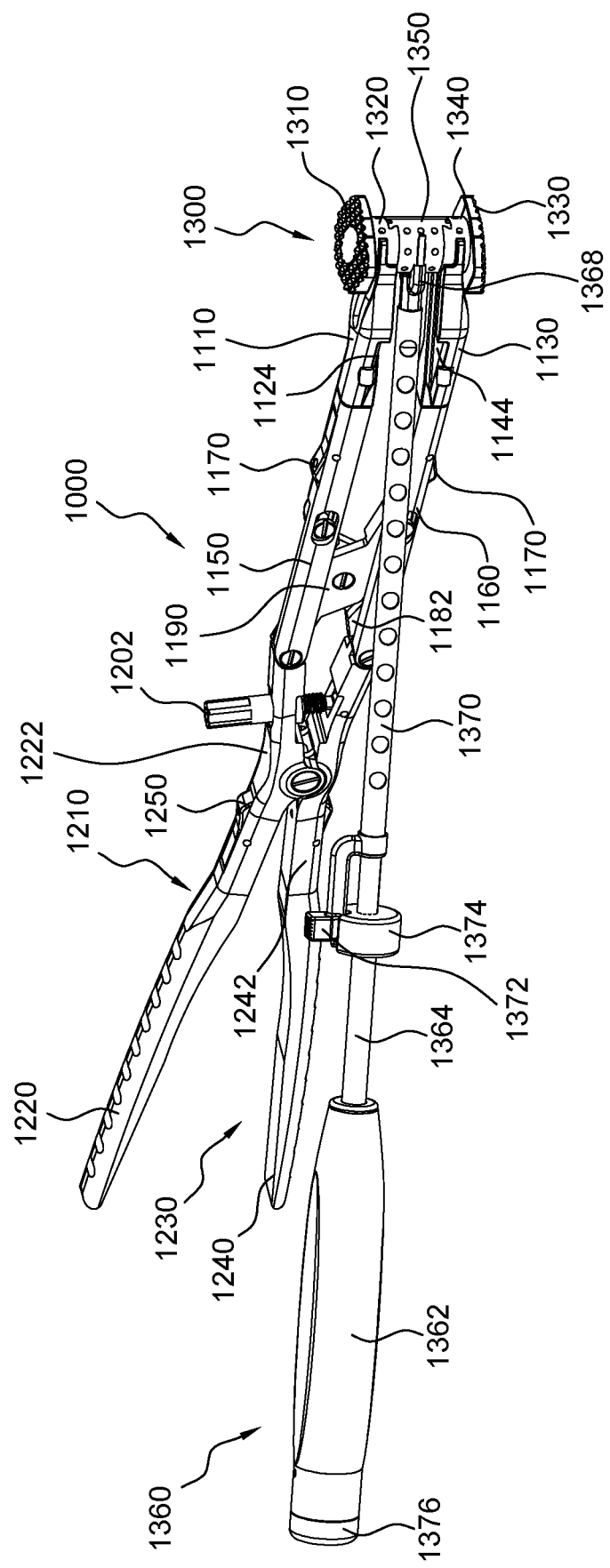
FIG. 67 is a perspective view of the spinal spacer assembly of FIG. 65 with the distraction instrument of FIG. 48 in an expanded position and the spacer inserter and spacer positioned in the spinal implant, in accordance with an aspect of the present invention.

After the first and second portions 1320, 1340 are in the desired position, the size of the space between the first and second portions 1320, 1340 may be measured and a spacer 1350 may be selected. The spacer 1350 may be coupled to a spacer inserter 1360, as shown in FIGS. 65-67. The spacer inserter 1360 may include a handle 1362 with an actuation mechanism (not shown). The actuation mechanism may be configured to enable the engagement shaft 1364 to be secured in a first position wherein an implant spacer member 1350 is secured to the proximal end 1366 of the engagement shaft 1364 for insertion into a patient. Then upon actuation of the actuation mechanism (not shown), the handle 1362 is released and free to move in a longitudinal direction along the shaft 1364. Once the handle 1362 is released, the surgeon may use the handle 1362 as a slide or slap hammer to facilitate tapping of the spacer member 1350 through the tracks 1124, 1144 in the first and second members 1320, 1340. Once in the desired position, the spacer inserter 1360 may be removed leaving an intermediate spacer member 1350 of the implant 1300 in the patient. The spacer inserter 1360 may also include an alignment head 1368 for alignment of the intermediate spacer member 1350 on the spacer inserter 1360 for insertion into the patient. The spacer inserter 1360 may further include a movable housing 1370 with a coupled tab 1372 to assist in the alignment and insertion of the intermediate spacer member 1350 between the first and second inserter members 1110, 1130 of the distraction mechanism 1000. The spacer inserter 1360 may also include an engagement member 1374 positioned on the housing 1370. The tab 1372 may be axially translated toward the center spacer 1350. The housing 1370 may be actuated by the tab 1372 to engage the spacer 1350. As the tab 1372 is moved forward the housing 1370 slides forward and causes the arms of the alignment head 1368 to move closer together to engage the spacer 1350. The arms of the alignment head 1368 clamp onto the spacer 1350 during insertion. Once the spacer 1350 is inserted between the first and second members 1320, 1340 of the implant 1300, the tab 1372 may be moved in a rearward direction towards the handle 1362 moving the housing 1370 towards the handle 1362 and releasing the arms of the alignment head 1368. After the arms of the alignment head 1368 disengage from the spacer 1350, the spacer inserter 1360 may be removed from the patient. The engagement member 1374 remains static as the tab 1372 is translated and assists with preventing the tab 1372 and the housing 1370 from rotating. In addition, the engagement member 1374 may act as a positive stop for the handle 1362 when translated to assist with the insertion of the center spacer 1350. The handle 1362 may translate on the engagement shaft 1364 when the button 304, such as shown in FIGS. 23-24, is depressed, to move the center spacer 1350 through the insertion tracks 1124, 1144. If there is excessive friction between the center spacer 1350 and the insertion tracks 1124, 1144 which makes it difficult to push the center spacer 1350 by hand, then the handle 1362 may be tamped by, for example, a slap hammer (not shown) to overcome the friction and move the center spacer 1350 into position between the first and second portions 1320, 1340. The spacer inserter 1360 may further include an end portion 1376 coupled to the engagement shaft 1364, which may be the point of contact when tamping is necessary.

The intermediate spacer 1350 may be of the type described above with reference to implant 400. The intermediate spacer 1350 may include a first end and a second end. The intermediate spacer 1350 may include a coupling mechanism 1352 for engaging the first member 1320 on the first end and a coupling mechanism 1354 for engaging the second member 1340 on the second end. The coupling mechanisms 1352, 1354 may be, for example, the male portions of a dovetail mechanism. The intermediate spacer 1350 may also include at least one instrument coupling mechanism (not shown) on a side of the exterior surface of the intermediate spacer 1350. The instrument coupling mechanisms 1356 may be, for example, grooves or channels on the exterior side surfaces of the spacer 1350. The grooves 1356 are sized and shaped to engage the alignment head 1368 of the spacer inserter 1360.

The spacer 1350 may further include a locking member 1380, as shown in FIG. 68, on the front for securing the spacer 1350 within the spinal implant 1300. The locking member 1380 may have, for example, a permanently integral member (not shown) or alternatively, a removable member (not shown). The locking member 1380 may be used to secure or lock the spacer 1350 to the first and second members 1320, 1340, once the spacer 1350 is fully inserted between the first and second members 1320, 1340. In addition, the spacer 1350 may include a gap or channel 1358 on the back of the spacer 1350 to allow for slight deflection of the spacer 1350 during insertion between the first and second members 1320, 1340.

After the spacer 1350 is selected and coupled to the spacer inserter 1360, the coupling mechanism 1352 may be aligned with the spacer insertion track 1124 and the coupling mechanism 1354 may be aligned with the spacer insertion track 1144. The spacer 1350 may be slid along the tracks 1124, 1144 and into engagement with the first and second members 1320, 1340, as shown in FIGS. 67-68. Once the spacer 1350 is positioned between the first and second members 1320, 1340, the locking driver instrument 1400 may be inserted through the center cannulation of the spacer inserter 1360 to engage the locking member 1380 in the spacer 1350, as shown in FIG. 80. The locking member 1380 may then be rotated to expand the locking member 1380, for example, a wedge piece, and engage the spacer 1350 causing the gap 1358 to expand or increase. As the locking member 1380 expands the gap 1358, the spacer 1350 is mechanically locked to the first and second members 1320, 1340 by increasing the friction between the coupling mechanisms 1352, 1354 of the spacer 1350 and the tracks 1124, 1144 of the first and second members 1320, 1340. A locking mechanism, for example, a fastener (not shown), a button such as button 424, 426 as described in greater detail above, or the like, may be activated to secure the spacer 1350 to the first and second members 1320, 1340. Next, the threaded rods 1126, 1146 may be disengaged from the first and second implant members 1320, 1340 using the threaded rod driver instrument 1420 and the distraction instrument 1000 may be removed from the patient. Finally, the patient's incision may be closed.

Referring now to FIGS. 82-86, another distraction instrument 2000 is shown. The distraction instrument 2000 may include a first inserter member 2110 and second inserter member 2130 at a first end 2102. The distraction instrument 2000 may also include a first arm 2150 coupled to the first inserter member 2110 and second arm 2160 coupled to the second inserter member 2130. The distraction instrument 2000 may further include a distraction system 2180 engaging the first and second arms 2150, 2160. In addition, the distraction instrument 2000 may include a first handle 2210 and a second handle 2230 at the second end 2104. The first handle 2210 may be coupled to the second end of the first arm 2150 and the second member 2190 and the second handle 2230 may be coupled to the second end of the second arm 2160 and the first member 2182. The distraction instrument 2000 may also include a ratcheting mechanism 2300 positioned to engage the first and second handles 2210, 2230 to hold the distraction instrument 2000 in the expanded position.

Figure 86:
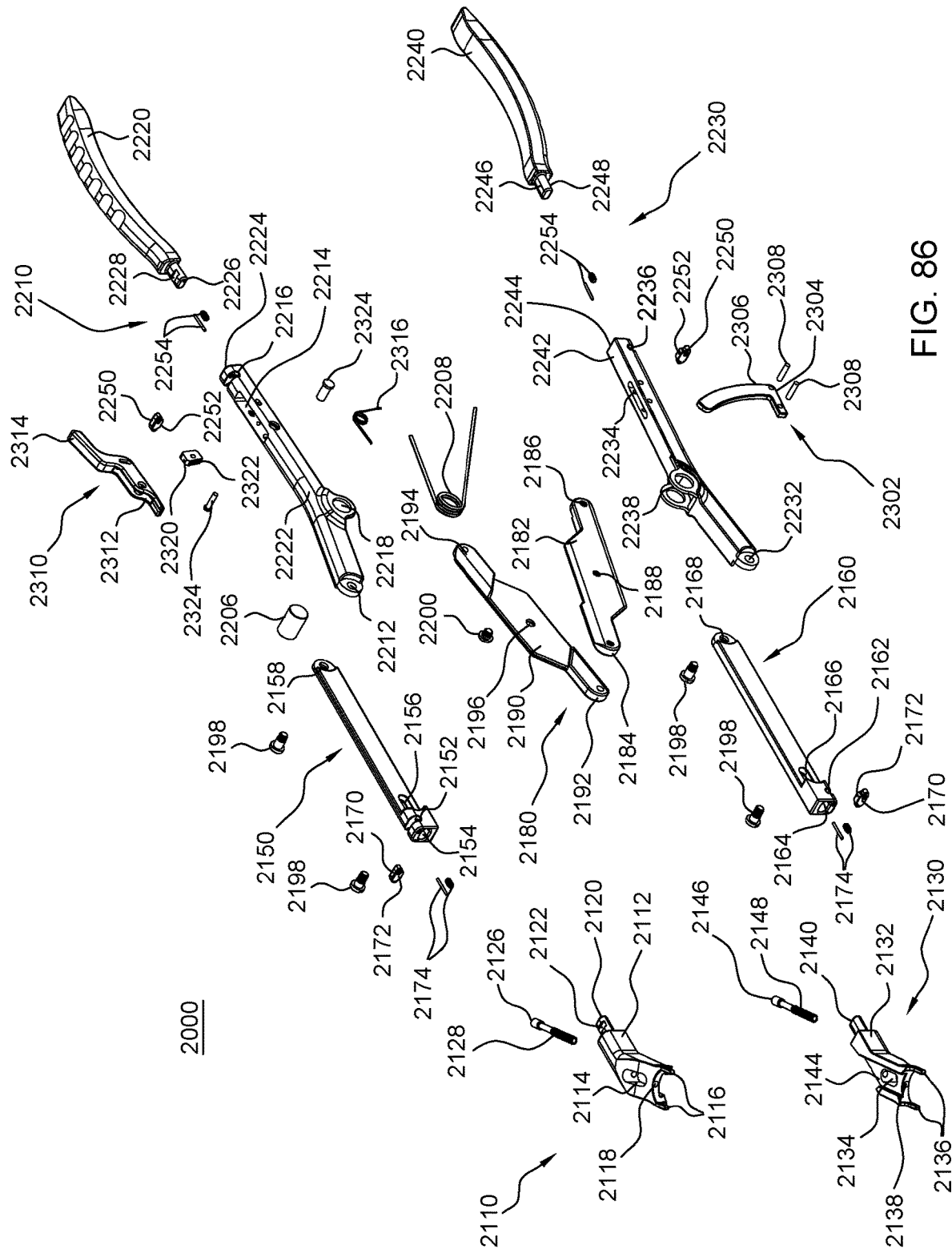
FIG. 86 is an exploded view of the distraction instrument of FIG. 82, in accordance with an aspect of the present invention.

As shown in FIG. 86, the first inserter member 2110 may be of the type described above with reference to the first inserter member 1110. The first inserter member 2110 may include a body 2112 with a first opening 2114, engagement protrusions 2116, a hole 2118, a coupling member 2120 with a locking groove 2122, and an insertion track 2124, which may be of the type described above with reference to the body 2112 with the first opening 2114, the engagement protrusions 2116, the hole 2118, the coupling member 2120 with the locking groove 2122, and the insertion track 2124 and which will not be described again here for brevity sake.

The second inserter member 2130 may be of the type described above with reference to the second inserter member 1130. The second inserter member 2130 may include a body 2132 with a first opening 2134, engagement protrusions 2136, a hole 2138, a coupling member 2140 with a locking groove 2142, and an insertion track 2144, which may be of the type described above with reference to the body 2132 with the first opening 2134, the engagement protrusions 2136, the hole 2138, the coupling member 2140 with the locking groove 2142, and the insertion track 2144 and which will not be described again here for brevity sake.

Figure 83:
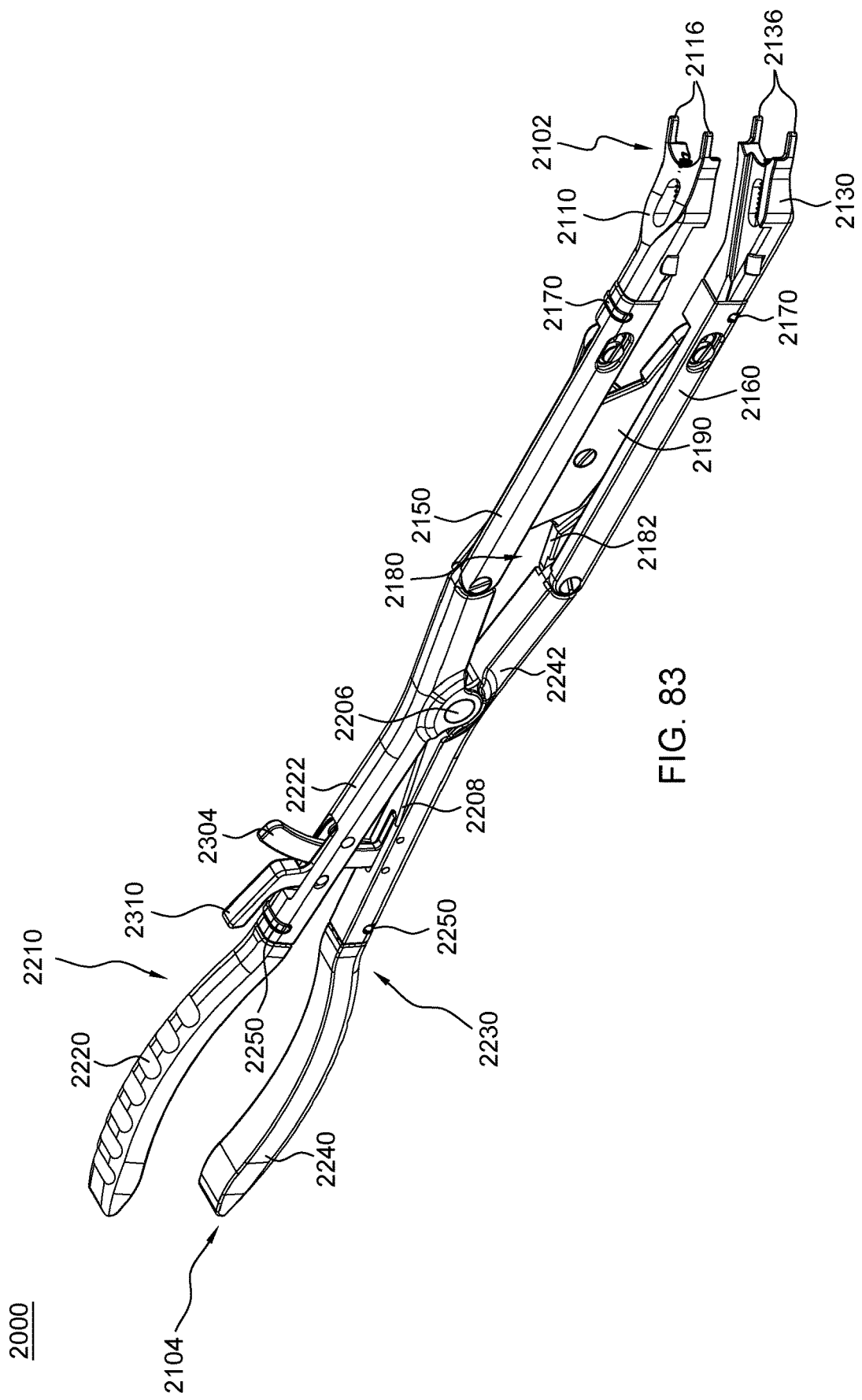
FIG. 83 is a second front perspective view of the distraction instrument of FIG. 82, in accordance with an aspect of the present invention.
Figure 84:
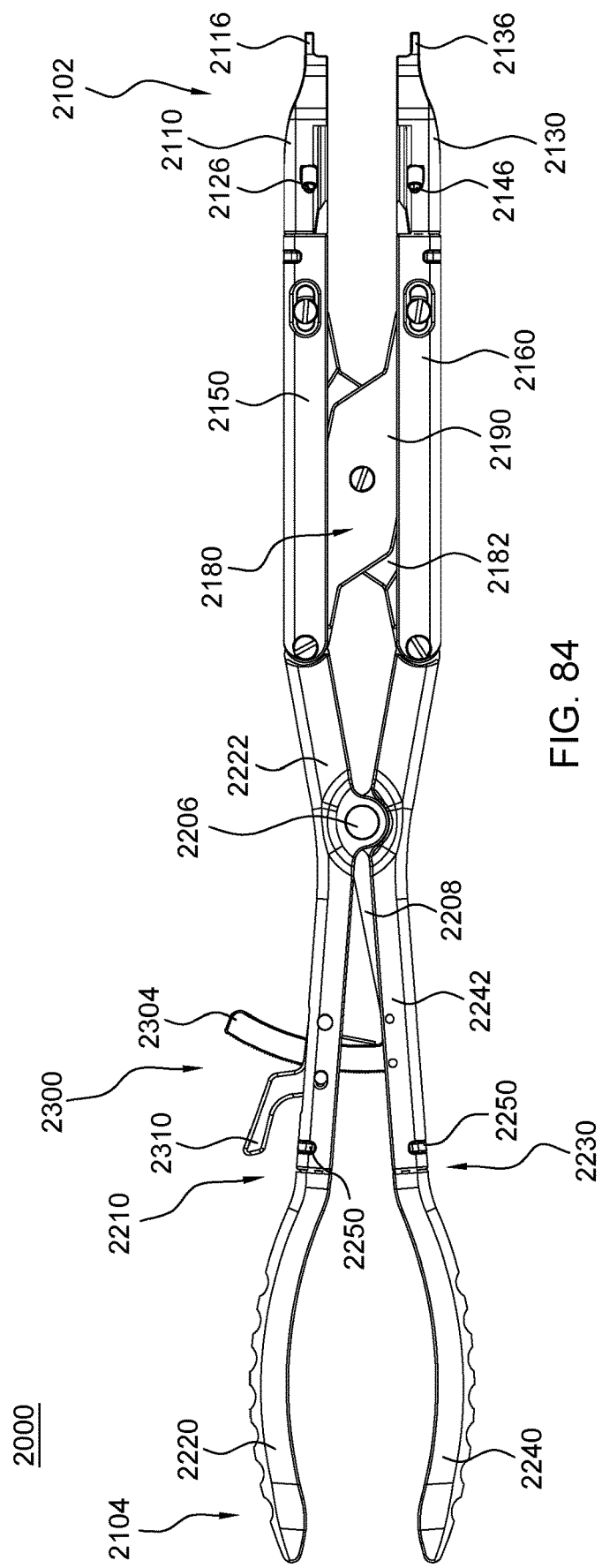
FIG. 84 is a side view of the distraction instrument of FIG. 82, in accordance with an aspect of the present invention.
Figure 85:
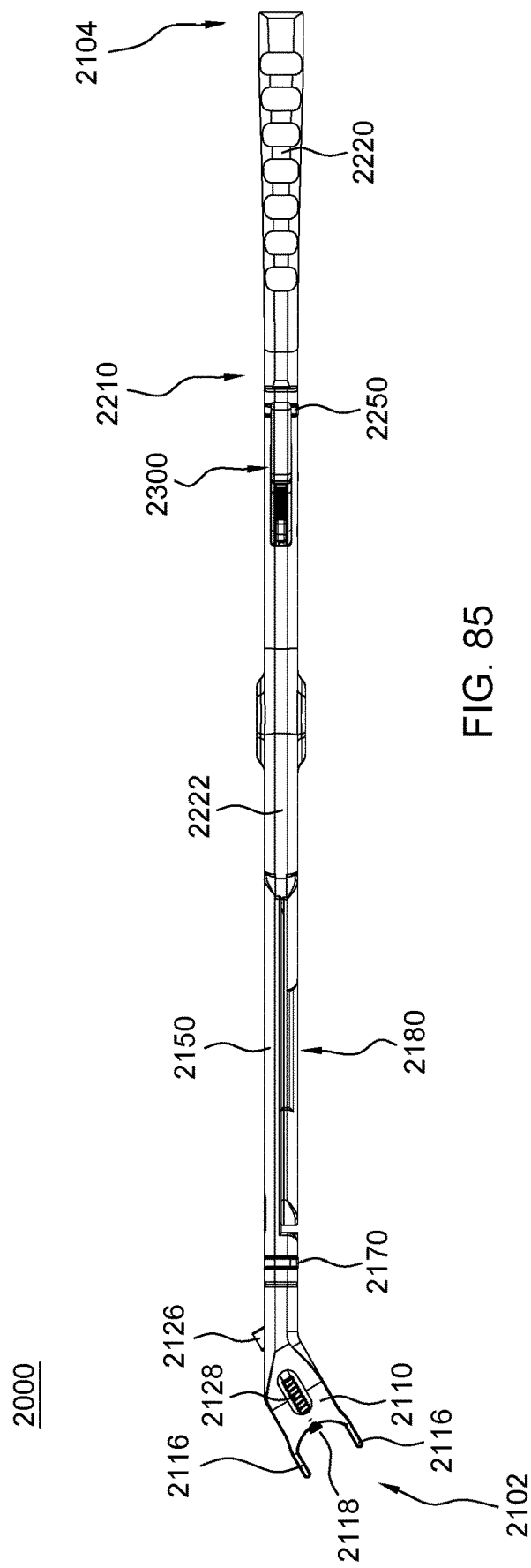
FIG. 85 is a top view of the distraction instrument of FIG. 82, in accordance with an aspect of the present invention.

The first arm 2150 of the distraction instrument 2000, as shown in FIGS. 83, 84, and 86, may include an opening 2152 positioned near the first end of the first arm 2150 extending into a top surface. The opening 2152 may be sized and shaped to receive a securement member 2170. The first arm 2150 may also include an inserter member hole 2154 for receiving the coupling member 2120 of the first inserter member 2110. In addition, the first arm 2150 may include a groove 2156 extending through the side of the first arm 2150 for coupling to a first end 2184 of the first member 2182. The groove 2156 may be positioned, for example, near the first end of the first arm 2150. The first arm 2150 may further include an opening 2158 near the second end of the first arm 2150 for coupling to the second end 2194 of the second member 2190 and the first handle 2210.

The second arm 2160 of the distraction instrument 2000, as shown in FIGS. 83, 84, and 86, may include an opening 2162 positioned near the first end of the second arm 2160 extending into a bottom surface. The opening 2162 may be sized and shaped to receive a securement member 2170. The second arm 2160 may also include an inserter member hole 2164 for receiving the coupling member 2140 of the second inserter member 2130. In addition, the second arm 2160 may include a groove 2166 extending through the side of the second arm 2160 for coupling to a first end 2192 of the second member 2190. The groove 2166 may be positioned, for example, near the first end of the second arm 2160. The second arm 2160 may further include an opening 2168 near the second end for coupling to the second end 2186 of the first member 2182 and the second handle 2230.

As shown in FIG. 86, the distraction system 2180 of the distraction instrument 2000 may include the first member 2182 and the second member 2190. The first member 2182 may include a first end 2184, a second end 2186, and a center opening 2188. The first end 2184 may include an opening for receiving a hinge pin 2198 for moveably coupling the first end 2184 of the first member 2182 to the groove 2156 of the first arm 2150. The second end 2186 may include an opening for receiving a hinge pin 2198 for rotatably coupling the first member 2182 to the second end of the second arm 2160 and the first end of the second handle 2230. The second member 2190 may include a first end 2192, a second end 2194, and a center opening 2196. The first end 2192 may include an opening for receiving a hinge pin 2198 for moveably coupling the first end 2192 of the second member 2190 to the groove 2166 of the second arm 2160. The second end 2194 may include an opening for receiving a hinge pin 2198 for rotatably coupling the second member 2190 to the second end of the first arm 2150 and the first end of the first handle 2210. The center opening 2188 of the first member 2182 may be aligned with the center opening 2196 of the second member 2190 and the center hinge pin 2200 may rotatably couple the first member 2182 to the second member 2190.

As shown in FIG. 86, the first handle 2210 may include a body 2222 removeably coupled to a handle portion 2220. The body 2222 may include an opening 2212 at a first end, a ratchet member opening 2214 near the second end, an opening 2216 at a second end, and a hinge member 2218 positioned between the first end and the second end of the body 2222. The body 2222 may also include an inserter member hole 2224 at the second end. The inserter member hole 2224 may extend into the opening 2216. The handle portion 2220 may include a coupling member 2226 extending away from the first end of the handle portion 2220. The coupling member 2226 may include a locking groove 2228 on a top surface. The coupling member 2226 may be inserted into the inserter member hole 2224 and extend into the opening 2216. A securement member 2250 may be coupled to the opening 2216 to secure the coupling member 2226 of the handle portion 2220 to the body 2222. The securement member 2250 may have a locking protrusion 2252. The locking protrusion 2252 may engage the locking groove 2228 of the coupling member 2226 to secure the handle portion 2220 to the body 2222. The handle portion 2220 may be released from the body 2222 by releasing the securement member 2250.

The second handle 2230 may include a body 2242 removeably coupled to a handle portion 2240. As shown in FIG. 86, the body 2242 may include an opening 2232 at a first end, a ratchet member opening 2234 near the second end, an opening 2236 at a second end, and a hinge member 2238 positioned between the first end and the second end of the body 2242. The body 2242 may also include an inserter member hole 2244 at the second end. The inserter member hole 2244 may extend into the opening 2236. The handle portion 2240 may include a coupling member 2246 extending away from the first end of the handle portion 2240. The coupling member 2246 may include a locking groove 2248 on a bottom surface. The coupling member 2246 may be inserted into the inserter member hole 2244 and extend into the opening 2236. A securement member 2250 may be coupled to the opening 2236 to secure the coupling member 2246 of the handle portion 2240 to the body 2242. The securement member 2250 may have a locking protrusion 2252. The locking protrusion 2252 may engage the locking groove 2248 of the coupling member 2246 to secure the handle portion 2240 to the body 2242. The handle portion 2240 may be released from the body 2242 by releasing the securement member 2250.

Although the first and second handle portions 2220, 2240 are shown as curved handle portions 2220, 2240, alternative first and second handle portions 2220, 2240 are also contemplated. For example, as shown in FIGS. 58 and 71-73, the handle portions 2220, 2240 may come in multiple sizes with varying widths and heights. In addition, the handle portions 2220, 2240 may be, for example, angled along the longitudinal axis, as shown in FIG. 73. The handle portions 2220, 2240 may be, for example, angled in a range of approximately 0° to 90°. The handle portions 2220, 2240 may also come in multiple lengths, widths, and shapes.

With continued reference to FIGS. 82-86, the distraction instrument 2000 may also include a ratcheting mechanism 2300. The ratcheting mechanism 2300 may include, for example, a ratcheting bar 2302 and a lever member 2310. The ratcheting bar 2302 may include, for example, a coupling end 2304 for attachment to the second handle 2230 and teeth 2306 along at least one side of the ratcheting bar 2302 for engaging the lever member 2310. The ratcheting bar 2302 may be, for example, a curved or straight bar. The ratcheting bar 2302 may be secured to the second handle 2230 by, for example, pins 2308.

As shown in FIG. 86, the lever member 2310 may include, for example, a base 2312 and an engagement portion 2320. The base 2312 and engagement portion 2320 may be, for example, integral or separate components. The base 2312 may include, for example, a handle member 2314 for advancing the engagement portion 2320 along the teeth 2306 of the ratcheting bar 2302. The lever member 2310 may also include a spring member 2316 to, for example, retain the ratcheting mechanism 2300 in the desired position along the ratcheting bar 2302. The engagement portion 2320 may include at least one tooth 2322 on at least one side of the engagement portion 2320. The at least one tooth 2322 may be sized and shaped to engage the plurality of teeth 2306 of the ratcheting bar 2302. The lever member 2310 may be moveably coupled to the first handle 2210 by, for example, pins 2324. The lever member 2310 may be positioned, for example, within the ratchet member opening 2214.

The locking driver instrument 1400, as shown in FIGS. 76 and 77 and discussed above, may be used with the distraction instrument 2000 for locking the spacer 1350 in position between the first and second portions 1320, 1340 of the spinal implant 1300. The threaded rod driver instrument 1420, as shown in FIGS. 78 and 79 and described in greater detail above, may also be used with the distraction instrument 2000 to secure the threaded rods 2126, 2146 of the distraction instrument 2000 to the spinal implant 1300.

As shown in FIGS. 82-85, the distraction instrument 2000 may be assembled by attaching the first body 2222 to the second body 2242 with a pin 2206. A spring member 2208 may be positioned, for example, around the pin 2206 and positioned to engage the first and second bodies 2222, 2242. The lever member 2310 may be coupled to the body 2222 of the first handle 2210 and the ratcheting bar 2302 may be coupled to the body 2242 of the second handle 2230. The opening 2212 of the body 2222 may be aligned with the opening 2158 of the first arm 2150 and the opening in the second end 2194 of the second member 2190. A pin 2198 may be inserted through the opening 2212, opening 2158, and the opening in the second end 2194 to attach the first body 2222, the first arm 2150, and the second member 2190. In addition, the opening 2232 of the second body 2242 may be aligned with the opening 2168 of the second arm 2160 and the opening in the second end 2186 of the first member 2182. A pin 2198 may be inserted through the opening 2232, the opening 2168 and the opening in the second end 2186 to attach the second body 2242, the second arm 2160, and the first member 2182. The center opening 2188 of the first member 2182 may be aligned with the center opening 2196 of the second member 2190. Then, a center hinge pin 2200 is inserted into the openings 2188, 2196 to moveably couple the first member 2182 to the second member 2196.

Next, with continued reference to FIGS. 82-85, the opening in the first end 2184 of the first member 2182 is aligned with the groove 2156 of the first arm 2150 and a pin 2198 may be used to moveably secure the first member 2182 to the first arm 2150. The pin 2198 may translate within the groove 2156 to allow for the distraction instrument 2000 to expand. The opening in the first end 2192 of the second member 2190 may be aligned with the groove 2166 of the second arm 2160 and a pin 2198 may be used to moveably secure the second member 2190 to the second arm 2160. The pin 2198 may translate within the groove 2166 to allow for the distraction instrument 2000 to expand. In addition, a securement member 2170 may be inserted into the opening 2152 in the first arm 2150 and a securement member 2170 may be inserted into the opening 2162 in the second arm 2160. In addition, a securement member 2250 may be inserted into the opening 2216 in the first body 2222 and a securement member 2250 may be inserted into the opening 2236 in the second body 2242. The securement members 2170, 2250 may be secured in the openings 2152, 2162, 2216, 2236 using fasteners 2174, 2254, for example, pins, screws, rivets, or the like, that allows the securement members 2170, 2250 to move with respect to the openings 2152, 2162, 2216, 2316.

Then, as discussed in greater detail above with reference to distraction instrument 1000, which will not be described again here for brevity sake, the spring 2128 and the threaded rod 2126 may be inserted into the opening 2114 in the first inserter member 2110 and the spring 2148 and threaded rod 2146 may be inserted into the opening 2134 in the second inserter member 2130. The springs 2128, 2148 and threaded rods 2126, 2146 may be of the type described above with reference to springs 1128, 1148 and threaded rods 1126, 1146, respectively. The threaded rods 2126, 2146 may engage a portion of a spinal implant, such as implant 400, 1300.

The first inserter member 2110 may be coupled to the first arm 2150 by inserting the coupling member 2120 into the inserter member hole 2154. The locking protrusion 2172 may engage the locking groove 2122 to secure the first inserter member 2110 to the first arm 2150. The second inserter member 2130 may be coupled to the second arm 2160 by inserting the coupling member 2140 into the inserter member hole 2164. The locking protrusion 2172 may engage the locking groove 2142 to secure the second inserter member 2130 to the second arm 2160. The first handle portion 2220 may be coupled to the first body 2222 by inserting the coupling member 2226 into the inserter member hole 2224. The locking protrusion 2252 may engage the locking groove 2228 to secure the handle portion 2220 to the first body 2222. The second handle portion 2240 may be coupled to the second body 2242 by inserting the coupling member 2246 into the inserter member hole 2244.

The locking protrusion 2252 may engage the locking groove 2248 to secure the handle portion 2240 to the second body 2242.

The distraction instrument 2000 may be used in place of distraction instrument 1000 for inserting a spinal implant 1300 as described in reference to the method of use described in greater detail above with reference to FIGS. 62-68. When the distraction instrument 2000 is used, the ratcheting mechanism 2300 maintains the expanded position of the inserter members 2110, 2130 and the first and second portions 1320, 1340 while the spacer 1350 is inserted between the first and second portions 1320, 1340.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been depicted and described with reference to example embodiments. It will be understood that the architectural and operational embodiments described herein are exemplary of a plurality of possible arrangements to provide the same general features, characteristics, and general system operation. Modifications, substitutions, and alterations will occur to others upon a reading and understanding of the preceding detailed description. It is intended that the invention be construed as including all such modifications and alterations and therefore these changes be considered to be within the scope of the following claims.

What is claimed is:

1. A spinal implant replacement instrument kit, comprising:
    a distraction instrument; and
    a spinal implant, wherein the spinal implant comprises an intermediate spacer comprising a longitudinal axis, an outer surface, and a first end and a second end, wherein the distance between the first and second ends defines a length of the intermediate spacer;
    a first member removably coupled to the first end of the intermediate spacer; and
    a second member removably coupled to the second end of the intermediate spacer, wherein the intermediate spacer further comprises:
    a gap on a first side extending from the first end to the second end; wherein the gap extends from the outer surface into a central bore of the intermediate spacer;
    an instrument coupling mechanism comprising at least one groove extending on a third side of the intermediate spacer, wherein the at least one groove extends along a lateral direction from the first side to a second side; and
    a first planar outer surface portion positioned on the third side and a second planar outer surface portion positioned on a fourth side of the intermediate spacer outer surface, wherein the fourth side is opposite the third side, wherein the first and second planar outer surface portions are positioned between the first end and the instrument coupling mechanism;
    a first coupling mechanism on the first end of the intermediate spacer for engaging a coupling mechanism of a first member; and
    a second coupling mechanism on the second end of the intermediate spacer for engaging a coupling mechanism of a second member.

2. The spinal implant replacement instrument kit of claim 1, wherein the first and second planar outer surface portions taper away from each other as they extend along a lateral direction.

3. The spinal implant replacement instrument kit of claim 1,
    wherein the distraction instrument comprises:
    a first inserter member;
    a second inserter member;
    a first arm coupled to the first inserter member;
    a second arm coupled to the second inserter member;
    a distraction system engaging the first arm and second arm;
    a first handle coupled to the first arm and the distraction system; and
    a second handle coupled to the second arm and the distraction system;
    wherein the first inserter member and the second inserter member couple to the spinal implant and actuation of the first handle and the second handle translates the first inserter member with respect to the second inserter member.

4. The spinal implant replacement instrument kit of claim 3, wherein the distraction instrument further comprises a ratcheting mechanism positioned to engage the first handle and the second handle.

5. The spinal implant replacement instrument kit of claim 4,
    wherein the first inserter member comprises:
    a body, wherein the body comprises:
    a first opening extending from a top surface through to a bottom surface of the body;
    engagement protrusions extending out from a first end of the body;
    a hole extending from a side of the body through the first opening and out the first end of the body;
    a coupling member extending out from a second end of the body for engaging the first arm; and
    an insertion track inset into the bottom surface of the body and extending from the first end of the body to the side of the body;
    a spring positioned within the hole of the body; and
    a threaded rod positioned within the spring in the hole of the body.

6. The spinal implant replacement instrument kit of claim 5,
    wherein the second inserter member comprises:
    a body, wherein the body comprises:
    a first opening extending from a top surface through to a bottom surface of the body;
    engagement protrusions extending out from a first end of the body;
    a hole extending from a side of the body through the first opening and out the first end of the body;

a coupling member extending out from a second end of the body for engaging the first arm; and an insertion track inset into the top surface of the body and extending from the first end of the body to the side of the body;

a spring positioned within the hole of the body; and a threaded rod positioned within the spring in the hole of the body.

7. The spinal implant replacement instrument kit of claim 6, wherein the first arm comprises:

a first opening positioned near a first end of the first arm and extending into a top surface of the first arm;

an inserter member hole sized and shaped to receive the coupling member of the body of the first inserter member;

a groove extending through a side of the first arm; and a second opening positioned near a second end of the first arm.

8. The spinal implant replacement instrument kit of claim 7, wherein the second arm comprises:

a first opening positioned near a first end of the second arm and extending into a bottom surface of the second arm;

an inserter member hole sized and shaped to receive the coupling member of the body of the second inserter member;

a groove extending through a side of the second arm; and a second opening positioned near a second end of the second arm.

9. The spinal implant replacement instrument kit of claim 8, wherein the distraction system comprises:

a first member;

a second member; and a hinge pin coupling the first member and the second member.

10. The spinal implant replacement instrument kit of claim 9, wherein the first member of the distraction system comprises:

a first end with an opening for receiving a hinge pin to couple the first end to the groove of the first arm;

a second end with an opening for receiving a hinge pin to rotatably couple the second end to the second opening of the second arm and a first end of the second handle; and a center opening for receiving the hinge pin to couple the first member to the second member.

11. The spinal implant replacement instrument kit of claim 10, wherein the second member of the distraction system comprises:

a first end with an opening for receiving a hinge pin to couple the first end to the groove of the second arm;

a second end with an opening for receiving a hinge pin to rotatably couple the second end to the second opening of the first arm and a first end of the first handle; and a center opening for receiving the hinge pin to couple the first member to the second member.

12. The spinal implant replacement instrument kit of claim 11, wherein the first handle comprises:

a body; and a handle portion with a coupling member at a first end, the coupling member including a locking groove for coupling the handle portion to the body.

13. The spinal implant replacement instrument kit of claim 12, wherein the body of the first handle comprises:

a first opening at a first end of the body for coupling to the second end of the second member of the distraction system and the second opening of the first arm;

a ratchet member opening near a second end of the body configured to receive a portion of the ratcheting mechanism;

an inserter member hole at the second end, wherein the inserter member hole extends into the body in a longitudinal direction from the second end;

a second opening at a second end of the body and extending into the inserter member hole, wherein the second opening receives a securement member; and a hinge member positioned between the first end and the second end.

14. The spinal implant replacement instrument kit of claim 13, wherein the second handle comprises:

a body; and a handle portion with a coupling member at a first end, the coupling member includes a locking groove for securing the handle portion to the body.

15. The spinal implant replacement instrument kit of claim 14, wherein the body of the second handle comprises:

a first opening near a first end of the body for coupling to the first member of the distraction system and the second opening of the second arm;

a ratchet member opening near a second end of the body configured to receive a portion of the ratcheting mechanism;

an inserter member hole at the second end, wherein the inserter member hole extends into the body in a longitudinal direction from the second end;

a second opening at a second end of the body and extending into the inserter member hole, wherein the second opening receives a securement member; and a hinge member positioned between the first end and the second end, and wherein the hinge member of the second handle is rotatably coupled to the hinge member of the first handle with a pin.

16. The spinal implant replacement instrument kit of claim 15, wherein the ratcheting mechanism comprises:

a ratcheting bar with a plurality of teeth along a side of the ratcheting bar; and a lever member with an engagement portion including at least one tooth sized and shaped to engage the plurality of teeth of the ratcheting bar.

17. The spinal implant replacement instrument kit of claim 1, wherein the first coupling mechanism at the first end and the second coupling mechanism at the second end each comprise two projections.

18. The spinal implant replacement instrument kit of claim 17, wherein each of the two projections define a male dovetail-shaped projection positioned at the first end and the second end.

19. The spinal implant replacement instrument kit of claim 1, wherein the coupling mechanism for each of the first member and the second member comprise a female dovetail-shaped recess.

20. The spinal implant replacement instrument kit of claim 19, wherein the female dovetail-shaped recess of the first member and the second member slideably engage the male dovetail-shaped projections positioned at the first end and the second end respectively of the intermediate spacer.

21. The spinal implant replacement instrument kit of claim 1, wherein the spinal implant further comprising a first end member and a second end member.

22. The spinal implant replacement instrument kit of claim 21, wherein the first member is coupled to the first end member by the interaction between a coupling member of the first end member and an engagement portion of the first member; and wherein the second member is coupled to the second end member by the interaction between a coupling member of the second end member and an engagement portion of the second member.

23. A distraction instrument, comprising:
- a first inserter member, wherein the first inserter member comprises a first engagement member extending through an opening in the first inserter member;
- a second inserter member, wherein the second inserter member comprises a second engagement member extending through an opening in the second inserter member;
- a first arm coupled to the first inserter member;
- a second arm coupled to the second inserter member;
- a distraction system coupled to the first arm and second arm;
- a first handle coupled to the first arm and the distraction system;
- a second handle coupled to the second arm and the distraction system; and
- wherein actuation of the first handle and the second handle moves the distraction system and movement of the distraction system moves the first arm and the second arm to translate the first inserter member with respect to the second inserter member, wherein at least a portion of the first inserter member is angled away from a longitudinal axis of the first arm, and wherein at least a portion of the second inserter member is angled away from a longitudinal axis of the second arm.

24. A surgical method for inserting a vertebral body replacement device, comprising:
- obtaining the vertebral body replacement device and a distraction instrument;
- making an incision to expose a patient's spine;
- preparing a space within the patient's spine for receiving the vertebral body replacement device;
- attaching a first member and a second member of the vertebral body replacement device to the distraction instrument;
- inserting the first member and the second member of the vertebral body replacement device into the space within the spine;
- moving the distraction instrument to separate the first member and the second member;
- coupling a spacer to a spacer inserter;
- moving the coupled spacer and spacer inserter through the distraction instrument into position between the first member and the second member;
- disengaging the spacer inserter from the spacer and removing the spacer inserter from the distraction instrument;
- disengaging the distraction instrument from the first member and the second member of the vertebral body replacement device; and
- closing the incision.

* * * * *